United States Patent
Ren et al.

(10) Patent No.: US 10,364,247 B2
(45) Date of Patent: Jul. 30, 2019

(54) PREPARATION AND USE OF NOVEL PROTEIN KINASE INHIBITORS

(71) Applicants: Ruijin Hospital Affiliated to Shanghai Jiao Tong University School of Medicine, Shanghai (CN); Xiamen University, Xiamen, Fujian (CN); Brandeis University, Waltham, MA (US)

(72) Inventors: Ruibao Ren, Shanghai (CN); Xianming Deng, Fujian (CN); Ping Liu, Shanghai (CN); Bo Jiao, Shanghai (CN); Wei Huang, Fujian (CN)

(73) Assignees: Ruijin Hospital Affiliated to Shanghai Jiao Tong University School of Medicine, Shanghai (CN); Xiamen University, Xiamen, Fujian (CN); Brandeis University, Waltham, MA (US)

(*) Notice: Subject to any disclaimer, the term of this patent is extended or adjusted under 35 U.S.C. 154(b) by 0 days.

(21) Appl. No.: 15/567,814

(22) PCT Filed: Apr. 21, 2015

(86) PCT No.: PCT/CN2015/077128
§ 371 (c)(1),
(2) Date: Oct. 19, 2017

(87) PCT Pub. No.: WO2016/168992
PCT Pub. Date: Oct. 27, 2016

(65) Prior Publication Data
US 2018/0105528 A1    Apr. 19, 2018

(51) Int. Cl.
*C07D 487/04* (2006.01)
*A61P 35/00* (2006.01)
*A61P 35/02* (2006.01)

(52) U.S. Cl.
CPC .................. *C07D 487/04* (2013.01)

(58) Field of Classification Search
None
See application file for complete search history.

(56) References Cited

U.S. PATENT DOCUMENTS 5,654,307 A * 8/1997 Bridges ............... C07D 239/70
514/224.5

FOREIGN PATENT DOCUMENTS

| CN | 104418860 A | 3/2015 | |
|---|---|---|---|
| WO | WO-2015092431 A1 * | 6/2015 | ........... C07D 487/14 |
| WO | WO-2016/168992 A1 | 10/2016 | |

OTHER PUBLICATIONS

Zhang, Jiannning. Nature Reviews Cancer. vol. 9 (2009) 28-39.*
MedicineNet.com (2004) Web <http://www.medterms.com>.*
Meanwell, Nicholas. J. Med. Chem. (2011) 54 2529-2591.*
Choi, Hwan Geun. J. Med. Chem. 2010, 53, 5439-5448.*
International Search Report for PCT/CN2015/077128, 6 pages (dated Jan. 27, 2016).
Written Opinion for PCT/CN2015/077128, 5 pages (dated Jan. 27, 2016).

* cited by examiner

*Primary Examiner* — Emily A Bernhardt
*Assistant Examiner* — Laura M Daniel
(74) *Attorney, Agent, or Firm* — Choate, Hall & Stewart LLP; Brenda Herschbach Jarrell; Michael L. Vetter

(57) ABSTRACT

The invention provides novel compounds and methods of using such compounds to treat or prevent cancer.

6 Claims, 3 Drawing Sheets

PREPARATION AND USE OF NOVEL PROTEIN KINASE INHIBITORS

BACKGROUND

Protein kinases represent a large family of proteins which play a central role in the regulation of a wide variety of cellular processes and maintaining control over cellular function. Kinases are implicated in numerous cancers and therefore have been attractive therapeutic targets. However, resistance to kinase-directed therapies can develop.

SUMMARY

The present disclosure provides, among other things, certain compounds (and compositions thereof) and demonstrates their usefulness, for example, as inhibitors of one or more protein kinases. In some embodiments, provided compounds and/or compositions are useful in medicine. In some embodiments, provided compounds and/or compositions are useful in treatment (e.g., therapeutic and/or prophylactic treatment) of one or more kinase-associated diseases, disorders or conditions (e.g, diseases, disorders, or conditions associated with level and/or activity of one or more kinases, including particularly diseases, disorders or conditions associated with one or more deregulated protein kinase pathways, or otherwise associated with elevated level and/or activity of one or more kinases as compared with that observed absent the disease, disorder or condition).

In some particular embodiments, provided compounds and/or compositions are useful in the treatment of cancer. In some embodiments, the cancer may be or comprise chronic myeloid leukemia (CML), acute lymphocytic leukemia (ALL), acute myeloid leukemia (AML), lung cancer, melanoma, colorectal cancer, etc.

In some embodiments, kinases of interest in accordance with the present invention include one or more tyrosine kinases, e.g., receptor tyrosine kinases. In some embodiments, kinases of interest include one or more of ABL (e.g., BCR/ABL) EGFR, EPHA, EPHB, FLT3, KIT, RET, TXK, BRAF and RAS. In some particular embodiments, the kinase is or comprises RAS.

In some embodiments, a provided compound and/or composition is considered to be active with respect to a particular kinase if kinase activity is altered (e.g., reduced) at least 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 60-fold, 70-fold, 80-fold, 90-fold, or more when the compound or composition is present as compared with when it is absent. Alternatively or additionally, in some embodiments, a provided compound and/or composition is considered to be active with respect to a particular kinase if kinase activity is reduced at least 50%, 60%, 70%, 80%, 90%, 95%, or 99% in its presence as compared with in its absence. In some embodiments, a provided compound and/or composition is considered to be active with respect to a particular kinase if kinase activity is reduced below a known threshold level, and/or to a degree comparable to that observed when an appropriate positive control compound or composition is present, when the compound or composition is present but not when it is absent.

In some embodiments, a provided compound and/or composition is considered to be an inhibitor of a particular kinase if it shows an IC50 (μM) with respect to that kinase that is below about 2 μM, 1 μM, 0.1 μM, 0.01 μM, or 0.001 μM or less. In some particular embodiments, a provided compound and/or composition is considered to be an inhibitor of a particular kinase if it shows an IC50 (μM) with respect to that kinase that is below about 2 μM, 0.2 μM, 0.02 μM or less.

In some embodiments, a provided compound and/or composition is considered to be an inhibitor of a particular kinase if it shows an IC50 (μM) with respect to that kinase that is at least 2-fold, 3-fold, 4-fold, 5-fold, 6-fold, 7-fold, 8-fold, 9-fold, 10-fold or more reduced when relative to the IC50 (μM) of a reference inhibitor of that kinase.

In some embodiments, a provided compound and/or compositions show activity that is specific for a particular kinase or set of kinases in that the compound and/or composition has a more significant effect on level and/or activity of the relevant kinase or set of kinases than it does on at least one different kinase or set of kinases. In some embodiments, a provided compound or composition shows activity that is specific for a single kinase. In some embodiments, a provided compound is considered to be specific to a particular kinase or set of kinases if it exhibits at least 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold greater effect on the particular kinase of interest relative to one or more appropriate reference kinases under comparable conditions. For example, in some particular embodiments, effect of a provided compound and/or composition is assessed with respect to activity of a plurality of different kinases, each of which is individually (or multiply) expressed in an appropriate host cell, and differential activity of the compound and/or composition with respect to one or more of the kinases is assessed.

In some embodiments, provided compounds and/or compositions are particularly useful for treatment of one or more diseases, disorders, or conditions in a subject or subjects who has/have developed or is/are at risk of developing resistance to one or more alternative agents (e.g., one or more other kinase inhibitors) that may be or have been used to treat the disease, disorder, or condition in the subject or subjects.

In some embodiments, provided compounds and/or compositions are particularly useful in combination therapy regimens with one or more other therapies for treatment of the relevant disease, disorder, or condition.

In some embodiments, the present disclosure provides and/or utilizes one or more compounds whose structure is given by general formula I:

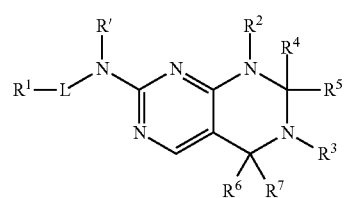

wherein each variable is as defined and described herein.

Those skilled in the art, reading the present disclosure will appreciate that, various embodiments, compounds of formula I may be utilized in a particular form such as for example, a particular salt form (e.g., a pharmaceutically acceptable salt form), a particular prodrug form (e.g., in which one or more moieties is or is modified by a leaving group that is or is expected to be removed under physiological conditions and/or specifically when a compound in present in a particular physiological location or site), a particular ester form, a particular protected form (e.g., in which one or more indicated moieties comprises or is modified by a protecting group, as is known in the art), etc. In some embodiments, one or more atoms of a compound of formula I may be substituted with a different isomer or isotope (e.g., deuterium or tritium for hydrogen, etc).

In some embodiments, a provided compound may be provided and/or utilized in a particular crystalline form, or in an amorphous form. In certain embodiments, a crystalline form may be or comprise a particular polymorph, hydrate, solvate, etc, or a combination thereof.

In some embodiments, a provided compound may be provided and/or utilized in a particular isomeric form, or in a particular combination of isomeric forms. In some embodiments, a provided compound may include one or more stereocenters, and may be provided and/or utilized in a particular stereoisomeric form, or combinations thereof. In some embodiments, a compound may be provided and/or utilized in a form that includes approximately equal amounts of two or more different isomeric or stereoisomeric forms. In some embodiments, a compound may be provided and/or utilized in a form that is enriched for one or more isomeric or stereoisomeric forms. In some embodiments, a compound may be utilized in racemic form. In some embodiments, where a compound may contain more than one isomeric site (e.g., more than one stereocenter), the compound may be utilized in a form that is enriched with respect to one form of one isomeric site but may or may not be so enriched with respect to any particular form at another isomeric site.

In some embodiments, a provided compound may be utilized in a particular tautomeric form.

In some embodiments, a provided compound may be utilized in a form that is associated with a detectable moiety (e.g., a fluorophore, a radioisotope, an enzyme, a metal, and/or another direct or indirect label). In some embodiments, a provided compound may be utilized in a form that is associated with a carrier moiety. In some embodiments, a carrier moiety may be or comprise a targeting moiety (e.g., that interacts with a particular target of interest, for example, in or on a cell, tissue, or organism).

In some embodiments, a compound may be provided and/or utilized in a form that is about 55%, 60%, 65%, 70%, 75%, 80%, 85%, 90%, 95%, 96%, 97%, 98%, 99%, or 100% pure with respect to other relevant forms (e.g., with respect to other salt forms, solid forms, isomeric or stereoisomeric forms, tautomeric forms, detectable forms, carrier-associated forms, etc).

BRIEF DESCRIPTION OF THE DRAWING

Table 1: shows representative compounds of Formula I.
Table 2: shows KINOMEscan data of compound IA-9.
Table 3: shows antiproliferative activities of compounds of the invention against BaF3-BCR/ABL, BaF3-BCR/ABL-T315I, BaF3-TEL-TIE1 and BaF3-TEL-LYN.
Table 4: shows antiproliferative activities of compounds of the invention against BaF3-EML4-ALK, BaF3-TEL-INSR, and BaF3-TEL-HCK.
Table 5: shows antiproliferative activities of compounds of the invention against BaF3-NRASD12, BaF3-KRASD12, and Wt-BaF3.

DEFINITIONS

Figure 1:
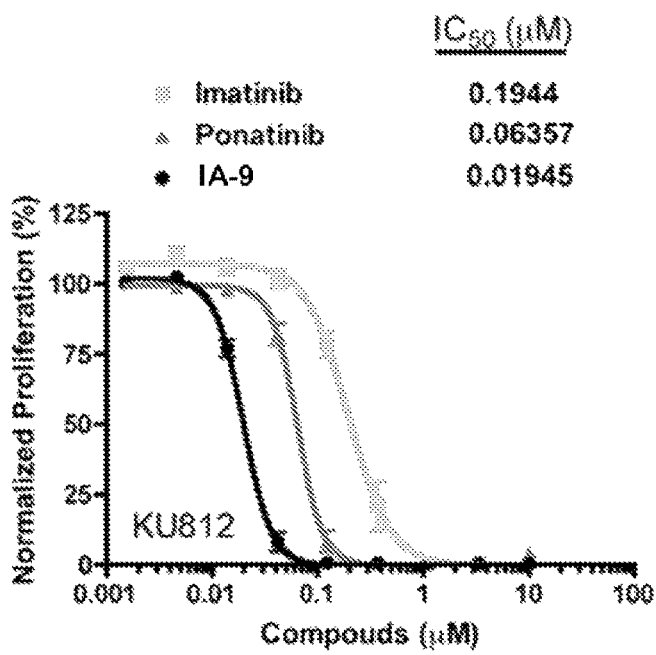
FIG. 1: shows inhibition of human leukemia cell proliferation by compound IA-9. Comparison of 50% inhibition concentration (IC50) of IA-9, imatinib and Ponatinib in KU812 leukemia cells.

Administration: As used herein, the term "administration" refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. For example, in certain embodiments, administration to an animal subject (e.g., to a human) may be bronchial (including by bronchial instillation), buccal, enteral, interdermal, intraarterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Agent: The term "agent" as used herein may refer to a compound or entity of any chemical class including, for example, polypeptides, nucleic acids, carbohydrates, lipids, small molecules, metals, and/or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. In some particular embodiments, an agent is or comprises a small molecule, an antibody, an antibody fragment, an aptamer, an siRNA, an shRNA, a DNA/RNA hybrid, an antisense oligonucleotide, a ribozyme, a peptide, a peptide mimetic, a peptide nucleic acid ("PNA") etc. In some embodiments, and agent is an activator or an inhibitor. In some embodiments, an agent has an $IC_{50}$ and/or binding constant of less about 50 µM, less than about 1 µM, less than about 500 nM, less than about 100 nM, less than about 20 nM less than about 10 nM, less than about 9 nM, less than about 9 nM, less than about 7 nM, less than about 6 nM, less than about 5 nM, less than about 4 nM, less than about 3 nM, less than about 2 nM, or less than about 1 nM.

In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety. In some embodiments, an agent is provided and/or utilized in salt form.

Antiproliferative Agent: As used herein, the term "antiproliferative agent" refers to a substance that, when administered or applied to a source of dividing cells (e.g., a cell culture, a tissue sample, an organism, etc), reduces the extent (e.g., the number of cell doublings) and/or frequency (e.g., the rate of cell division events) of cell proliferation as compared with that observed under otherwise comparable conditions absence the antiproliferative agent.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Combination therapy: As used herein, the term "combination therapy" refers to those situations in which a subject is simultaneously exposed to two or more therapeutic regimens or modalities (e.g., to two or more therapeutic agents). In some embodiments, two or more regimens or modalities are administered or applied simultaneously (e.g., one or more individual doses of each of two or more agents, may be administered at substantially the same time); in some embodiments, such regimens or modalities may be administered sequentially (e.g., at least a first dose of a first agent is administered prior to at least a first dose of a second agent); in some embodiments, such regimens or modalities such that individual doses or applications overlap.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.)

Determine: Certain methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage form: and "unit dosage form", as used herein, the term "dosage form" refers to physically discrete unit of a therapeutic agent for a subject (e.g., a human patient) to be treated). In some embodiments, each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage (e.g., total daily dosage) administered to any particular patient will typically be selected by a medical professional (e.g., a medical doctor) within the scope of sound medical judgment, and may include more than one such discrete unit, and/or may utilize a fraction of a discrete unit.

Dosing regimen: (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Improve, increase, reduce, etc: As used herein, terms such as "improve", "increase", "reduce", etc., which necessarily imply a comparison, refer to a comparison with an appropriate comparable reference or standard. For example, in some embodiments, level and/or activity of an agent or marker of interest may be reduced under a set of conditions or circumstances of interest (e.g., after administration of therapy) as compared with its level and/or activity under a comparable set of conditions (e.g., prior to administration of the therapy or after administration of the therapy to an appropriate reference subject). In some embodiments, an appropriate reference may be a historical reference. In some embodiments, an appropriate reference may be an average, e.g., as may be observed within or across a relevant population.

Measurable: The term "measurable" is used herein to describe a characteristic of being both detectable under conditions of a relevant assay (e.g., in vitro and/or in vivo). In some embodiments, to be considered "measurable", the parameter of interest is also distinguishable, e.g., from a relevant reference parameter. Those of ordinary skill in the art will appreciate that not every parameter that may be theoretically of interest is in fact "measurable" in a particular sample, assay, etc.

Receptor tyrosine kinase: The term "receptor tyrosine kinase", as used herein, refers to members of the protein family of receptor tyrosine kinases (RTK), which includes but is not limited to sub-families such as Epidermal Growth Factor Receptors (EGFR) (including ErbB1/EGFR, ErbB2/HER2, ErbB3/HER3, and ErbB4/HER4), Fibroblast Growth Factor Receptors (FGFR) (including FGF1, FGF2, FGF3, FGF4, FGF5, FGF6, FGF7, FGF18, and FGF21), Vascular Endothelial Growth Factor Receptors (VEGFR) (including VEGF-A, VEGF-B, VEGF-C, VEGF-D, and PIGF), FMS-Related Tyrosine Kinase (e.g., FLT3), RET Receptor and the Eph Receptor Family (including EphA1, EphA2, EphA3, EphA4, EphA5, EphA6, EphA7, EphA8, EphA9, EphA10, EphB1, EphB2. EphB3, EphB4, and EphB6).

Reference: as used herein the term "reference" describes a standard, control, or other appropriate reference against which a comparison is made as described herein. For example, in some embodiments, a reference is a standard or control agent, animal, individual, population, sample, sequence, series of steps, set of conditions, or value against which an agent, animal, individual, population, sample, sequence, series of steps, set of conditions, or value of interest is compared. In some embodiments, a reference is tested and/or determined substantially simultaneously with the testing or determination of interest. In some embodiments, a reference is a historical reference, optionally embodied in a tangible medium. Typically, as would be understood by those skilled in the art, a reference is determined or characterized under conditions comparable to those utilized in the assessment of interest.

Refractory: As used herein, the term "refractory" refers to any subject or condition that does not respond with an expected clinical efficacy following the administration of provided compositions as normally observed by practicing medical personnel.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, the term "sample" typically refers to a biological sample obtained or derived from a source of interest, as described herein. In some embodiments, a biological sample is a cell culture or extracts thereof. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchioalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Specific: The term "specific", when used herein with reference to an agent having an activity, is understood by those skilled in the art to mean that the agent discriminates between potential target entities or states. For example, an in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

Subject: as used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic regimen: A "therapeutic regimen", as that term is used herein, refers to a dosing regimen whose administration across a relevant population is or is expected to be correlated with a desired or beneficial therapeutic outcome.

Therapeutically effective amount: as used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

DETAILED DESCRIPTION OF CERTAIN EMBODIMENTS

1. General Description of Certain Embodiments of Compounds of Formula I

In certain embodiments, a compound of formula I as described and/or utilized herein has the structure:

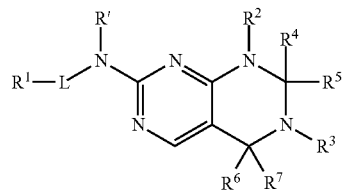

I wherein:
R' is hydrogen or $C_{1-6}$ aliphatic;
L is a covalent bond, —S—, —S(O)—, —S(O)$_2$—, or —C(O)—;
$R^1$ is selected from hydrogen, —OR, —SR, —N(R)$_2$, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;
each R is independently selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur;
each of $R^2$ and $R^3$ is independently selected from hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;
each of $R^4$ and $R^5$ is independently selected from hydrogen or $C_{1-3}$ aliphatic, or $R^4$ and $R^5$ are taken together with their intervening atoms to form a 3-6 membered saturated carbocyclic ring; and
each of $R^6$ and $R^7$ is independently hydrogen or optionally substituted $C_{1-6}$ aliphatic.

2. Definitions of Chemical Terms

Compounds of this invention include those described generally above, and furthermore are illustrated by classes, subclasses, and species disclosed herein. As used herein, the following definitions shall apply to chemical terms (e.g., as utilized in description of compounds of formula I) unless otherwise indicated. For purposes of the present disclosure, chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond.

The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O (CH$_2$)$_{0-4}$R°, —O—(CH$_2$)$_{0-4}$C(O)OR°; —(CH$_2$)$_{0-4}$CH (OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N (R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S) SR°, —(CH$_2$)$_{0-4}$OC(O)NR°$_2$; —C(O)N(OR°)R°; —C(O)C (O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SRR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As will be appreciated by those skilled in the art, structures depicted herein may represent compounds that exist in one or more different isomeric (e.g., enantiomeric, diastereomeric, and/or geometric (or conformational)) forms. For example, in some embodiments, a depicted structure may include one or more asymmetric centers, which can exist in R and S configurations, and/or may include one or more double bonds, which may exist in Z and E conformational isomers. Alternatively or additionally, structures depicted herein may represent compounds that exist in one or more tautomeric forms.

As described herein, in some embodiments, compounds maybe provided and/or utilized in accordance with the present invention in any particular form (or combinations thereof), including any particular isomeric form(s) or combination thereof, any particular tautomeric form(s) or combination thereof, etc.

Alternatively or additionally, as also described herein, in some embodiments, the present disclosure provides and/or utilizes compounds of formula I, wherein one or more atoms may be present in one or more alternative isotopic forms. For example, in some embodiments, one or more hydrogen atoms as depicted in formula I may represent a deuterium or tritium; one or more carbon atoms as depicted in formula I may represent a $^{13}$C- or $^{14}$C-enriched carbon, etc.

In some embodiments, compounds or compositions, or particular forms thereof, may be useful in accordance with the present invention, for example, as analytical tools, as probes in biological assays, as synthetic or other preparative intermediates, and/or as therapeutic agents in accordance with the present invention.

3. Description of Certain Exemplary Embodiments

As described herein, in some embodiments the present invention provides and/or utilizes a compound of formula I:

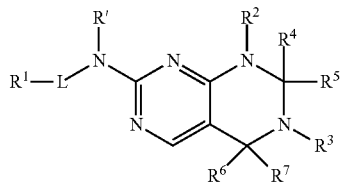

or a pharmaceutically acceptable salt thereof, wherein:
R' is hydrogen or $C_{1-6}$ aliphatic;
L is a covalent bond, —S—, —S(O)—, —S(O)$_2$—, or —C(O)—;
$R^1$ is selected from hydrogen, —OR, —SR, —N(R)$_2$, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;
each R is independently selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur;
each of $R^2$ and $R^3$ is independently selected from hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;
each of $R^4$ and $R^5$ is independently selected from hydrogen or $C_{1-3}$ aliphatic, or $R^4$ and $R^5$ are taken together with their intervening atoms to form a 3-6 membered saturated carbocyclic ring; and
each of $R^6$ and $R^7$ is independently hydrogen or optionally substituted $C_{1-6}$ aliphatic.

As defined above, R' is hydrogen or $C_{1-6}$ aliphatic. In some embodiments, R' is hydrogen. In other embodiments, R' is $C_{1-6}$ aliphatic.

As defined above, L is a covalent bond, —S—, —S(O)—, —S(O)$_2$—, or —C(O)—. In certain embodiments, L is a covalent bond. In other embodiments, L is —S—, —S(O)—, —S(O)$_2$—, or —C(O)—.

As defined above, $R^1$ is selected from hydrogen, —OR, —SR, —N(R)$_2$, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, $R^1$ is hydrogen. In other embodiments, $R^1$ is selected from —OR, —SR, —N(R)$_2$, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In certain embodiments, $R^1$ is selected from —OR, —SR, or —N(R)$_2$. In some embodiments, $R^1$ is —OR. In some embodiments, $R^1$ is —SR. In some embodiments, $R^1$ is —N(R)$_2$.

In some embodiments, $R^1$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, $R^1$ is an optionally substituted aliphatic group. In some embodiments, $R^1$ is methyl. In some embodiments, $R^1$ is optionally substituted methyl. In some embodiments, $R^1$ is ethyl. In some embodiments, $R^1$ is optionally substituted ethyl. In some embodiments, $R^1$ is 2-(dimethylamino)ethyl. In some embodiments, $R^1$ is 2-morpholinoethyl. In some embodiments, $R^1$ is 2-(1H-imidazol-4-yl)ethyl. In some embodiments, $R^1$ is propyl. In some embodiments, $R^1$ is optionally substituted propyl. In some embodiments, $R^1$ is 1-hydroxypropan-2-yl.

In some embodiments, $R^1$ is phenyl. In some embodiments, $R^1$ is optionally substituted phenyl. In some embodiments, $R^1$ is 2-methoxy-4-(4-methylpiperazine-1-carbonyl) phenyl.

In certain embodiments, $R^1$ is an optionally substituted 3-8 member saturated or partially unsaturated carbocyclic ring. In some embodiments, $R^1$ is cyclopropyl.

In some embodiments, $R^1$ is an optionally substituted 4-7 membered heterocylic ring having 1-2 heteroatoms independently selected from nitrogen, oxygen, or sulphur. In some embodiments, $R^1$ is piperidinyl. In some embodiments, $R^1$ is optionally substituted piperidinyl. In some embodiments, $R^1$ is 1-methylpiperidin-4-yl. In some embodiments, $R^1$ is 4-hydroxypiperidin-1-yl.

In some embodiments, $R^1$ is an optionally substituted 5-6 membered monocyclic heteroaryl ring having 1-4 heteroatoms independently selected from nitrogen, oxygen, or sulphur. In some embodiments, $R^1$ is pyrazolyl. In some embodiments, $R^1$ is optionally substituted pyrazolyl. In some embodiments, $R^1$ is 1-methyl-1H-pyrazol-4-yl. In some embodiments, $R^1$ is 1,3-dimethyl-1H-pyrazol-5-yl. In some embodiments, $R^1$ is pyridinyl. In some embodiments, $R^1$ is optionally substituted pyridinyl. In some embodiments, $R^1$ is 6-methylpyridin-3-yl. In some embodiments, $R^1$ is 6-(diethylamino)-pyridin-3-yl. In some embodiments, $R^1$ is 6-(4-methylpiperazin-1-yl)-pyridin-3-yl. In some embodiments, $R^1$ is 6-morpholinopyridin-3-yl.

As defined above, each R is independently selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur.

In some embodiments, R is hydrogen. In some embodiments, R is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur.

In some embodiments, R is an optionally substituted $C_{1-6}$ aliphatic. In some embodiments, R is phenyl. In some embodiments, R is a 3-8 membered saturated or partially unsaturated carbocyclic ring. In some embodiments, R is a 4-7 membered heterocylic ring having 1-2 heteroatoms independently selected from nitrogen, oxygen, or sulphur. In some embodiments, R is a 5-6 membered monocyclic heteroaryl ring having 1-4 heteroatoms independently selected from nitrogen, oxygen, or sulphur.

As defined above, each of $R^2$ is selected from hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, $R^2$ is hydrogen. In other embodiments, $R^2$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, $R^2$ is an optionally substituted $C_{1-6}$ aliphatic. In some embodiments, $R^2$ is methyl. In some embodiments, $R^2$ is optionally substituted methyl. In some embodiments, $R^2$ is ethyl. In some embodiments, $R^2$ is optionally substituted ethyl.

In some embodiments, $R^2$ is phenyl. In some embodiments, $R^2$ is optionally substituted phenyl.

In some embodiments, $R^2$ is an optionally substituted a 3-8 membered saturated or partially unsaturated carbocyclic ring. In some embodiments, $R^2$ is cyclopropyl. In some embodiments, $R^2$ is optionally substituted cyclopropyl. In some embodiments, $R^2$ is cyclopentyl. In some embodiments, $R^2$ is optionally substituted cyclopentyl.

As defined above, each of $R^3$ is selected from hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, $R^3$ is hydrogen. In other embodiments, $R^3$ is an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, $R^3$ is an optionally substituted $C_{1-6}$ aliphatic.

In some embodiments, $R^3$ is phenyl. In some embodiments, $R^3$ is optionally substituted phenyl. In some embodiments, $R^3$ is

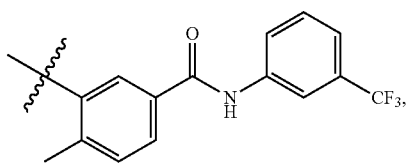 [SMILES: *c1cc(C(=O)Nc2cccc(C(F)(F)F)c2)ccc1C]

wherein

indicates the point of attachment. In some embodiments, R³ is

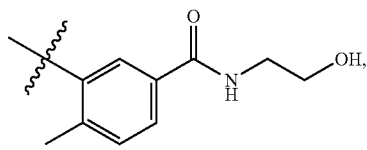 [SMILES: *c1cc(C(=O)NCCO)ccc1C]

wherein

indicates the point of attachment. In some embodiments, R³ is

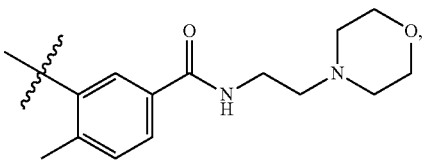 [SMILES: *c1cc(C(=O)NCCN2CCOCC2)ccc1C]

wherein

indicates the point of attachment. In some embodiments, R³ is

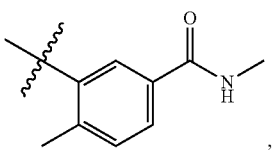 [SMILES: *c1cc(C(=O)NC)ccc1C]

wherein indicates the point of attachment. In some embodiments, R³ is

wherein

indicates the point of attachment. In some embodiments, R³ is

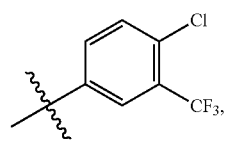 [SMILES: *c1ccc(Cl)c(C(F)(F)F)c1]

wherein

indicates the point of attachment. In some embodiments, R³ is

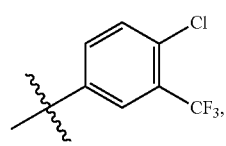 [SMILES: *c1ccc(Cl)c(C(F)(F)F)c1]

wherein

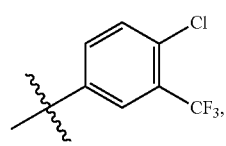 [SMILES: *c1ccc(Cl)c(C(F)(F)F)c1]

indicates the point of attachment. In some embodiments, R³ is

wherein

indicates the point of attachment. In some embodiments, $R^3$ is

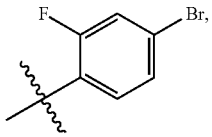 [SMILES: *c1ccc(Br)cc1F]

wherein

indicates the point of attachment. In some embodiments, $R^3$ is

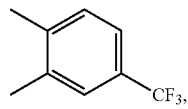

wherein

indicates the point of attachment. In some embodiments, $R^3$ is

wherein

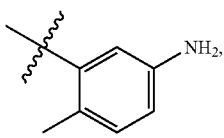 [SMILES: *c1cc(N)ccc1C]

indicates the point of attachment. In some embodiments, $R^3$ is

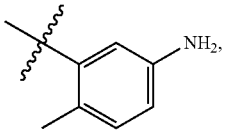 [SMILES: *c1cc(N)ccc1C]

wherein

indicates the point of attachment.

As defined above, each of $R^4$ and $R^5$ is independently selected from hydrogen or $C_{1-3}$ aliphatic, or $R^4$ and $R^5$ are taken together with their intervening atoms to form a 3-6 membered saturated carbocyclic ring.

In some embodiments, $R^4$ is hydrogen. In some embodiments, $R^4$ is $C_{1-3}$ aliphatic.

In some embodiments, $R^5$ is hydrogen. In some embodiments, $R^5$ is $C_{1-3}$ aliphatic.

In some embodiments, $R^4$ and $R^5$ are taken together with their intervening atoms to form a 3-6 membered saturated carbocyclic ring.

As defined above, each of $R^6$ and $R^7$ is independently hydrogen or optionally substituted $C_{1-6}$ aliphatic.

In some embodiments, $R^6$ is hydrogen. In other embodiments, $R^6$ is optionally substituted $C_{1-6}$ aliphatic.

In some embodiments, $R^7$ is hydrogen. In other embodiments, $R^7$ is optionally substituted $C_{1-6}$ aliphatic.

In some embodiments, the present invention provides a compound of any one of formulae IA, IB, ID, or ID.

In some embodiments, the present invention provides a compound of formula IA:

IA

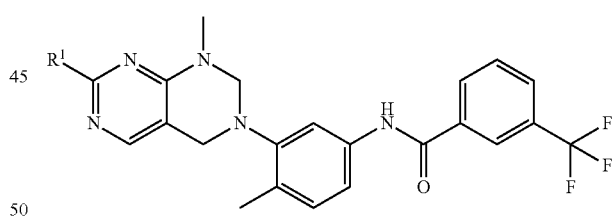

or a pharmaceutically acceptable salt thereof, wherein:
$R^1$ is selected from hydrogen, —OR, —SR, —N(R)$_2$, or an optionally substituted group selected from $C_{1-6}$ aliphatic, phenyl, a 3-8 membered saturated or partially unsaturated carbocylic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur; and each R is independently selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur.

In some embodiments, the present invention provides a compound of formula IB:

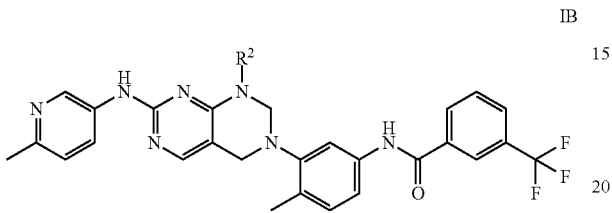

IB or a pharmaceutically acceptable salt thereof, wherein:

$R^2$ is selected from hydrogen, an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulphur.

In some embodiments, the present invention provides a compound of formula IC:

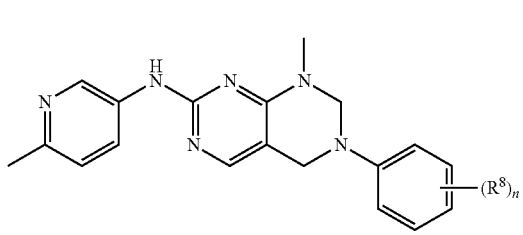

IC or a pharmaceutically acceptable salt thereof, wherein:
n is 0-4;
each $R^8$ is independently selected from hydrogen, —C(O)NR$_2$, —N(R)C(O)R, or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur; and each R is independently selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur.

In some embodiments, the present invention provides a compound of formula ID:

I-D or a pharmaceutically acceptable salt thereof, wherein:
n is 0-4;
$R^9$ is selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur;

each $R^{10}$ is independently selected from hydrogen, halogen, —N(R)$_2$ or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur; and each R is independently selected from hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulphur.

In some embodiments, present invention provides a compound of formula I selected from these depicted in Table 1, below.

TABLE 1
Representative Compounds of Formula I
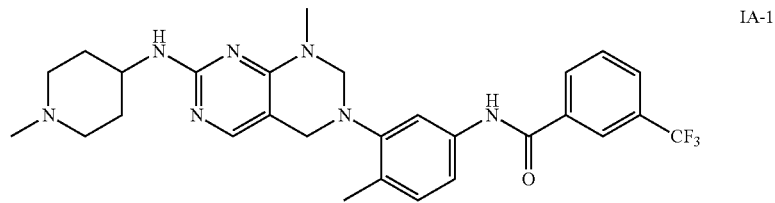
IA-1
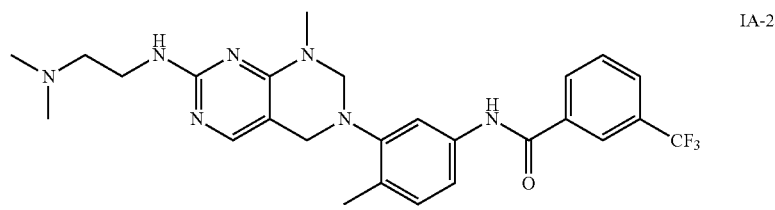
IA-2
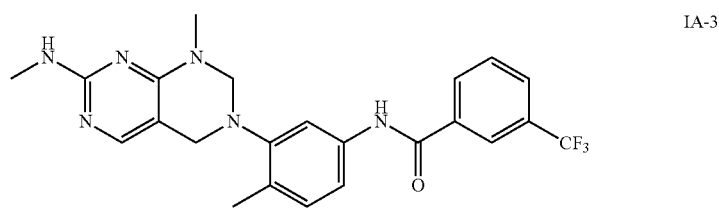
IA-3
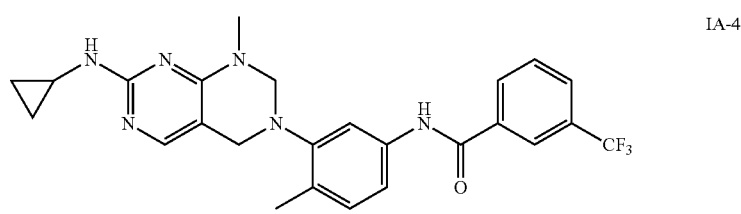
IA-4
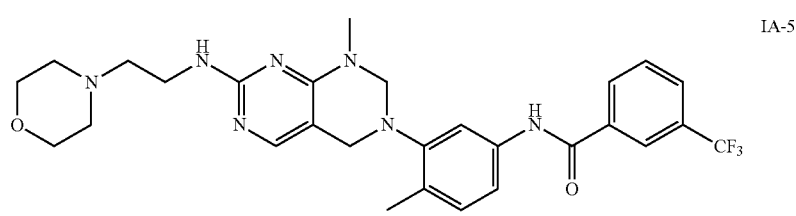
IA-5
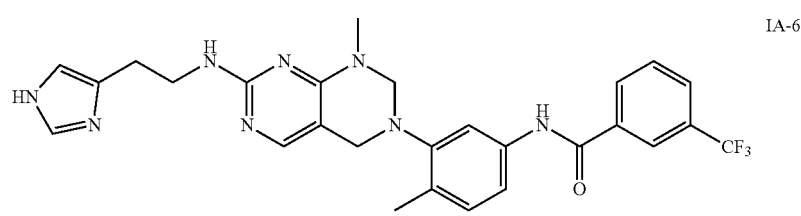
IA-6
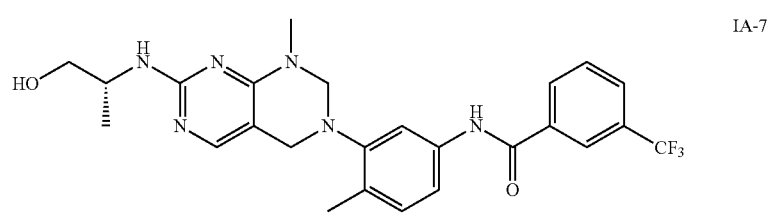
IA-7

TABLE 1-continued
Representative Compounds of Formula I
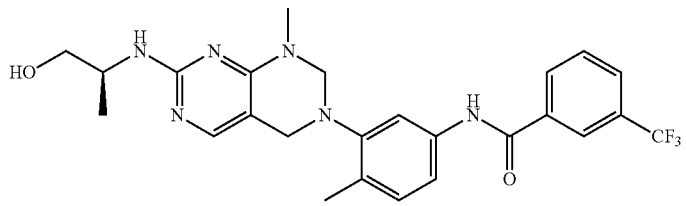 [SMILES: Cc1ccc(NC(=O)c2cccc(C(F)(F)F)c2)cc1N1Cc2cnc(N[C@@H](C)CO)nc2N(C)C1]
IA-8
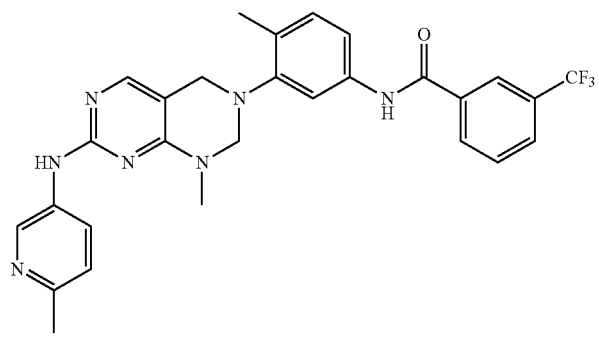 [SMILES: Cc1ccc(Nc2ncc3c(n2)N(C)CN(c2cc(NC(=O)c4cccc(C(F)(F)F)c4)ccc2C)C3)cn1]
IA-9
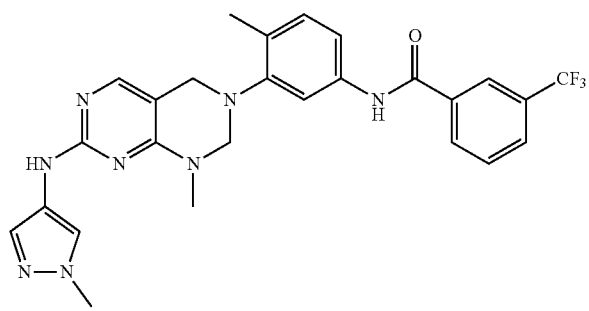 [SMILES: Cc1ccc(NC(=O)c2cccc(C(F)(F)F)c2)cc1N1Cc2cnc(Nc3cnn(C)c3)nc2N(C)C1]
IA-10
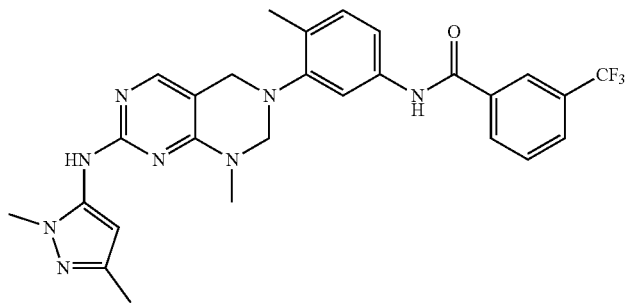 [SMILES: Cc1cc(Nc2ncc3c(n2)N(C)CN(c2cc(NC(=O)c4cccc(C(F)(F)F)c4)ccc2C)C3)n(C)n1]
IA-11
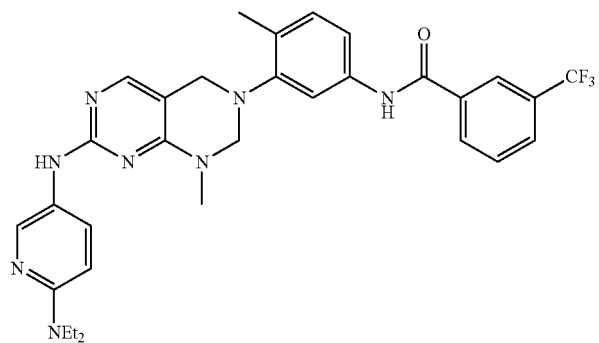
IA-12

TABLE 1-continued
Representative Compounds of Formula I
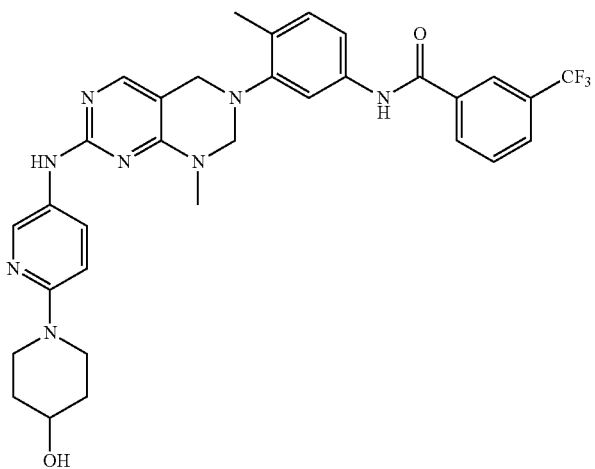 [SMILES: Cc1ccc(NC(=O)c2cccc(C(F)(F)F)c2)cc1N1Cc2cnc(Nc3ccc(N4CCC(O)CC4)nc3)nc2N(C)C1]
IA-13
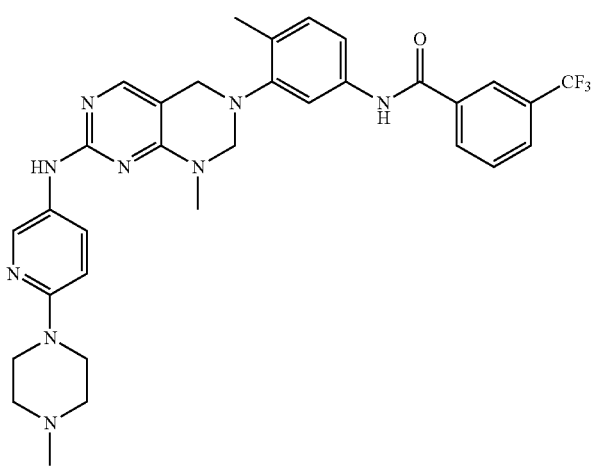 [SMILES: Cc1ccc(NC(=O)c2cccc(C(F)(F)F)c2)cc1N1Cc2cnc(Nc3ccc(N4CCN(C)CC4)nc3)nc2N(C)C1]
IA-14
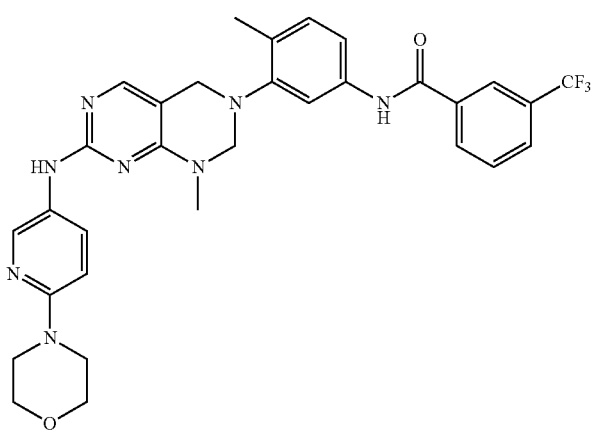 [SMILES: Cc1ccc(NC(=O)c2cccc(C(F)(F)F)c2)cc1N1Cc2cnc(Nc3ccc(N4CCOCC4)nc3)nc2N(C)C1]
IA-15

TABLE 1-continued
Representative Compounds of Formula I
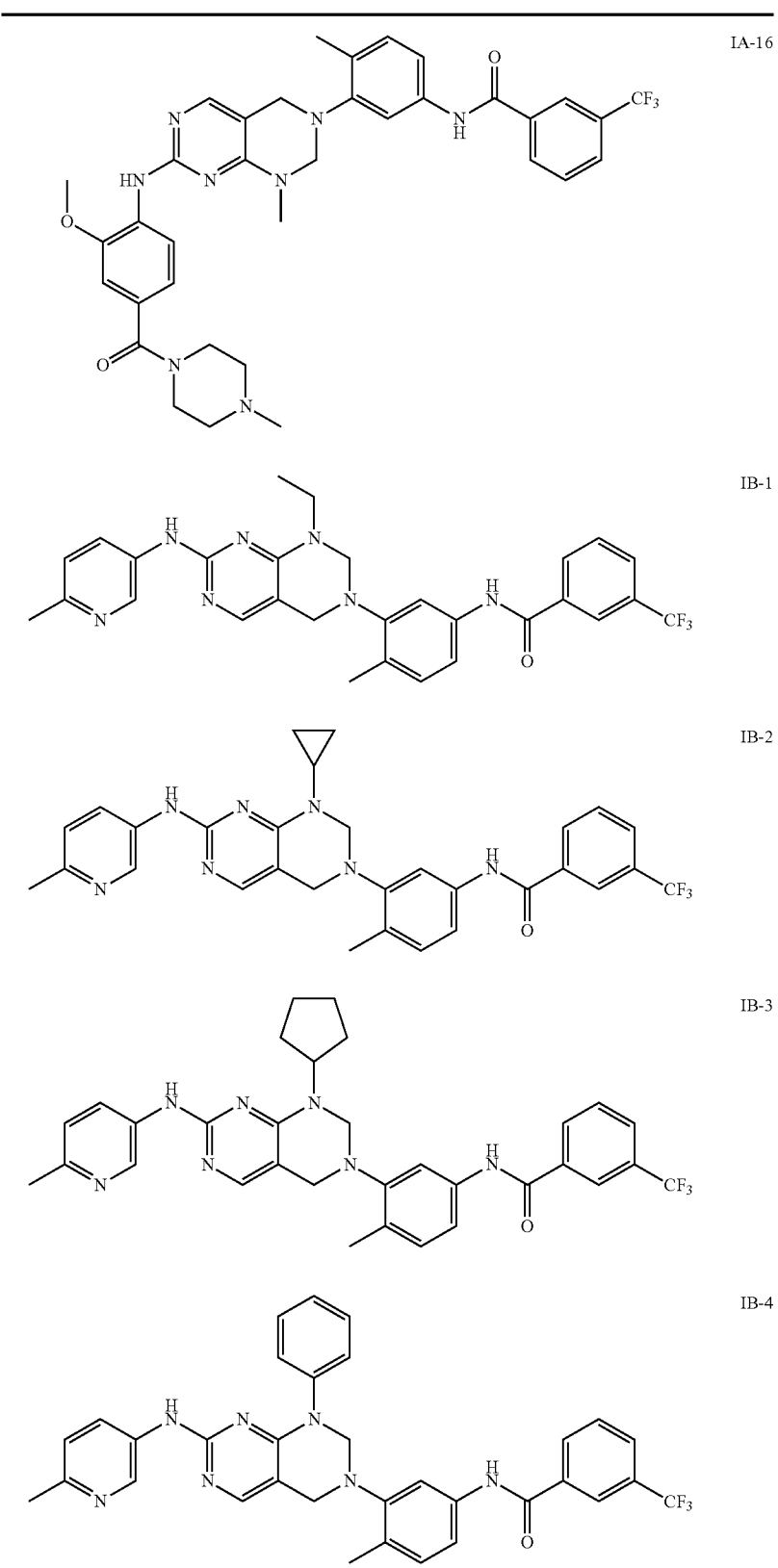
IA-16
IB-1
IB-2
IB-3
IB-4

TABLE 1-continued
Representative Compounds of Formula I
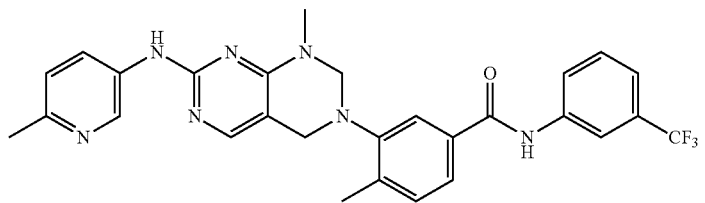 [SMILES: Cc1ccc(Nc2ncc3c(n2)N(C)CN(c2cc(C(=O)Nc4cccc(C(F)(F)F)c4)ccc2C)C3)cn1]
IC-1
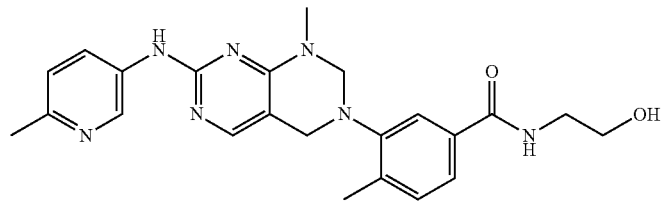 [SMILES: Cc1ccc(Nc2ncc3c(n2)N(C)CN(c2cc(C(=O)NCCO)ccc2C)C3)cn1]
IC-2
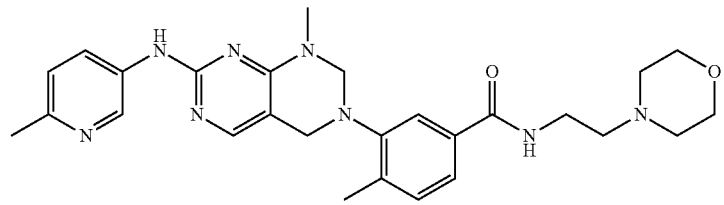 [SMILES: Cc1ccc(Nc2ncc3c(n2)N(C)CN(c2cc(C(=O)NCCN4CCOCC4)ccc2C)C3)cn1]
IC-3
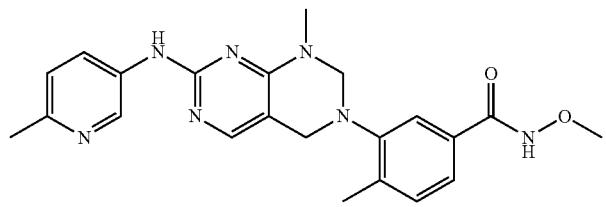
IC-4
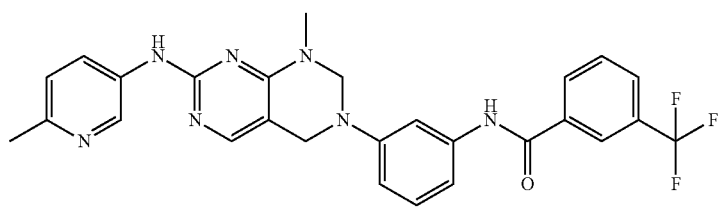 [SMILES: Cc1ccc(Nc2ncc3c(n2)N(C)CN(c2cccc(NC(=O)c4cccc(C(F)(F)F)c4)c2)C3)cn1]
IC-5
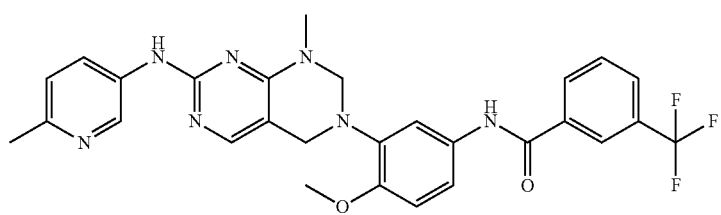 [SMILES: COc1ccc(NC(=O)c2cccc(C(F)(F)F)c2)cc1N1Cc2cnc(Nc3ccc(C)nc3)nc2N(C)C1]
IC-6

TABLE 1-continued
Representative Compounds of Formula I
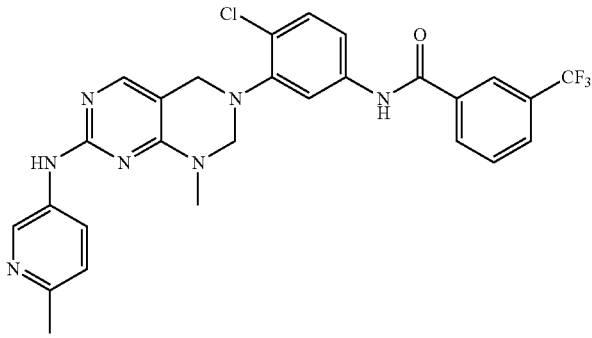
IC-7
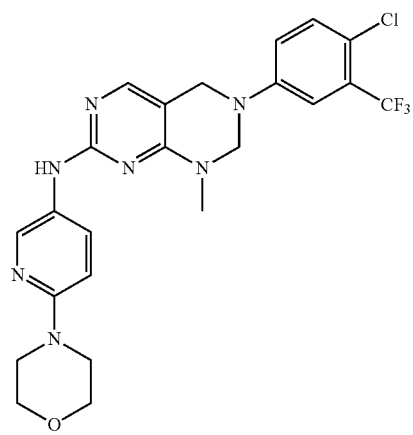
ID-1
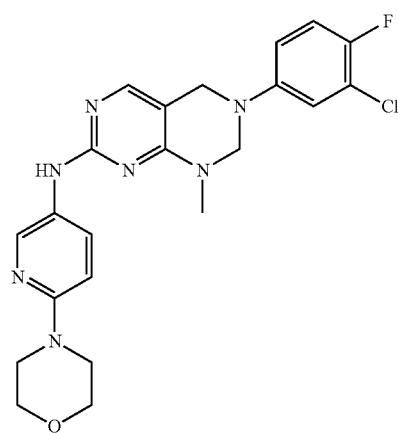
ID-2

TABLE 1-continued
Representative Compounds of Formula I
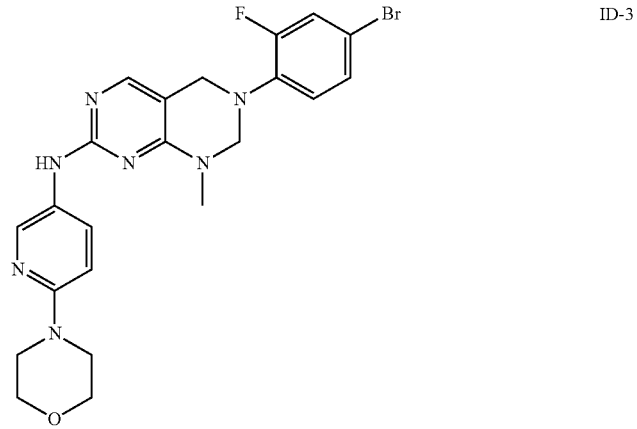
ID-3
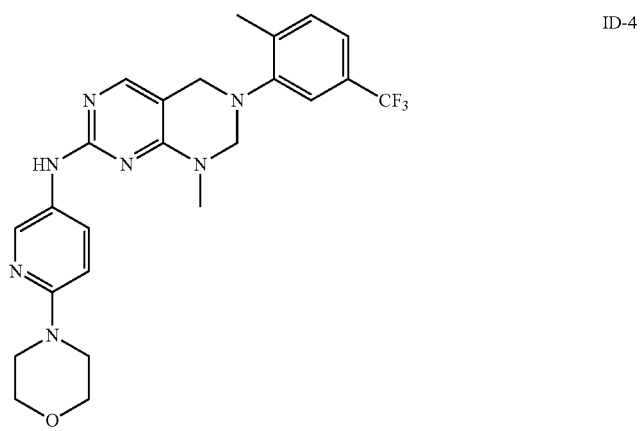
ID-4
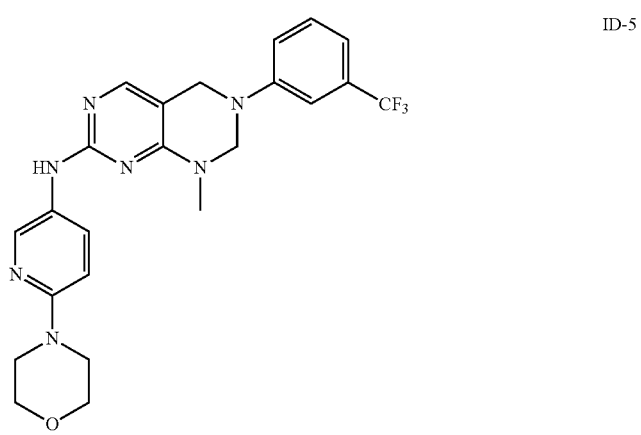
ID-5
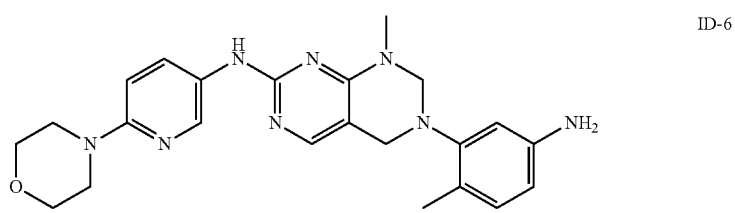
ID-6

4. Uses of Compounds and/or Compositions Thereof

As described herein, in some embodiments, compounds of formula I may be useful, for example, in any of a variety of assays, syntheses, and/or treatments (e.g., of kinase-associated diseases, disorders, or conditions.

Kinase-Associated Diseases, Disorders and Conditions

Protein kinases are a large multigene family consisting of more than 500 proteins. Without wishing to be bound by any particular theory kinases can play a prominent role in the development and therefore treatment of a number of human diseases in oncology, neurology and immunology. Kinase function is tightly regulated. In some embodiments kinases can lead to proliferative disorders and/or malignancy due to, among other things, mutation, overexpression, activation (e.g., over-activation), or repression of activity.

In some embodiments, therapeutic interventions for cancer are targeted to, among other things, inhibit protein kinase expression or activity. In some embodiments therapeutic interventions for cancer are targeted to, among other things, proteins that can regulate the expression or activity of kinases. In some embodiments proteins that can regulate the expression or activity of kinases can be, among other things, receptors or enzymes.

In some embodiments treatment of malignancies with protein kinase inhibitors can give rise to mutations. In some embodiments mutations can result in resistance to treatment. In some embodiments mutations can arise in a protein kinase targeted by a therapeutic. In some embodiments mutations can arise in protein kinases in a signaling pathway of a targeted kinase. Among other things the present invention recognizes a need for additional therapeutic options including therapeutics treating those cancers that have developed resistance to a therapeutic.

Receptor Tyrosine Kinases

Receptor tyrosine kinases (RTKs) are a class of protein kinases. RTKs are cell surface receptors for, among other things, growth factors, cytokines, and hormones. In some embodiments, RTKs can regulate normal cellular processes. In some embodiments, RTKs can play a role in development and progression of many types of cancer. Among others, the families of RTKs can include but are not limited to epidermal growth factor receptor (EGFR), fibroblast growth factor receptor (FGFR), vascular endothelial growth factor receptor (VEGFR), stem cell growth factor receptor (SCFR), rearranged during transfection (RET) receptor, FMS-Related Tyrosine Kinase (e.g., FLT3), Ephrin receptor (Eph), and discoidin domain receptor (DDR). In some embodiments, compounds, compositions and/or methods of the present disclosure target RTKs.

EGFR

In some particular embodiments compounds, compositions and/or methods of the present disclosure target epidermal growth factor receptor (EGFR). EGFR can form an homodimer. In some embodiments, EGFR dimerization stimulates its intrinsic protein-tyrosine kinases activity. Without wishing to be bound by any particular theory, it is proposed that, in some embodiments, one or more compounds of formula I may inhibit EGFR dimerization. Mutations that lead to EGFR overexpression or overactivity have been associated with a number of cancers. In some embodiments, one or more compounds of formula I may inhibit EGFR associated with such mutations. In some embodiments, one or more compounds of formula I specifically inhibits EGFR associated with such mutations (e.g., relative to its/their effect(s) on EGFR in the absence of such mutations.

Eph

In some embodiments compounds, compositions and/or methods of the present disclosure target members of the Ephrin (Eph) subfamily of RTKs. In some embodiments kinases of the EphA class (e.g. EphA1, EphA2, EphA3, EphA4, EphA5, EphA6, EphA7, EphA8, EphA9, EphA10) and/or kinases of the EphB class (e.g. EphB1, EphB2, EphB3, EphB4, EphB5, EphB6) are targeted. Binding of an ephrin ligand to the extracellular globular domain of an Eph family receptor, tyrosine and serine residues in the juxtamembrane region of the Eph become phosphorylated allowing the intracellular tyrosine kinase to convert into its active form and subsequently activate or repress downstream signaling cascades. In some embodiments, Eph family kinases are involved in segmentation, aconguidance, cell migration, angiogenesis, and limb development. Mutations that lead to Eph overexpression or overactivity have been associated with a number of cancers.

FLT3

In some embodiments, compounds, compositions and/or methods of the present disclosure target FLT3 kinase. FLT3 is a receptor tyrosine kinase; certain FLT3 activating mutations have been shown to be associated with one or more kinase-associated diseases, disorders or conditions (e.g., leukemia). For example, are found in 30% human acute myeloid leukemia (AML). The present disclosure establishes that certain compound(s) of formula I (e.g., IA-9) effectively inhibits FLT3 transformation and suppresses growth of human AML cells harboring FLT3 mutation.

c-Kit

In some embodiments, compounds, compositions and/or methods of the present disclosure target Kit. In some embodiments, Kit is also referred to as c-Kit, mast/stem cell growth factor receptor (SCFR, or CD117). In some embodiments Kit binds to stem cell factor (SCF), also known as "steel factor" or "c-kit ligand". In some embodiments, when Kit binds to SCF it forms a dimer that activates its intrinsic tyrosine kinase activity, that in turn phosphorylates and activates signal transduction molecules that propagate a signal in the cell. In some embodiments, signalling through Kit plays a role in cell survival, proliferation, and differentiation. Mutations that lead to Kit overexpression or overactivity have been associated with a number of cancers.

RET

In some embodiments, compounds, compositions and/or methods of the present disclosure target RET. The RET gene encodes a RTK for members of the glial cell line-derived neurotrophic factor (GDNF) family of extracellular signalling molecules. Upon binding of GDNF ligand to a co-receptor two molecules or RET are brought together triggering trans-autophosphorylation of tyrosine residues within the tyrosine kinase domain of each RET molecule. Mutations that lead to RET overexpression or overactivity have been associated with a number of cancers.

TXK

In some embodiments, compounds, compositions and/or methods of the present disclosure target TXK. TXK is a member of the TEC family of non-receptor tyrosine kinases. In some embodiments, TXK is expressed in T-cells and is an important component of signaling pathways downstream of lymphocyte antigen receptor. Among other things, TXK is phosphorylated in response to T-cell receptor stimulation and can be activated by phosphorylation by Src family kinases. Mutations that lead to TXK overexpression or overactivity have been associated with a number of cancers.

BCR-ABL

In some embodiments, compounds, compositions and/or methods of the present disclosure target BCR-ABL kinase.

BCR-ABL is a protein generated by fusion of portions of the ABL1 kinase gene with portions of the breakpoint cluster region (BCR) gene. In some embodiments, this fusion results in a constitutively active ABL protein kinase. In some embodiments, treatment of cancer with agents directed at inhibition BCR-ABL protein kinase activity can lead to resistance to those agents highlighting the need for compounds, compositions and/or methods provided in this disclosure.

B-RAF

In some embodiments, compounds, compositions and/or methods of the present disclosure target B-RAF protein kinase. B-RAF is a member of the RAF kinase family of growth signal transduction protein kinases. This protein plays a role in regulating the MAP kinase/ERKs signaling pathway, which affects cell division, differentiation, and secretion. In some embodiments, B-RAF can cause cancer through mutants that are constitutively active. In some embodiments, treatment of cancer with agents directed at inhibition B-Raf protein kinase activity can lead to resistance to those agents highlighting the need for compounds, compositions and/or methods provided in this disclosure.

RAS

In some embodiments, compounds, compositions and/or methods of the present disclosure target RAS. In some embodiments, proteins that can regulate the activity of kinases can include members of the Ras superfamily. The Ras superfamily can include but is not limited to RAS, Rho, Ran, Rab and Arf. These family members share a common domain which provides GTPase and nucleotide exchange activity. In some embodiments the Ras protein subfamily includes KRAS, NRAS, and HRAS. In some embodiments, the Ras subfamily plays a role in regulation of cell proliferation. In some embodiments, mutations in Ras subfamily proteins can lead to constitutively active proteins. In some embodiments, the constitutive activity can lead to cancer. RAS oncogenic mutations, mostly KRAS and NRAS, are common in human cancers. In some embodiments since the enzymatic activity of RAS is used to turn itself off and its GTP binding affinity is very high, RAS proteins have been difficult to target. Identification of alternative means to block the RAS oncogenic signaling is useful for developing therapies against RAS-driven cancer.

Development of Resistance

It has been found that treatment of kinase-associated diseases disorders or conditions with protein kinase inhibitor therapy (e.g., via administration of protein kinase inhibitors) can lead to resistance. In some embodiments, this resistance can arise from mutations in kinases. Among other things the present invention recognizes a need for additional therapeutic options including therapeutics treating those cancers that have developed resistance to one or more therapeutic agents or modalities. In some embodiments, the present disclosure provides methods of treatment one or more kinase-associated diseases, disorders or conditions (e.g., cancer) by administration of a compound of formula I, or a composition thereof, to a subject or subjects who has/have developed and/or is/are at risk of developing, resistance to one or more other agents or modalities otherwise indicated for treatment of the disease, disorder or condition; in some such embodiments, such resistance is attributable to and/or otherwise associated with, one or more mutations that alters kinase level and/or activity (e.g., a kinase inhibited by the compound of formula I).

5. Compositions and Administration

In some embodiments, one or more compounds of formula I may be provided and/or utilized in accordance with the present invention as part of a composition, e.g., a pharmaceutically acceptable composition. In some particular embodiments, a composition comprising a compound of formula I is formulated for administration to an organism (e.g, and animal, a mammal, and most particularly, a human). In some embodiments, the organism is suffering from or susceptible to a kinase-associated disease, disorder or condition, e.g., as described herein.

In some embodiments, compounds and/or compositions may be administered in accordance with the present invention, using any amount and any route of administration effective for treating or lessening the severity of a kinase-associated disease, disorder or condition, e.g., as described herein. Those of ordinary skill in the art will appreciate that the exact amount required and/or otherwise administered (e.g., in any particular dose) may vary for different subjects and/or different diseases, disorders or conditions, in accordance with sound medical practice, for example taking into consideration features such as species, age, general condition, prior medical history (including prior received therapies), etc of the subject, identity of the particular agent being administered, particular mode of administration being utilized, any therapy being administered in combination with the agent, and the like.

In some embodiments, a compound of formula I may be formulated in a unit dosage form, for example for ease of administration and/or uniformity of dosage. The expression "unit dosage form" as used herein typically refers to a physically discrete unit for administration to a subject. It will be understood, that total daily dosage may be set by a medical practitioner, and may include more than one such discrete unit, and/or may utilize a fraction of a discrete unit. In some embodiments, compositions for administration are prepared as liquid formulations (e.g., for oral administration, parenteral administration, aerosol administration, etc). Liquid dosage forms, e.g., for oral administration, include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. A sterile injectable preparation may be or comprise a sterile injectable solution, suspension or emulsion, for example in a nontoxic, parenterally acceptable diluent or solvent, for example, as a solution in 1,3-butanediol. Among the acceptable vehicles and solvents that may be employed is such formulations include, but are not limited to, water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In some embodiments, it may be desirable to prolong one or more effects of a compound of the present invention. In some embodiments, it may be desirable, for example, to slow absorption of a compound from subcutaneous or intramuscular injection. In some embodiments, such slowing may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Exemplary compositions for rectal or vaginal administration may, for example, be formulated as suppositories. In some embodiments, such suppositories are prepared by mixing invention compound with one or more suitable non-irritating excipients or carriers, such as cocoa butter, polyethylene glycol or a suppository wax which are solid at ambient temperature but liquid at body temperature and therefore melt in the rectum or vaginal cavity and release the active compound.

Exemplary solid dosage forms for oral administration may include, for example, capsules, tablets, pills, powders, and granules. In such solid dosage forms, an active compound may be combined with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

In some embodiments, an active compound can be in micro-encapsulated form with one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms an active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Exemplary dosage forms for topical or transdermal administration may include, for example, ointments, pastes, creams, lotions, gels, powders, solutions, sprays, inhalants or patches. In some embodiments, an active component is admixed, for example under sterile conditions, with a pharmaceutically acceptable carrier and any needed preservatives or buffers as may be required.

Ophthalmic formulation, eardrops, and eye drops are also contemplated as being within the scope of this invention.

Alternatively or additionally, the present invention contemplates the use of transdermal patches, which have the added advantage of providing controlled delivery of a compound to the body.

Formulations for transdermal delivery may be prepared, for example, by dissolving or dispensing a compound in an appropriate medium. In some embodiments, one or more absorption enhancers can be used to increase flux of a compound across skin. In some embodiments, rate of transdermal progress can be controlled, for example, by either providing a rate controlling membrane or by dispersing compound in an appropriate polymer matrix or gel.

Those of ordinary skill in the art reading the present disclosure will appreciate that aspects and features described with respect to one embodiment of the present invention may be applied mutis mutandis to other embodiments, unless explicitly stated otherwise or clearly inapplicable from context.

In order that the invention described herein may be more fully understood, the following Examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

All features of each of the aspects of the invention apply to all other aspects mutatis mutandis.

Example 1

General Reaction Sequence for Compounds of Formula IA

Compounds of formula IA were synthesized according to Scheme 1. Exemplary methods are described further below.

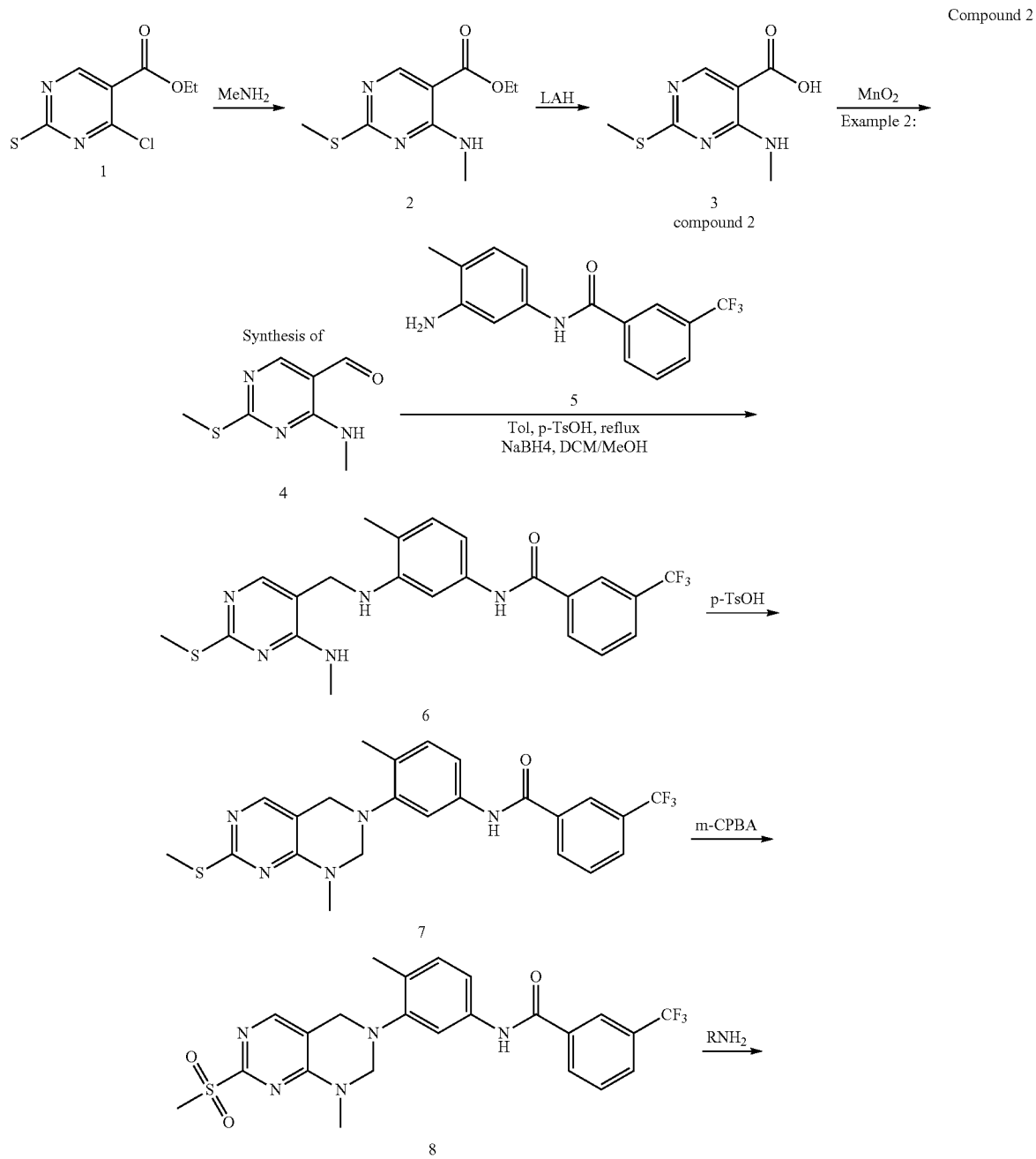

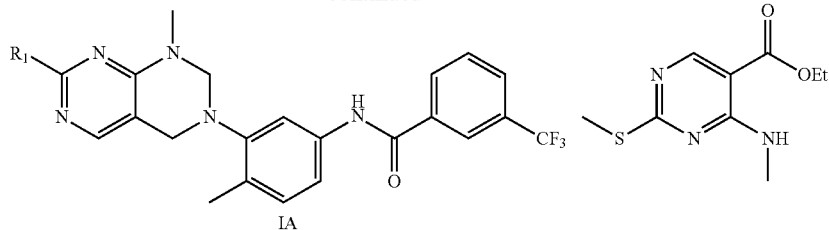

Ethyl 4-(methylamino)-2-(methylthio)pyrimidine-5-carboxylate

To a stirred solution of compound 1 (40 g, 172 mmol) in 500 mL of DCM 70 mL of a 23% solution of methylamine in ethanol at 0° C. was slowly added. The resulting mixture was stirred at 0° C. for 45 min. After compound 1 was completely consumed as monitored by TLC, 300 mL of water was added to the mixture. The organic layer was separated and washed with brine (2×200 mL), dried over anhydrous MgSO$_4$, filtered and evaporated to give 36.86 g of the desired product as a white solid. Yield: 94%.

Example 3

Synthesis of Compound 3

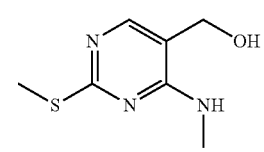

Compound 3

(4-(methylamino)-2-(methylthio)pyrimidin-5-yl)methanol

To a suspension of LAH (7.38 g, 194.6 mmol) in THF (dry, 800 mL) at 0° C. a solution of compound 2 (36.86 g, 162.2 mmol) in THF (200 mL) was added through a dropping funnel under N$_2$. The mixture was stirred at room temperature for 2 h. TLC indicated that compound 2 was completely consumed. To the reaction mixture water (8 mL), 15% NaOH (24 mL) and water (24 mL) were added. The organic layer was decanted and the solid was washed with EA (2×50 mL). All the organic layers were combined and washed with brine (100 mL), dried over MgSO$_4$, filtered and evaporated in reduced pressure. The resulting yellow solid (27 g) was recrystallized from EA/PE (1/1) to get 18.5 g of the desired product as a white solid. Yield: 62%. $^1$H NMR, 500 MHz (CDCl$_3$), 7.68 (s, 1H), 5.87 (bs, 1H), 4.50 (s, 1H), 3.04 (d, 3H, J=5.0 Hz), 2.52 (s, 3H), 1.67 (b, 3H).

Example 4

Synthesis of Compound 4

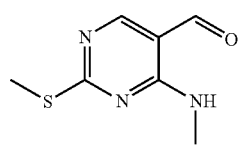

Compound 4

4-(methylamino)-2-(methylthio)pyrimidine-5-carbaldehyde

A suspension of compound 3 (18.3 g, 0.1 mol) and MnO$_2$ (86.9 g, 1 mol) in DCM (1 L) was stirred at room temperature for 16 h. TLC indicated that compound 3 was completely consumed. The reaction mixture was filtered through a pad of celite. The cake was washed with EA (50 mL). The filtrate and wash were combined and concentrated under reduced pressure to obtain 18.3 g of the desired product as a white solid. Yield: 89%

Example 5

Synthesis of Compound 6

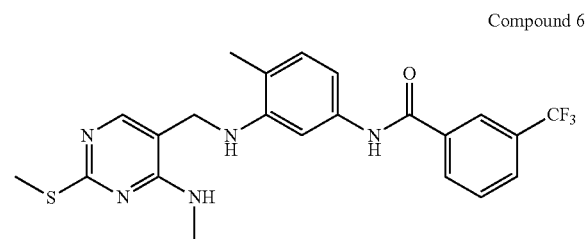

Compound 6

N-(4-methyl-3-(((4-(methylamino)-2-(methylthio)pyrimidin-5-yl)methyl)amino)phenyl)-3-(trifluoromethyl)benzamide To a mixture of compound 4 (1.83 g, 10 mmol) and compound 5 (2.94 g, 10 mmol) in toluene (20 mL) was added p-TsOH.H$_2$O (20 mg). The mixture was heated to reflux and the water formed was removed by Dean-Stark trap. After refluxing for 3 h, toluene was evaporated and thereto were added DCM (10 mL) and EtOH (10 mL). NaBH$_4$ (450 mg, 1.2 eq.) was added in one porting and the mixture was stirred overnight at room temperature. The reaction mixture was quenched with NH$_4$Cl, stirred for 0.5 h, extracted with DCM (3×50 mL). The extracts were combined, dried and evaporated. The resulting residue was purified by silica gel chromatography (PE/EA=1/1) to give 2.2 g of pure product as a yellow solid. Yield: 48%. $^1$H NMR, 500 MHz (DMSO-d$_6$), 10.18 (s, 1H), 8.20 (d, 2H, J=8.0 Hz), 7.93 (d, J=8.0 Hz, 1H), 7.83 (s, 1H), 4.50 (s, 1H), 7.75 (t, J=7.5 Hz, 1H), 7.11 (d, J=4.5 Hz, 1H), 7.03 (d, J=7.5 Hz, 1H), 6.85 (d, J=7.5 Hz, 2H), 5.44 (t, J=5.52 Hz, 1H), 4.09 (d, J=5.5 Hz, 2H), 2.90 (d, J=5.0 Hz, 3H), 2.40 (s, 3H), 2.10 (s, 3H).

Example 6

Synthesis of Compound 7

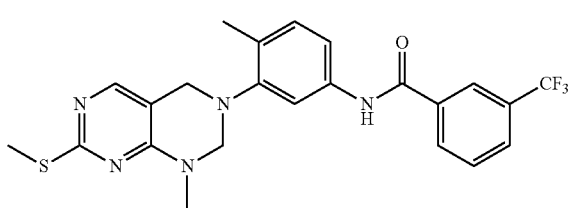

Compound 7

N-(4-methyl-3-(1-methyl-7-(methylthio)-1,4-dihydropyrimido[4,5-d]pyrimidin-3(2H)-yl)phenyl)-3-(trifluoromethyl)benzamide A mixture of compound 6 (231 mg, 1 mmol), paraformaldehyde (45 mg, 1.5 mmol, 3 eq.) and p-TsOH.H$_2$O (10 mg) in toluene (10 mL) was heated at 110° C. for 2 h. LCMS indicated that compound 6 was consumed completely. The reaction mixture was concentrated and purified by silica gel chromatography (PE/EA=2/1) to get 160 mg of the desired product as a white solid. Yield: 68%. $^1$H NMR, 500 MHz (CDCl$_3$), 8.12 (s, 1H), 8.05 (s, 1H), 7.99 (d, 1H, J=8.0 Hz), 7.76 (t, 1H, J=7.5 Hz), 7.59 (s, 1H), 7.57 (d, 1H, J=8.0 Hz), 7.32 (d, 1H, J=8.0 Hz), 7.27 (s, 1H), 7.19 (d, 1H, J=8.0 Hz), 4.57 (s, 2H), 4.19 (s, 2H), 3.13 (s, 3H), 2.48 (s, 3H), 2.34 (s, 3H).

Example 7

Synthesis of Compound 8

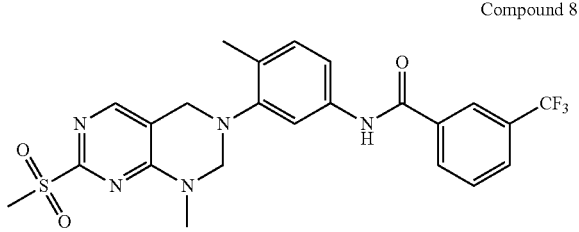

Compound 8

N-(4-methyl-3-(1-methyl-7-(methylsulfonyl)-1,4-dihydropyrimido[4,5-d]pyrimidin-3(2H)-yl)phenyl)-3-(trifluoromethyl)benzamide A mixture of compound 7 (473 mg, 1 mmol) and m-CPBA (500 mg, 2.2 mmol) in DCM (25 mL) was stirred overnight at room temperature. The mixture was diluted with 25 mL of DCM, washed with aqueous NaHCO$_3$ (3×50 mL), dried and concentrated. The resulting residue was purified by silica gel chromatography to get 225 mg of the desired product as a pale yellow solid. Yield: 45%. $^1$H NMR, 500 MHz (CDCl$_3$), 8.17 (s, 1H), 8.06 (s, 1H), 8.01 (d, 1H, J=8.0 Hz), 7.82 (s, 1H), 7.76 (d, 1H, J=7.5 Hz), 7.58 (t, 1H, J=8.0 Hz), 7.30 (s, 1H), 7.28 (s, 1H), 7.20 (d, 1H, J=8.0 Hz), 4.68 (s, 2H), 4.28 (s, 2H), 3.23 (s, 3H), 3.20 (s, 3H), 2.35 (s, 3H).

Example 8

General Procedure for Aliphatic Amines of Formula IA

To a solution of compound 8 (101 mg, 0.2 mmol) in dioxane (10 mL) 10 eq. of the aliphatic amine at room temperature was added, the mixture was sealed and stirred at 120° C. overnight. The solvent was evaporated by rotary evaporator and the resulting residue was subjected to preparative HPLC (basic condition) to get the desired target.

Example 9

Synthesis of IA-1

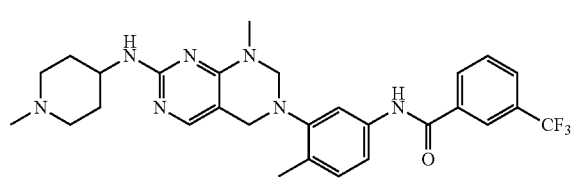

IA-1

N-(4-methyl-3-(1-methyl-7-((1-methylpiperidin-4-yl)amino)-1,4-dihydropyrimido[4,5-d]pyrimidin-3(2H)-yl)phenyl)-3-(trifluoromethyl)benzamide Followed the procedures as described in Example 8, starting with compound 8 (101 mg, 0.2 mmol), compound IA-1 was obtained as a white solid (26 mg, 24%). MS (ESI) m/z: 540.3 [M+H]$^+$. $^1$H NMR, 500 MHz (DMSO-d$_6$) δ 10.36 (s, 1H), 8.20 (m, 2H), 7.95 (d, 1H, J=7.6 Hz), 7.76 (m, 1H), 7.51 (s, 1H), 7.47 (s, 1H), 7.34 (d, 1H, J=8.2 Hz), 7.15 (d, 1H, J=8.2 Hz), 6.14 (s, 1H), 4.53 (s, 2H), 4.11 (s, 2H), 3.57 (s, 1H), 3.05 (s, 3H), 2.68 (d, 2H,), 2.28 (s, 3H), 2.12 (s, 3H), 1.89 (m, 2H), 1.77 (d, 2H, J=13.4 Hz), 1.42 (m, 2H).

Example 10

Synthesis of IA-2

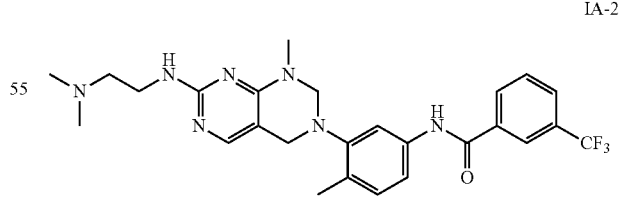

IA-2

N-(3-(7-((2-(dimethylamino)ethyl)amino)-1-methyl-1,4-dihydropyrimido[4,5-d]pyrimidin-3(2H)-yl)-4-methylphenyl)-3-(trifluoromethyl)benzamide Following the procedures as described in Example 8, starting with compound 8 (101 mg, 0.2 mmol), IA-2 was obtained as a white solid (40 mg, 39%). MS (ESI) m/z: 514.2 [M+H]+. 1H NMR, 500 MHz (DMSO-d6), 10.36 (s, 1H), 8.21 (m, 2H), 7.94 (d, 1H, J=7.9 Hz), 7.76 (m, 1H), 7.51 (s, 1H), 7.48 (s, 1H), 7.35 (d, 1H, J=8.2 Hz), 7.15 (d, 1H, J=8.3 Hz), 6.06 (s, 1H), 4.54 (s, 2H), 4.11 (s, 2H), 3.27 (m, 2H), 3.06 (s, 3H), 2.34 (m, 2H), 2.28 (s, 3H), 2.13 (s, 6H).

Example 11

Synthesis of IA-3

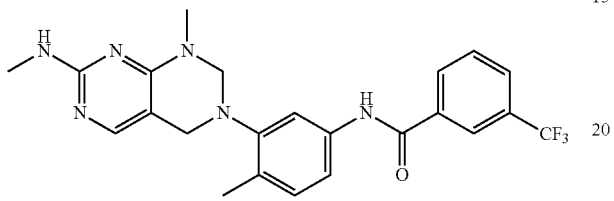

IA-3

N-(4-methyl-3-(1-methyl-7-(methylamino)-1,4-dihydropyrimido[4,5-d]pyrimidin-3(2H)-yl)phenyl)-3-(trifluoromethyl)benzamide Following the procedures as described in Example 8, starting with compound 8 (101 mg, 0.2 mmol), IA-3 was obtained as a white solid (30 mg, 33%). MS (ESI) m/z: 457.3 [M+H]+. 1H NMR, 500 MHz (DMSO-d6), 8.10 (s, 1H), 8.02 (d, 1H, J=7.0 Hz), 7.80 (d, 1H, J=7.0 Hz), 7.72 (s, 1H), 7.62 (t, 1H, J=8.5 Hz), 7.53 (s, 1H), 7.25-7.28 (m, 2H), 7.19 (d, 1H, J=8.0 Hz), 4.71 (bs, 1H), 4.54 (s, 2H), 4.16 (s, 2H), 3.13 (s, 3H), 2.93 (d, 3H), 2.34 (s, 3H).

Example 12

Synthesis of IA-4

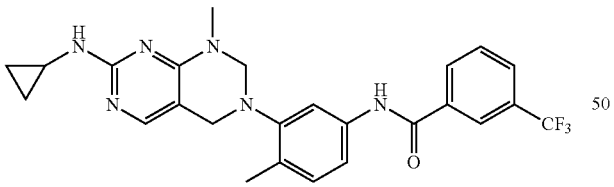

IA-4

N-(3-(7-(cyclopropylamino)-1-methyl-1,4-dihydropyrimido[4,5-d]pyrimidin-3(2H)-yl)-4-methylphenyl)-3-(trifluoromethyl)benzamide Following the procedures as described in Example 8, starting with compound 8 (101 mg, 0.2 mmol), IA-4 was obtained as a white solid (54 mg, 56%). MS (ESI) m/z: 483.3 [M+H]+. 1H NMR, 500 MHz (DMSO-d6), 10.37 (s, 1H), 8.21 (m, 2H), 7.79 (d, 1H, J=7.9 Hz), 7.76 (m, 1H), 7.51 (s, 2H), 7.36 (d, 1H, J=8.1 Hz), 7.16 (d, 1H, J=8.2 Hz), 6.53 (d, 1H, J=3.5 Hz), 4.54 (s, 2H), 4.13 (s, 2H), 3.07 (m, 3H), 2.64 (t, 1H), 2.29 (m, 3H), 0.56 (m, 2H), 0.38 (m, 2H).

Example 13

Synthesis of IA-5

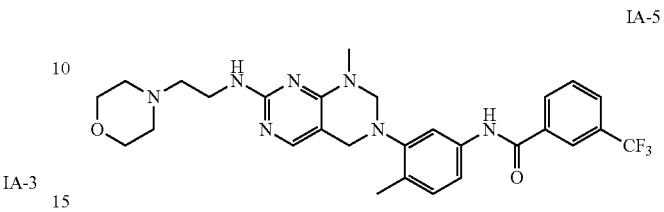

IA-5

N-(4-methyl-3-(1-methyl-7-((2-morpholinoethyl)amino)-1,4-dihydropyrimido[4,5-d]pyrimidin-3(2H)-yl)phenyl)-3-(trifluoromethyl)benzamide Following the procedures as described in Example 8, starting with compound 8 (101 mg, 0.2 mmol), IA-5 was obtained as a white solid (65 mg, 58%). MS (ESI) m/z: 556.3 [M+H]+. 1H NMR, 500 MHz (DMSO-d6), 10.36 (s, 1H), 8.21 (m, 2H), 7.74 (d, 1H, J=7.8 Hz), 7.76 (m, 1H), 7.52 (s, 1H), 7.47 (s, 1H), 7.34 (d, 1H, J=9.8 Hz), 7.16 (d, 1H, J=8.2 Hz), 6.12 (s, 1H), 4.54 (s, 2H), 4.11 (s, 2H), 3.54 (m, 4H), 3.29 (m, 2H), 3.06 (m, 3H), 2.41 (m, 2H), 2.36 (s, 4H), 2.28 (s, 3H).

Example 14

Synthesis of IA-6

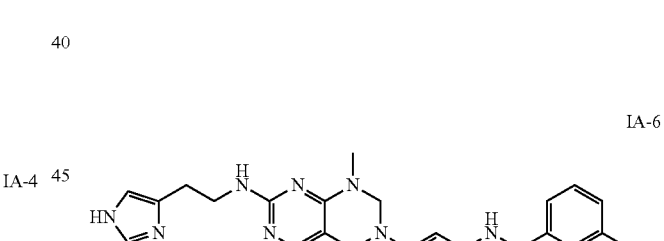

IA-6

N-(3-(7-((2-(1H-imidazol-4-yl)ethyl)amino)-1-methyl-1,4-dihydropyrimido[4,5-d]pyrimidin-3(2H)-yl)-4-methylphenyl)-3-(trifluoromethyl)benzamide Following the procedures as described in Example 8, starting with compound 8 (101 mg, 0.2 mmol), IA-6 was obtained as a white solid (40 mg, 37%). MS (ESI) m/z: 537.3 [M+H]+. 1H NMR, 500 MHz (DMSO-d6), 11.78 (s, 1H), 10.39 (s, 1H), 8.21 (m, 2H), 7.94 (d, 1H, J=7.9 Hz), 7.76 (m, 1H), 7.49 (s, 3H), 7.37 (d, 1H, J=7.8 Hz), 7.15 (d, 1H, J=8.3 Hz), 6.83 (s, 1H), 6.34 (s, 1H), 4.54 (s, 2H), 4.12 (s, 2H), 3.41 (m, 2H), 3.06 (s, 3H), 2.68 (s, 2H), 2.268 (s, 3H).

Example 15

Synthesis of IA-7

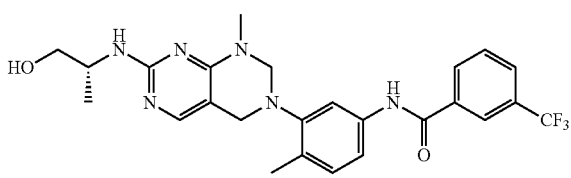

IA-7

(R)—N-(3-(7-((1-hydroxypropan-2-yl)amino)-1-methyl-1,4-dihydropyrimido[4,5-d]pyrimidin-3(2H)-yl)-4-methylphenyl)-3-(trifluoromethyl)benzamide Following the procedures as described in Example 8, starting with compound 8 (101 mg, 0.2 mmol), IA-7 was obtained as a white solid (22 mg, 22%). MS (ESI) m/z: 501.2 [M+H]$^+$. $^1$H NMR, 500 MHz (DMSO-d$_6$), 10.37 (s, 1H), 8.22 (m, 2H), 7.94 (d, 1H, J=7.8 Hz), 7.76 (m, 1H), 7.51 (s, 1H), 7.48 (s, 1H), 7.35 (d, 1H, J=8.1 Hz), 7.15 (d, 1H, J=8.2 Hz), 5.91 (d, 1H, J=7.9 Hz), 4.63 (m, 1H), 4.54 (s, 2H), 4.11 (s, 2H), 3.88 (t, 1H), 3.42 (t, 1H), 3.25 (t, 1H), 3.06 (s, 3H), 2.28 (s, 3H), 1.06 (d, 3H, J=6.6 Hz).

Example 16

Synthesis of IA-8

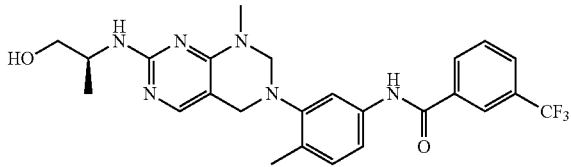

IA-8

(S)—N-(3-(7-((1-hydroxypropan-2-yl)amino)-1-methyl-1,4-dihydropyrimido[4,5-d]pyrimidin-3(2H)-yl)-4-methylphenyl)-3-(trifluoromethyl)benzamide Following the procedures as described in Example 8, starting with Compound 8 (101 mg, 0.2 mmol), IA-8 was obtained as a white solid (41 mg, 41%). MS (ESI) m/z: 501.2 [M+H]$^+$. $^1$H NMR, 500 MHz (DMSO-d$_6$), 10.37 (s, 1H), 8.21 (m, 2H), 7.94 (d, 1H, J=7.7 Hz), 7.76 (m, 1H), 7.51 (s, 1H), 7.48 (s, 1H), 7.35 (d, 1H, J=8.2 Hz), 7.15 (d, 1H, J=8.2 Hz), 5.92 (d, 1H, J=8.0 Hz), 4.63 (m, 1H), 4.54 (s, 2H), 4.11 (s, 2H), 3.88 (t, 1H), 3.42 (t, 1H), 3.24 (t, 1H), 3.06 (s, 3H), 2.28 (s, 3H), 1.06 (d, 3H, J=6.6 Hz).

Example 17

General Reaction Sequence for Aniline Compounds of Formula IA

The formylated amine intermediate was prepared as described below:

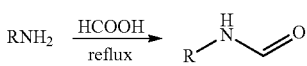

The amine was refluxed in HCOOH for 8-12 h before it was evaporated by rotary evaporator. The resulting residue was purified by reverse HPLC (0.1% NH$_3$ solution as A and MeCN as B) and lyophilized to get the formylated amine.

An alternative preparation is described below:

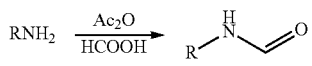

To a round bottom flask at room temperature containing formic acid (2 mL) acetic anhydride (1 mL) was added dropwise. The reaction was stirred for 45 min. followed by the dropwise addition of a solution of aniline (0.3 g) in THF (1 mL). The reaction mixture was evaporated under reduced pressure and further purified by reverse HPLC (0.1% NH$_3$ solution as A and MeCN as B) and lyophilized to get the formylated amine.

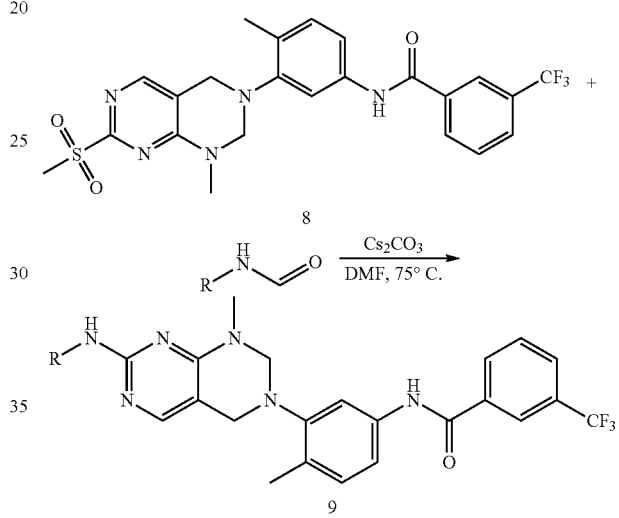

Compound 8 (110 mg, 0.2 mmol), 1 eq. of formylated amine and Cs$_2$CO$_3$ (80 mg) in DMF (dry, 3 mL) were heated at 75° C. under N$_2$ for 18 h. The solid was filtered off and the filtrate was purified by preparative HPLC to get the final product.

Example 18

Synthesis of Compound IA-9

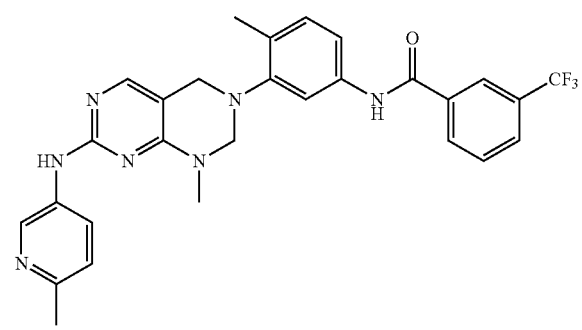

IA-9

N-(4-methyl-3-(1-methyl-7-((6-methylpyridin-3-yl)amino)-1,4-dihydropyrimido[4,5-d]pyrimidin-3(2H)-yl)phenyl)-3-(trifluoromethyl)benzamide Following the procedure described in Example 17, compound IA-9 was obtained (47 mg, 38% yield) ESI for C$_{28}$H$_{26}$F$_3$N$_7$O (M+1)$^+$: 534.2. $^1$H NMR (400 MHz, DMSO-d$_6$): δ 10.41 (s, 1H), 10.33 (brs, 1H), 8.96 (s, 1H), 8.20 (m, 3H), 7.96 (dd, J=6.8, 1.6 Hz, 1H), 7.76 (m, 2H), 7.62 (s, 1H), 7.56 (m, 1H), 7.31 (d, J=8.0 Hz, 1H), 7.20 (d, J=8.0 Hz, 1H), 4.80 (s, 2H), 4.28 (s, 2H), 3.24 (s, 3H), 2.55 (s, 3H), 2.31 (s, 3H).

Example 19

Synthesis of Compound IA-10

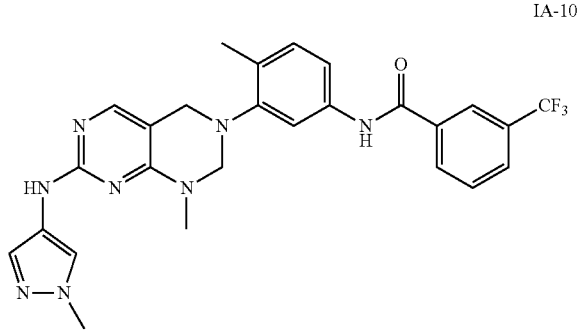

N-(4-methyl-3-(1-methyl-7-((1-methyl-1H-pyrazol-4-yl)amino)-1,4-dihydropyrimido[4,5-d]pyrimidin-3(2H)-yl)phenyl)-3-(trifluoromethyl)benzamide Following the procedures as described in Example 17, starting with compound 8 (101 mg, 0.2 mmol), IA-10 was obtained as off-white solid (20 mg, 19%). MS (ESI) m/z: 523 [M+H]$^+$. $^1$H NMR (500 MHz, DMSO-d$_6$): δ 10.36 (s, 1H), 8.73 (s, 1H), 8.20-8.18 (m, 2H), 7.93 (d, J=8.0 Hz, 1H), 7.73-7.65 (m, 2H), 7.60 (s, 1H), 7.53 (s, 1H), 7.42 (s, 1H), 7.35 (dd, J=8.0 Hz, J=2.0 Hz, 1H), 7.16 (d, J=8 Hz, 1H), 4.60 (s, 2H), 4.17 (s, 2H), 3.76 (s, 3H), 2.30 (s, 3H), 3.14 (s, 3H).

Example 20

Synthesis of IA-11

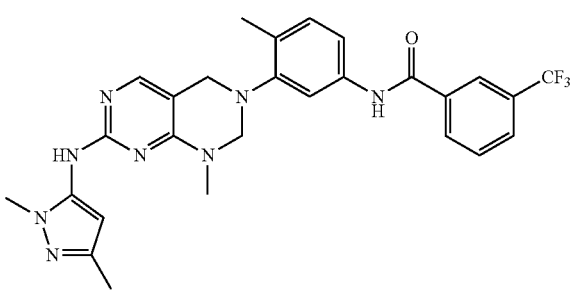

N-(3-(7-((1,3-dimethyl-1H-pyrazol-5-yl)amino)-1-methyl-1,4-dihydropyrimido[4,5-d]pyrimidin-3(2H)-yl)-4-methylphenyl)-3-(trifluoromethyl)benzamide Following the procedures as described in Example 17, starting with compound 8 (101 mg, 0.2 mmol), IA-11 was obtained as off-white solid (15 mg, 12%). MS (ESI) m/z: 536.55 [M+H]$^+$. $^1$H NMR, 500 MHz (MeOD), 8.21 (s, 1H), 8.16 (d, 1H, J=7.5 Hz), 7.88 (d, 1H, J=8.0 Hz), 7.72 (d, 1H, J=7.5 Hz), 7.54 (s, 1H), 7.52 (s, 1H), 7.28 (dd, 1H, J=8.0 Hz, J=2.0 Hz), 7.21 (d, 1H, J=7.5 Hz), 6.03 (s, 1H), 4.68 (s, 2H), 4.23 (s, 2H), 3.63 (s, 3H), 3.15 (s, 3H), 2.38 (s, 3H), 2.19 (s, 3H).

Example 21

Synthesis of IA-12

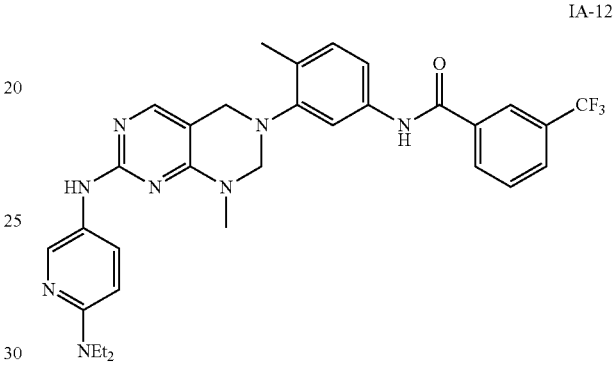

N-(3-(7-((6-(diethylamino)pyridin-3-yl)amino)-1-methyl-1,4-dihydropyrimido[4,5-d]pyrimidin-3(2H)-yl)-4-methylphenyl)-3-(trifluoromethyl)benzamide Following the procedures as described in Example 17, starting with compound 8 (101 mg, 0.2 mmol), IA-12 was obtained as off-white solid (20 mg, 17%). MS (ESI) m/z: 591 [M+H]$^+$. $^1$H NMR (500 MHz, DMSO-d$_6$): δ 10.36 (s, 1H), 8.51 (s, 1H), 8.29 (s, 1H), 8.19-8.21 (m, 2H), 7.93 (d, J=8 Hz, 1H), 7.75-7.79 (m, 2H), 7.57 (s, 1H), 7.54 (s, 1H), 7.36 (dd, J=8.0 Hz, J=2.0 Hz, 1H), 7.16 (d, J=8 Hz, 1H), 6.50 (d, J=9 Hz, 1H), 4.59 (s, 2H), 4.17 (s, 2H), 3.42 (q, J=6 Hz, 4H), 3.12 (s, 3H), 2.30 (s, 3H), 1.07 (t, J=7.5 Hz, 6H).

Example 22

Synthesis of IA-13

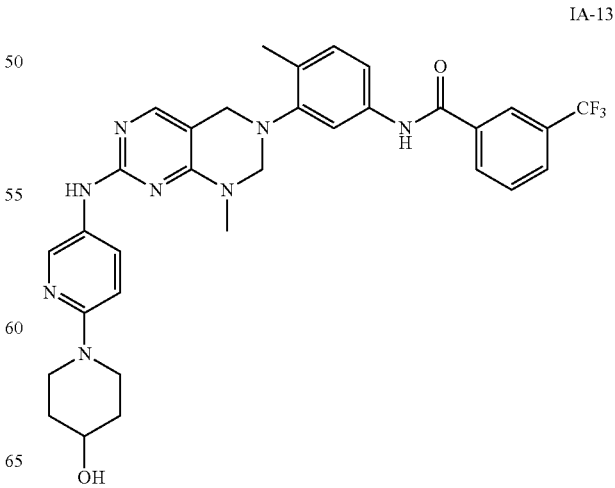

N-(3-(7-((6-(4-hydroxypiperidin-1-yl)pyridin-3-yl)amino)-1-methyl-1,4-dihydropyrimido[4,5-d]pyrimidin-3(2H)-yl)-4-methylphenyl)-3-(trifluoromethyl)benzamide Following the procedures as described in Example 17, starting with compound 8 (101 mg, 0.2 mmol), IA-13 was obtained as off-white solid (17 mg, 14%). MS (ESI) m/z: 619 [M+H]+. 1H NMR (500 MHz, DMSO-$d_6$): δ 10.36 (s, 1H), 8.65 (s, 1H), 8.40 (s, 1H), 8.18-8.20 (m, 2H), 7.93 (d, J=8 Hz, 1H), 7.84-7.86 (m, 1H), 7.75 (t, J=7.5 Hz, 1H), 7.60 (s, 1H), 7.54 (s, 1H), 7.35 (d, J=8 Hz, 1H), 7.16 (d, J=8 Hz, 1H), 6.75 (d, J=8 Hz, 1H), 4.64-4.60 (m, 3H), 4.17 (s, 2H), 3.90-3.87 (m, 2H), 3.65-3.62 (m, 1H), 3.12 (s, 3H), 2.93 (t, J=10 Hz, 2H), 2.30 (s, 3H), 1.76-1.74 (m, 2H), 1.38-1.31 (m, 2H).

Example 23

Synthesis of IA-14

IA-14

N-(4-methyl-3-(1-methyl-7-((6-(4-methylpiperazin-1-yl)pyridin-3-yl)amino)-1,4-dihydropyrimido[4,5-d]pyrimidin-3(2H)-yl)phenyl)-3-(trifluoromethyl)benzamide Following the procedures as described in Example 17, starting with compound 8 (101 mg, 0.2 mmol IA-14 was obtained as a yellow solid (5 mg, 4%). MS (ESI) m/z: 618.3 [M+H]+. 1H NMR, 500 MHz (CDCl3), 8.31 (s, 1H), 8.09 (s, 1H), 8.00 (d, 1H, J=7.6 Hz), 7.83 (d, 1H, J=9.0 Hz), 7.78 (m, 2H), 7.59 (m, 2H), 7.34 (s, 1H), 7.27 (m, 2H), 6.65 (d, 1H, J=9.1 Hz), 4.58 (s, 2H), 4.19 (s, 2H), 3.48 (m, 4H), 3.14 (s, 3H), 2.53 (m, 4H), 2.35 (s, 6H).

Example 24

Synthesis of IA-15

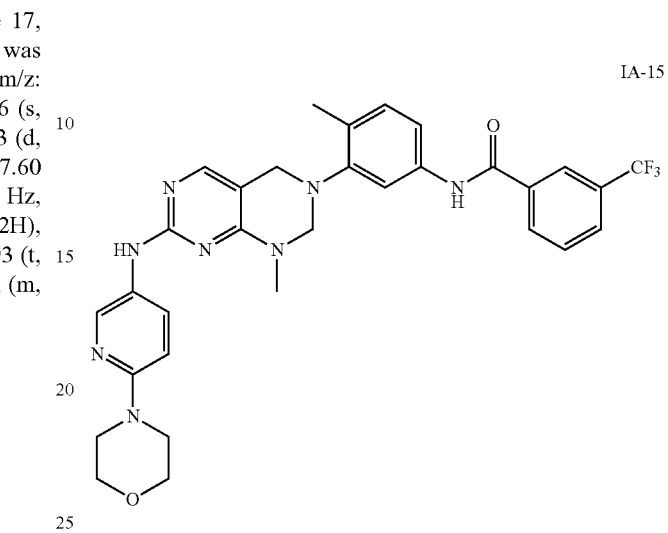

IA-15

N-(4-methyl-3-(1-methyl-7-((6-morpholinopyridin-3-yl)amino)-1,4-dihydropyrimido[4,5-d]pyrimidin-3(2H)-yl)phenyl)-3-(trifluoromethyl)benzamide Following the procedures as described in Example 17, starting with compound 8 (202 mg, 0.4 mmol IA-15 was obtained as a white solid (12 mg, 5%). MS (ESI) m/z: 605.3 [M+H]+. 1H NMR, 500 MHz (DMSO-$d_6$), 8.33 (s, 1H), 8.09 (s, 1H), 8.00 (d, 1H, J=7.5 Hz), 7.86 (dd, 1H, J=9.0 Hz, 3.0 Hz), 7.76-7.79 (m, 3H), 7.47 (s, 1H), 7.61 (t, 1H, J=7.5 Hz), 7.56 (s, 1H), 7.36 (s, 1H), 7.18-7.23 (m, 2H), 6.70 (bs, 1H), 6.64 (d, 1H, J=9.0 Hz), 4.59 (s, 2H), 4.19 (s, 2H), 3.83 (t, 4H, J=4.5 Hz), 3.42 (t, 4H, J=4.5 Hz), 3.16 (s, 3H), 2.35 (s, 3H).

Example 25

Synthesis of IA-16

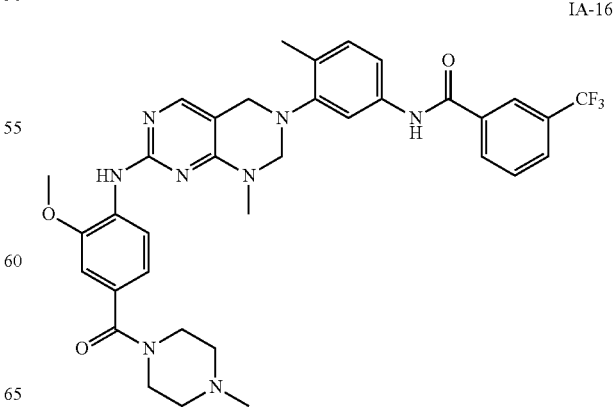

IA-16

N-(3-(7-((2-methoxy-4-(4-methylpiperazine-1-carbonyl)phenyl)amino)-1-methyl-1,4-dihydropyrimido[4,5-d]pyrimidin-3(2H)-yl)-4-methylphenyl)-3-(trifluoromethyl)benzamide Following the procedures as described in Example 17, starting with compound 8 (101 mg, 0.2 mmol), IA-16 was obtained as off-white solid (4 mg, 3%). MS (ESI) m/z: 675 [M+H]$^+$. $^1$H NMR (500 MHz, CDCl$_3$): δ 9.94 (s, 1H), 8.11 (s, 1H), 8.03 (d, J=8 Hz, 1H), 7.96 (s, 1H), 7.79 (d, J=8 Hz, 1H), 7.64-7.60 (m, 2H), 7.33 (s, 1H), 7.25 (s, 1H), 7.18 (d, J=8 Hz, 1H), 6.92 (d, J=8 Hz, 1H), 6.49-6.46 (m, 2H), 4.58 (s, 2H), 4.20 (s, 2H), 3.65 (s, 3H), 3.24 (t, J=5 Hz, 4H), 3.11 (s, 3H), 2.59 (t, J=5 Hz, 4H), 2.37 (s, 3H), 2.33 (s, 3H).

Example 26

General Reaction Sequence for Compounds of Formula IB

Compounds of formula IB were synthesized according to Scheme 2. Exemplary methods are described further below.

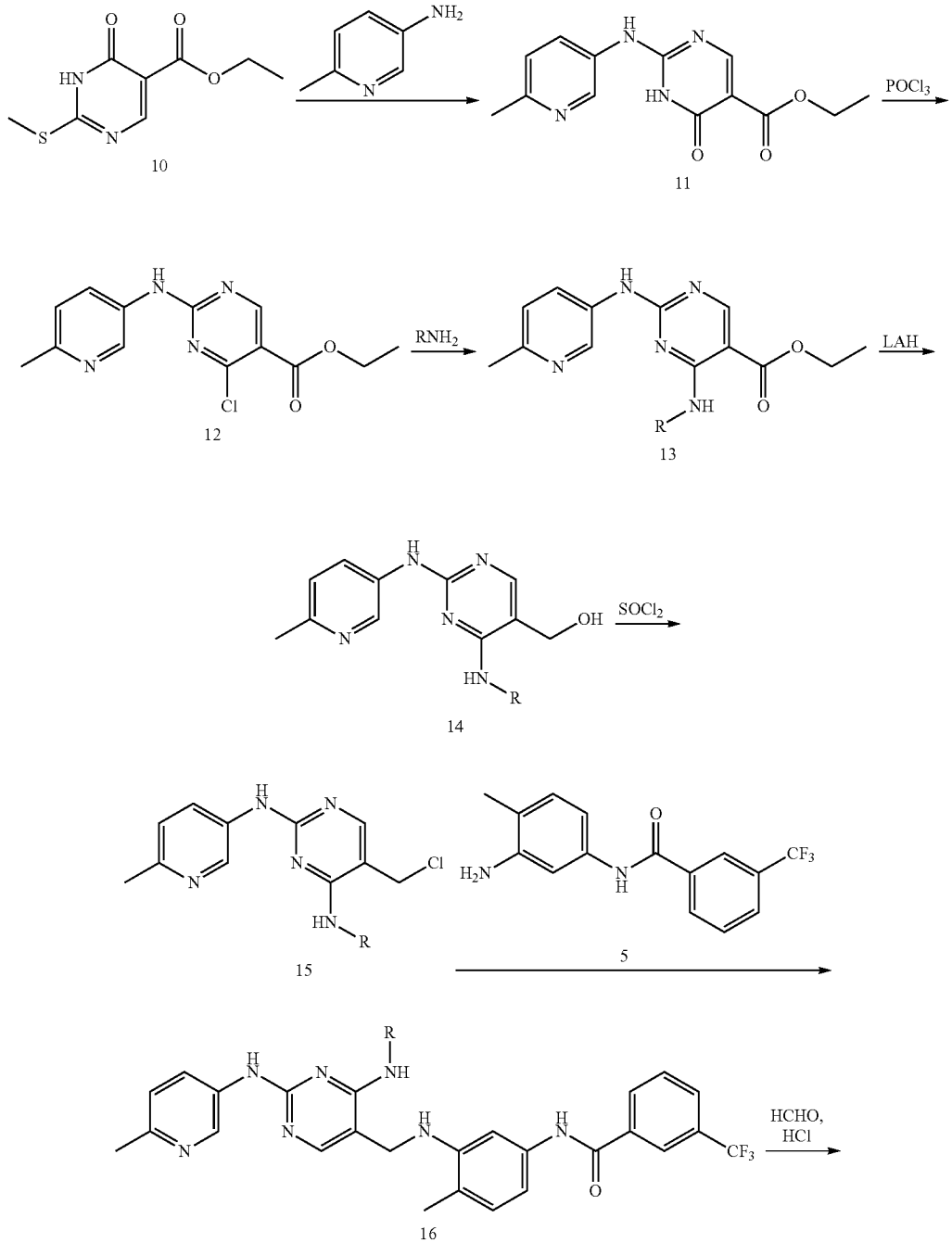

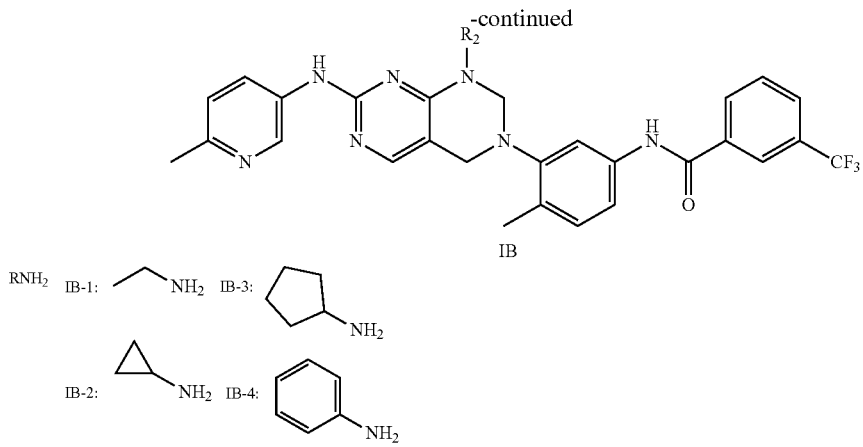

IB

RNH₂  IB-1: methylamine  IB-2: cyclopropylmethylamine  IB-3: cyclopentylamine  IB-4: aniline

Example 27

Synthesis of Compound 11

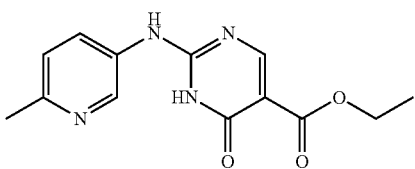

Compound 11

Ethyl 2-((6-methylpyridin-3-yl)amino)-6-oxo-1,6-dihydropyrimidine-5-carboxylate

Compound 11 was synthesized according to methods described by Choi, et al *J. Med. Chem.*, 2010, 53(15), 5439-5448. A mixture of compound 10 (25 g, 117 mmol) and 6-methylpyridin-3-amine (13 g, 120 mmol) was heated to 130° C. for 3 h. After compound 10 was completely consumed as monitored by TLC, the mixture was cooled to rt. The cake was crushed and washed with EtOAc (50 ml) to afford the desired product 11 (28 g, 87% yield) as grey solid. ESI MS m/z: 275 [M+H]⁺. ¹H NMR (400 Mz, DMSO-d₆): δ 11.51 (br, 1H), 9.50 (br, 1H), 8.58 (s, 1H), 8.47 (s, 1H), 7.93 (m, 1H), 7.25 (d, J=8.4 Hz, 1H), 4.18 (q, J=7.2 Hz, 2H), 2.44 (s, 3H), 1.25 (t, J=7.2 Hz, 3H).

Example 28

Synthesis of Compound 12

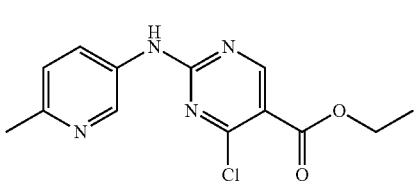

Compound 12

Ethyl 4-chloro-2-((6-methylpyridin-3-yl)amino)pyrimidine-5-carboxylate

Diethylbenzenamine (18.3 g, 122 mmol) was added to a mixture of compound 11 (28 g, 102 mmol) and POCl₃ (31.3 g, 204 mmol), the mixture was heated to 90° C. overnight. The mixture was cooled to rt and concentrated in vacuo. The residue was poured portionwise to crushed ice (200 g) and the resulting solid was collected by suction, washed with a mixture of petroleum ether and EtOAc (1:1, 100 ml), dried under vacuum for 4 h to afford the desired product 12 (14.5 g, 48% yield) as grey solid. ESI MS m/z: 293 [M+H]⁺. ¹H NMR (400 Mz, DMSO-d₆): δ 11.32 (s, 1H), 9.09 (s, 1H), 9.04 (s, 1H), 8.50 (d, J=8.0 Hz, 1H), 7.86 (d, J=8.0 Hz, 1H), 4.33 (q, J=7.2 Hz, 2H), 2.69 (s, 3H), 1.33 (t, J=7.2 Hz, 3H).

Example 29

Synthesis of Compound 14

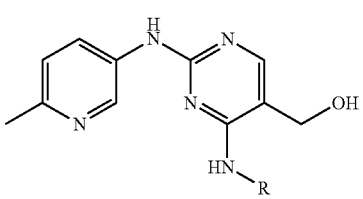

Compound 14

A mixture of compound 12 (900 mg, 3.08 mmol), triethylamine (0.623 g, 6.16 mmol) and corresponding amine (6.16 mmol, 2 eq) in 40 mL of dry THF was stirred overnight under nitrogen at room temperature. The organic solvent was removed by evaporation to give the crude of compound 13, which was used directly for next step.

To a solution of compound 13 (obtained in last step, 3.08 mmol) in 5 mL of dry THF a solution of LiAlH₄ (1.0 M in THF, 6.2 mL, 6.16 mmol) was added dropwise at 0° C. The mixture was warmed to room temperature slowly, and stirred for another 3 h. The reaction mixture was quenched with water (30 mL), extracted with EA (3×100 mL). The organic phases were combined, dried and concentrated. The crude was purified silica gel chromatography to give compound 14 (70%~80% yield for two steps).

Example 30

Synthesis of Compound 16

Compound 16

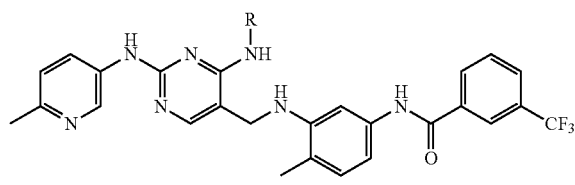

Compound 16 was synthesized according to methods described by Cieplik, et al *Acta Poloniae Pharmaceutica*, 2003, 487-492. A mixture of compound 14 (1.85 mmol) in 5 mL of SOCl$_2$ was heated at 70° C. for 1 h, concentrated. The residue was used directly for the next step. To the crude product of 15 (1.84 mmol) in THF (15 mL) and DMF (5 mL) were added Et$_3$N (559 mg, 5.52 mmol) and compound 5 (543 mg, 1.84 mmol). The mixture was heated at reflux for 1 h and concentrated. The residue was purified by silica gel chromatography to give compound 16 (in 20%~30% yield for two steps).

Example 31

General Reaction Sequence for Compounds of Formula IB

To a mixture of compound 16 (0.172 mmol) in 8 mL of dry THF was added 2 mL of HCHO solution (40%) and one drop of con. HCl. The mixture was heated at reflux for 1 h and concentrated. The residue was purified by silica gel chromatography to give desired product IB.

Example 32

Synthesis of IB-1

IB-1

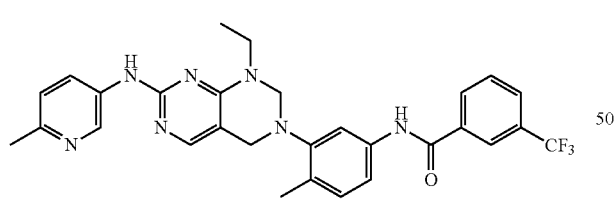

N-(3-(1-ethyl-7-((6-methylpyridin-3-yl)amino)-1,4-dihydropyrimido[4,5-d]pyrimidin-3(2H)-yl)-4-methylphenyl)-3-(trifluoromethyl)benzamide Followed the synthetic procedure as described in Example 31, compound IB-1 was obtained, 43 mg, 46% yield. ESI MS m/z: 548 [M+H]$^+$. $^1$H NMR (MeOD, 500 MHz): 8.76 (d, 1H, J=2.5 Hz), 8.19 (s, 1H), 8.13 (d, 1H, J=8.0 Hz), 8.00 (dd, J=2.5 Hz, 8.5 Hz), 7.86 (d, 1H, J=7.5H), 7.68 (s, 1H), 7.64 (s, 1H), 7.51 (s, 1H), 7.30 (dd, 1H, J=2.0 Hz, 8.5 Hz), 7.23-7.18 (m, 2H), 4.68 (s, 2H), 4.24 (s, 2H), 3.72-3.70 (m, 2H), 2.47 (s, 3H), 2.39 (s, 3H), 1.21 (t, 3H).

Example 33

Synthesis of IB-2

IB-2

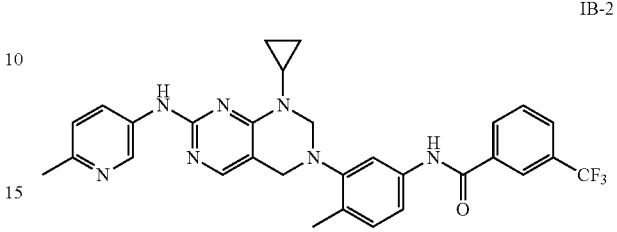

N-(3-(1-cyclopropyl-7-((6-methylpyridin-3-yl)amino)-1,4-dihydropyrimido[4,5-d]pyrimidin-3(2H)-yl)-4-methylphenyl)-3-(trifluoromethyl)benzamide Followed the synthetic procedure as described in Example 31, compound IB-2 was obtained, 51 mg, 50% yield. ESI MS m/z: 560 [M+H]$^+$. $^1$H NMR (400 MHz, DMSO-d$_6$): δ 0.66-1.87 (4H, m), 2.29 (3H, s), 2.36 (3H, s), 2.81 (1H, m), 4.17 (2H, s), 4.59 (2H, s), 7.09 (1H, d, J=8.8 Hz), 7.16 (1H, d, J=8.0 Hz), 7.31 (1H, d, J=8.0 Hz), 7.51 (1H, s), 7.74-7.76 (2H, m), 7.91 (1H, d, J=8.0 Hz), 8.16-8.26 (3H, m), 8.85 (1H, s), 9.10 (1H, s), 10.34 (1H, s).

Example 34

Synthesis of IB-3

IB-3

N-(3-(1-cyclopentyl-7-((6-methylpyridin-3-yl)amino)-1,4-dihydropyrimido[4,5-d]pyrimidin-3(2H)-yl)-4-methylphenyl)-3-(trifluoromethyl)benzamide Followed the synthetic procedure as described in Example 32, compound IB-3 was obtained, 46 mg, 46% yield. ESI MS m/z: 588 [M+H]$^+$. $^1$H NMR (MeOD, 500 MHz): 8.75 (d, 1H, J=2.5 Hz), 8.19 (s, 1H), 8.13 (d, 1H, J=8.0 Hz), 7.98 (dd, J=2.5 Hz, 8.5 Hz), 7.86 (d, 1H, J=7.5H), 7.70-7.67 (m, 2H), 7.46 (s, 1H), 7.33 (dd, 1H, J=2.0 Hz, 8.5 Hz), 7.23 (d, 1H, J=8.5 Hz), 7.19 (d, 1H, J=8.0 Hz), 5.16-5.12 (m, 1H), 4.60 (s, 2H), 4.24 (s, 2H), 2.47 (s, 3H), 2.38 (s, 3H), 1.88-1.85 (m, 2H), 1.74-1.64 (m, 4H), 1.52-1.42 (m, 2H).

Example 35

Synthesis of IB-4

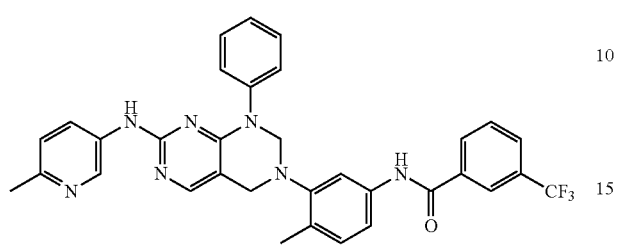

IB-4

N-(4-methyl-3-(7-((6-methylpyridin-3-yl)amino)-1-phenyl-1,4-dihydropyrimido[4,5-d]pyrimidin-3(2H)-yl)phenyl)-3-(trifluoromethyl)benzamide Following the synthetic procedure as described in Example 32, compound IB-4 was obtained, 40 mg, 39% yield. ESI MS m/z: 596 [M+H]⁺. ¹H NMR (400 MHz, DMSO-d$_6$): δ 2.29 (3H, s), 2.30 (3H, s), 4.36 (2H, s), 4.96 (2H, s), 6.82 (1H, d, J=8.0 Hz), 7.18 (1H, d, J=7.6 Hz), 7.20-8.21 (13H, m), 8.46 (1H, s), 9.06 (1H, s), 10.38 (1H, s).

Example 36

General Reaction Sequence for Compounds of Formula IC

Compounds of formula IC were synthesized according to Scheme 3. Exemplary methods are described further below.

Scheme 3. General reaction sequence for compounds of formula IC:

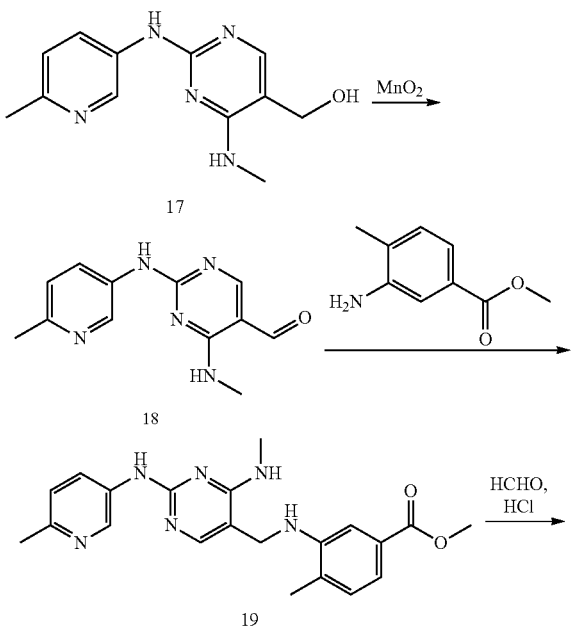

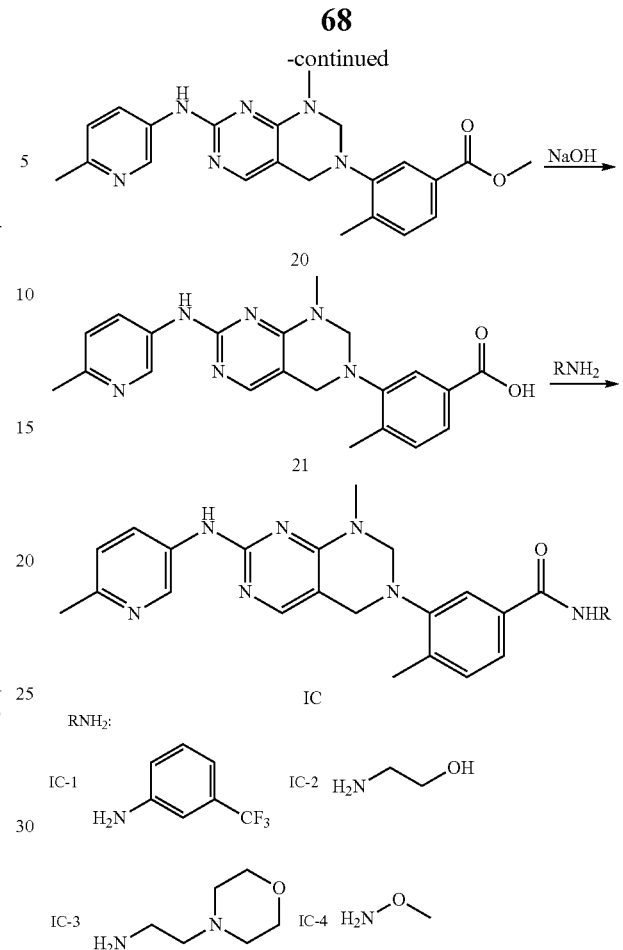

Example 37

Synthesis of Compound 18

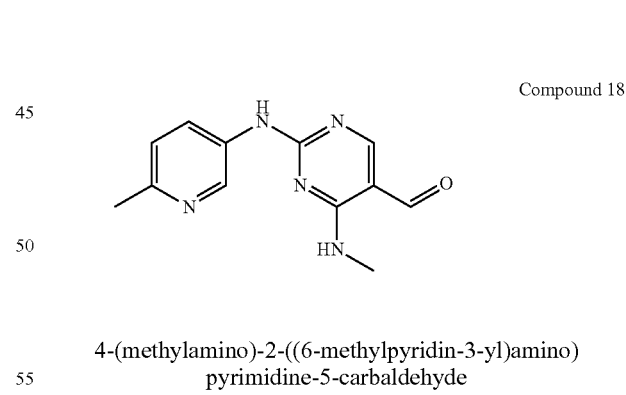

4-(methylamino)-2-((6-methylpyridin-3-yl)amino)pyrimidine-5-carbaldehyde

To a mixture of compound 17 (4.5 g, 18.3 mmol) in CHCl$_3$ (100 ml) was added active MnO$_2$ (8 g, 92 mmol). The mixture was stirred at rt overnight. After compound 17 was completely consumed as monitored by TLC, the mixture was filtered through celite, the cake was washed with CHCl$_3$-MeOH (4:1, 50 ml×2), the combined filtrates were concentrated to give the crude compound 18 (3.5 g, 78% yield) as white solid. ESI MS m/z: 244 [M+H]⁺. ¹H NMR (400 Mz, DMSO-d6): δ 10.04 (br, 1H), 9.56 (s, 1H), 8.84 (br, 1H), 8.61 (br, 1H), 8.47 (s, 1H), 8.08 (d, J=7.2 Hz, 1H), 7.20 (d, J=7.2 Hz, 1H), 3.00 (d, J=4.4 Hz, 3H), 2.41 (s, 3H).

Example 38

Synthesis of Compound 19

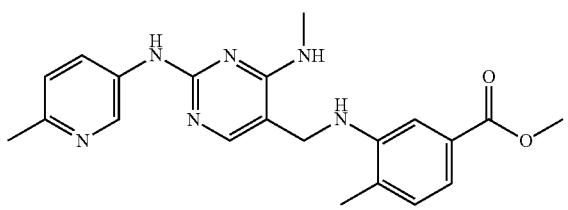

Compound 19

Methyl 4-methyl-3-(((4-(methylamino)-2-((6-methylpyridin-3-yl)amino)pyrimidin-5-yl)methyl)amino)benzoate A mixture of compound 18 and methyl 3-amino-4-methylbenzoate (2.7 g, 16.2 mmol) in DCE (100 ml) was stirred at room temperature for 4 h and then NaBH$_3$CN was added in one portion. The mixture was stirred at room temperature for 2 d until most starting material was consumed as monitored by LCMS. The mixture was concentrated in vacuum, and the residue was purified by silica gel chromatography (THF-petroleum ether=1:1 to 1:0) to afford the pure compound 19 (1.8 g, 31% yield) as white solid. ESI MS m/z: 393 [M+H]$^+$. $^1$H NMR (400 Mz, DMSO-d6): δ 9.05 (s, 1H), 8.80 (s, 1H), 8.08 (dd, J=8.4 Hz, 2.0 Hz, 1H), 7.76 (s, 1H), 7.07-7.15 (m, 4H), 6.95 (d, J=4.0 Hz, 1H), 5.54 (m, 1H), 4.12 (d, J=4.4 Hz, 2H), 3.78 (s, 3H), 2.93 (d, J=4.0 Hz, 3H), 2.36 (s, 3H), 2.17 (s, 3H).

Example 39

Synthesis of Compound 20

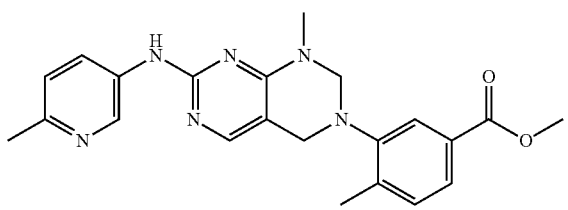

Compound 20

Methyl 4-methyl-3-(1-methyl-7-((6-methylpyridin-3-yl)amino)-1,4-dihydropyrimido[4,5-d]pyrimidin-3(2H)-yl)benzoate To a solution of compound 19 (1.4 g, 3.56 mmol) in 50 mL of THF 10 mL of HCHO solution (40%) was added with one drop of concentrated. HCl. The mixture was heated at reflux for 1 h and concentrated to give the compound 20 (1.5 g, 100% yield) as white solid. Compound 20 was used in the next step without further purification. ESI MS m/z: 405 [M+H]$^+$.

Example 40

Synthesis of Compound 21

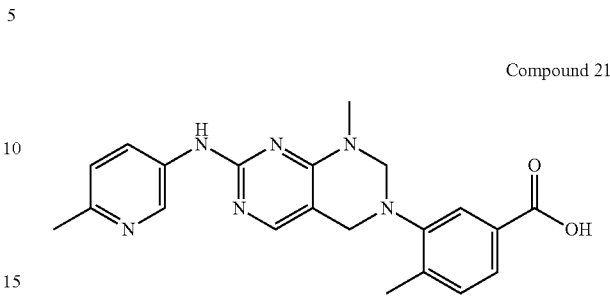

Compound 21

4-methyl-3-(1-methyl-7-((6-methylpyridin-3-yl)amino)-1,4-dihydropyrimido[4,5-d]pyrimidin-3(2H)-yl)benzoic acid To a solution of the crude compound 20 (1.5 g, 3.56 mmol) in MeOH (50 ml) a solution of NaOH (0.57 g, 14.24 mmol) in water (10 ml) was added. The mixture was stirred at 50° C. overnight. The mixture was concentrated and the residue was dissolved in 200 mL of water, lyophilized to afford the crude compound 21 (2.0 g, crude) as yellow powder, which was used directly in the next step without further purification. ESI MS m/z: 391 [M+H]$^+$.

Example 41

Synthesis of IC-1

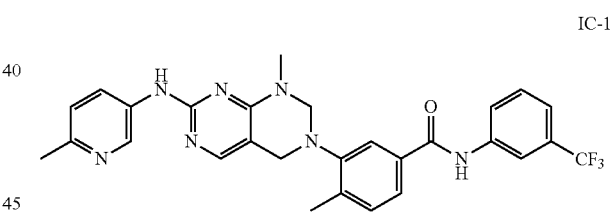

IC-1

4-methyl-3-(1-methyl-7-((6-methylpyridin-3-yl)amino)-1,4-dihydropyrimido[4,5-d]pyrimidin-3(2H)-yl)-N-(3-(trifluoromethyl)phenyl)benzamide A mixture of compound 21 (100 mg, crude, 0.25 mmol) and 3-(trifluoromethyl)benzenamine (50 mg, 0.3 mmol) in dry pyridine (5 ml) at −15° C. POCl$_3$ (1 ml) was mixed with dry pyridine (5 ml) and added to the above mixture. The reaction mixture was stirred for 2 h at −15° C., poured into crushed ice, and extracted with DCM. The combined extracts were washed consecutively with HCl (2 M), aq. NaHCO$_3$ and brine, dried over Na$_2$SO$_4$ and concentrated. The residue was purified by prep-HPLC to give IC-1 (10 mg) as white solid. ESI MS m/z: 534 [M+H]$^+$. $^1$H NMR (500 MHz, DMSO-d$_6$): δ 2.37 (3H, s), 2.42 (s, 3H), 3.14 (s, 3H), 4.25 (s, 2H), 4.68 (s, 2H), 7.10 (d, J=8 Hz, 1H), 7.38 (d, J=8 Hz, 1H), 7.44 (d, J=8 Hz, 1H), 7.54-7.58 (m, 2H), 7.66-7.70 (m, 2H), 8.00-8.06 (m, 2H), 8.20 (m, 1H), 8.75 (s, 1H), 9.07 (s, 1H), 10.44 (s, 1H).

Example 42

Synthesis of IC-2

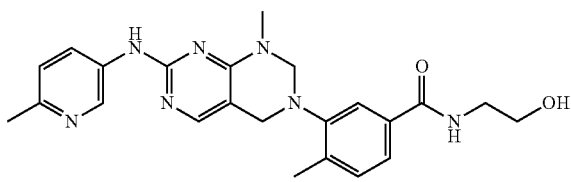

IC-2

N-(2-hydroxyethyl)-4-methyl-3-(1-methyl-7-((6-methylpyridin-3-yl)amino)-1,4-dihydropyrimido[4,5-d]pyrimidin-3(2H)-yl)benzamide A mixture of compound 21 (200 mg, crude, 0.5 mmol), 2-aminoethanol (34 mg, 0.55 mmol), HATU (210 mg, 0.55 mmol) and TEA (101 mg, 1 mmol) in DMF (5 ml) was stirred at room temperature overnight. The mixture was subjected to prep-HPLC to afford the pure IC-2 (19 mg) as white solid. ESI MS m/z: 434 [M+H]$^+$. $^1$H NMR (400 Mz, DMSO-d$_6$): δ 9.07 (s, 1H), 8.76 (d, J=2.0 Hz, 1H), 8.33 (t, J=5.6 Hz, 1H), 8.05 (dd, J=8.0 Hz, 2.4 Hz, 1H), 7.67 (s, 1H), 7.45-7.48 (m, 2H), 7.26 (d, J=8.4 Hz, 1H), 7.10 (d, J=8.4 Hz, 1H), 4.71 (t, J=4.2 Hz, 1H), 4.61 (s, 2H), 3.44-3.50 (m, 2H), 3.25-3.30 (m, 2H), 3.11 (s, 3H), 2.37 (s, 3H), 2.36 (s, 3H).

Example 43

Synthesis of IC-3

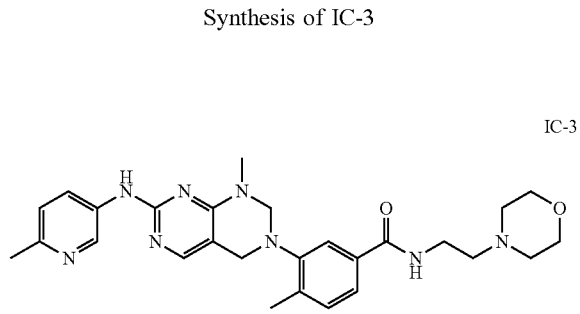

IC-3

4-methyl-3-(1-methyl-7-((6-methylpyridin-3-yl)amino)-1,4-dihydropyrimido[4,5-d]pyrimidin-3(2H)-yl)-N-(2-morpholinoethyl)benzamide Following the same synthetic procedure described in Example 42, compound IC-3 was obtained (32 mg). ESI MS m/z: 503 [M+H]$^+$. $^1$H NMR (400 Mz, DMSO-d$_6$): δ 9.05 (s, 1H), 8.75 (d, J=2.0 Hz, 1H), 8.26 (m, 1H), 8.05 (dd, J=8.0 Hz, 2.0 Hz, 1H), 7.66 (s, 1H), 7.40-7.44 (m, 2H), 7.26 (d, J=8.0 Hz, 1H), 7.09 (d, J=8.0 Hz, 1H), 4.61 (s, 2H), 4.19 (s, 2H), 3.50-3.54 (m, 4H), 3.33 (s, 3H), 3.10 (s, 3H), 2.36-2.42 (m, 10H).

Example 44

Synthesis of IC-4

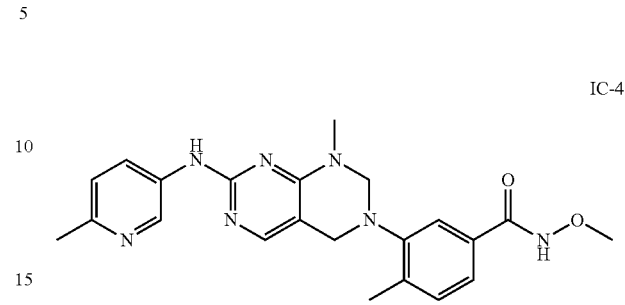

IC-4

N-methoxy-4-methyl-3-(1-methyl-7-((6-methylpyridin-3-yl)amino)-1,4-dihydropyrimido[4,5-d]pyrimidin-3(2H)-yl)benzamide Following the same synthetic procedure described in Example 43, compound IC-4 was obtained (19 mg). ESI MS m/z: 420 [M+H]$^+$. $^1$H NMR (400 Mz, MeOD-d$_4$): δ 8.74 (d, J=1.6 Hz, 1H), 8.03 (dd, J=8.0 Hz, 2.0 Hz, 1H), 7.41 (s, 1H), 7.34 (d, J=8.0 Hz, 1H), 7.28 (d, J=8.0 Hz, 1H), 7.18 (d, J=8.4 Hz, 1H), 4.62 (s, 2H), 4.21 (s, 2H), 3.75 (s, 3H), 3.17 (s, 3H), 2.46 (s, 3H), 2.41 (s, 3H).

Example 45

Synthesis of IC-5

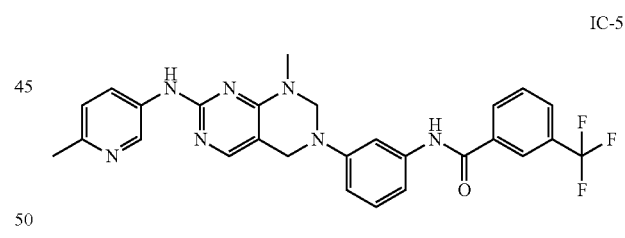

IC-5

N-(3-(1-methyl-7-((6-methylpyridin-3-yl)amino)-1,4-dihydropyrimido[4,5-d]pyrimidin-3(2H)-yl)phenyl)-3-(trifluoromethyl)benzamide Following the same synthetic procedure of Example 39, compound IC-5 was obtained (60 mg). ESI MS m/z: 508 [M+H]$^+$. $^1$H NMR (500 Mz, MeOD-d$_4$): δ 8.75 (s, 1H), 8.26 (s, 1H), 8.20 (d, J=8.0 Hz, 1H), 8.01 (dd, J=8.4 Hz, 3.0 Hz, 1H), 7.90 (d, J=8.0 Hz, 1H), 7.74 (t, J=8.0 Hz, 1H), 7.68 (s, 1H), 7.60 (s, 1H), 7.28 (t, J=8.0 Hz, 1H), 7.20 (t, J=7.5 Hz, 1H), 6.92 (dd, J=2.0 Hz, 8.0 Hz, 1H), 4.95 (s, 2H), 4.52 (s, 2H), 3.21 (s, 3H), 2.47 (s, 3H).

Example 46

Synthesis of IC-6

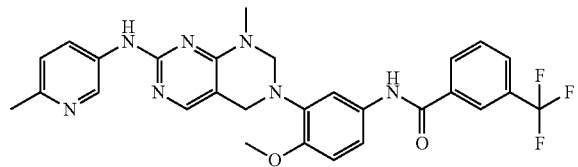

IC-6

N-(4-methoxy-3-(1-methyl-7-((6-methylpyridin-3-yl)amino)-1,4-dihydropyrimido[4,5-d]pyrimidin-3(2H)-yl)phenyl)-3-(trifluoromethyl)benzamide Following the same synthetic procedure of Example 39, compound IC-6 was obtained (11 mg). ESI MS m/z: 550 [M+H]$^+$. $^1$H NMR (500 Mz, MeOD-d$_4$): δ 8.62 (s, 1H), 8.08 (s, 1H), 8.02 (d, J=8.0 Hz, 1H), 7.90 (dd, J=8.5 Hz, 2.0 Hz, 1H), 7.74 (d, J=8.0 Hz, 1H), 7.58 (t, J=8.0 Hz, 1H), 7.50 (s, 1H), 7.33 (d, J=2.0 Hz, 1H), 7.21 (dd, J=2.0 Hz, 8.5 Hz, 1H), 7.06 (d, J=8.5H, 1H), 6.89 (d, J=8.5H, 1H), 4.70 (s, 2H), 4.28 (s, 2H), 3.82 (s, 3H), 3.07 (s, 3H), 2.34 (s, 3H).

Example 47

Synthesis of IC-7

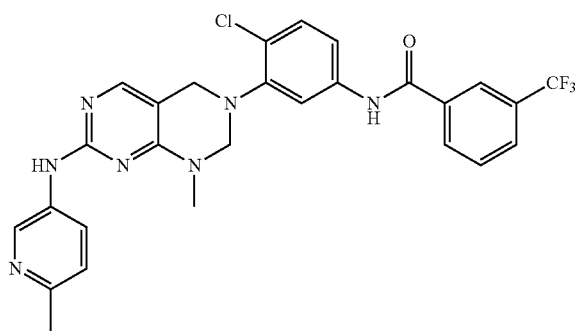 [SMILES: Cc1ccc(Nc2ncc3c(n2)N(C)CN(c2cc(NC(=O)c4cccc(C(F)(F)F)c4)ccc2Cl)C3)cn1]

IC-7

N-(4-chloro-3-(1-methyl-7-((6-methylpyridin-3-yl)amino)-1,4-dihydropyrimido[4,5-d]pyrimidin-3(2H)-yl)phenyl)-3-(trifluoromethyl)benzamide Following the synthetic procedure as described in Example 39, compound IC-7 was obtained (25 mg). ESI MS m/z: 554 [M+H]$^+$. $^1$H NMR (400 MHz, DMSO-d$_6$): δ 10.6 (s, 1H), 9.10 (s, 1H), 8.74 (d, 1H), 8.21 (m, 2H), 8.05 (m, 1H), 8.01 (m, 1H), 7.92 (2H), 7.45 (m, 2H), 7.08 (m, 1H), 7.03 (d, 1H), 4.75 (m, 2H), 4.36 (m, 2H), 3.16 (s, 3H), 2.56 (s, 3H).

Example 48

General Reaction Sequence for Compounds of Formula ID

Compounds of formula ID were synthesized according to Scheme 4. Exemplary methods are described further below.

Scheme 4. General reaction sequence for compounds of formula ID1-ID5:

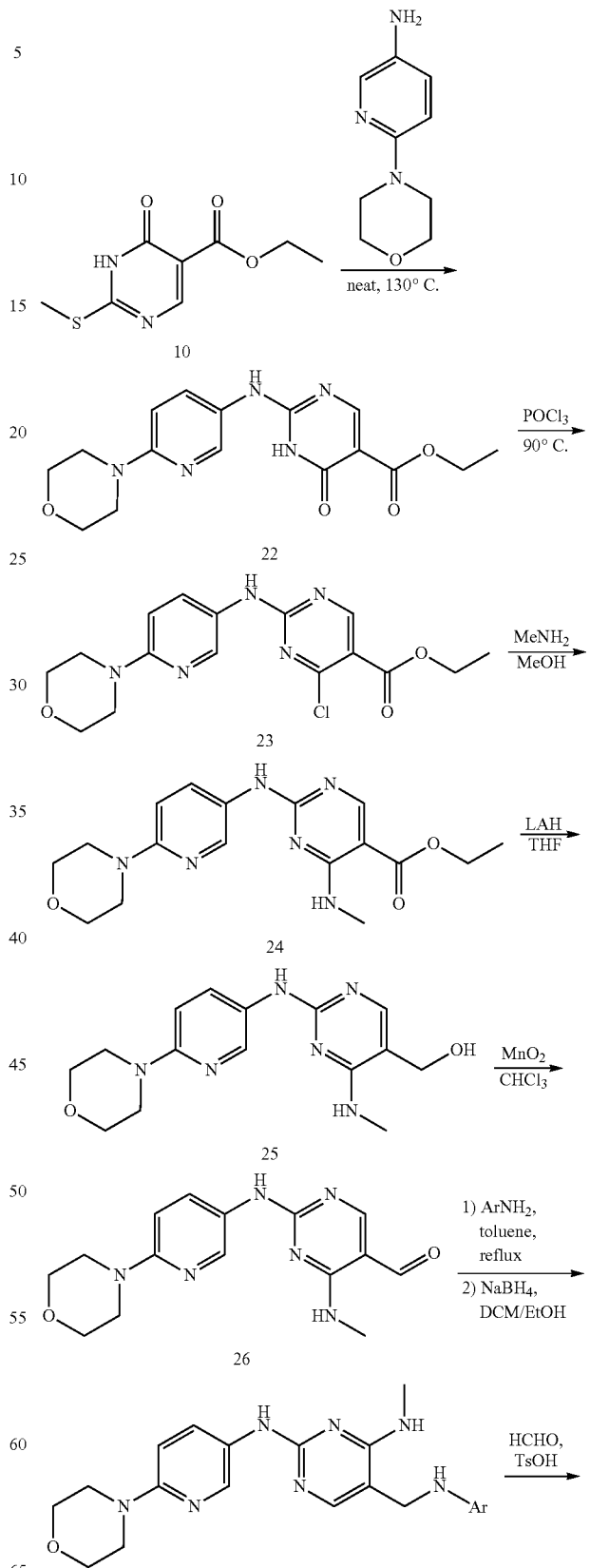

-continued

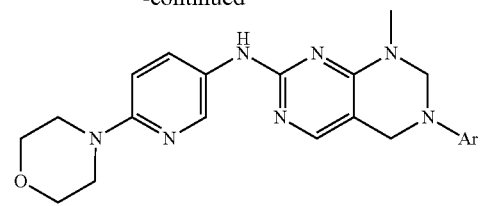

ID-1~ID-5

Example 49

Synthesis of Compound 24

Compound 24

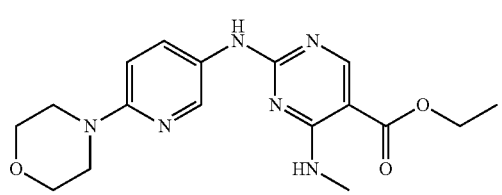

Ethyl 4-(methylamino)-2-((6-morpholinopyridin-3-yl)amino)pyrimidine-5-carboxylate Following the same synthetic procedure of compound 13 (See Example 30), compound 24 was obtained (12.7 g). ESI MS m/z: 359 [M+H]+. $^1$H NMR (500 Mz, DMSO-d$_6$): δ 9.68 (br, 1H), 8.56 (s, 1H), 8.16 (s, 1H), 7.97 (s, 1H), 6.83 (d, J=9.5 Hz, 1H), 4.23 (q, J=7.2 Hz, 2H), 3.69 (s, 3H), 3.36 (s, 4H), 2.96 (s, 3H), 1.28 (t, J=7.2 Hz, 3H).

Example 50

Synthesis of Compound 25

Compound 25

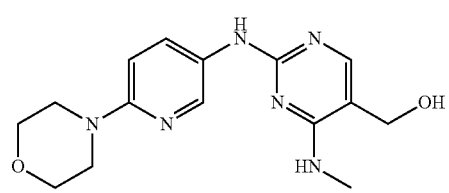

(4-(methylamino)-2-((6-morpholinopyridin-3-yl)amino)pyrimidin-5-yl)methanol

Following the same synthetic procedure of 14 (See Example 30), compound 25 was obtained (6.8 g). ESI MS m/z 317 [M+H]+. $^1$H NMR (500 Mz, DMSO-d$_6$): δ 8.51 (s, 1H), 8.01 (s, 1H), 7.51 (s, 1H), 6.74 (s, 1H), 4.23 (s, 2H), 3.69 (s, 4H), 3.29 (s, 4H), 3.15 (s, 1H), 2.84 (s, 3H).

Example 51

Synthesis of ID-1

ID-1

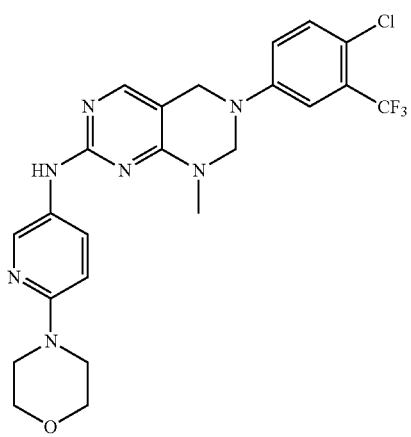 [SMILES: CN1CN(c2ccc(Cl)c(C(F)(F)F)c2)Cc2cnc(Nc3ccc(N4CCOCC4)nc3)nc21]

6-(4-chloro-3-(trifluoromethyl)phenyl)-8-methyl-N-(6-morpholinopyridin-3-yl)-5,6,7,8-tetrahydropyrimido[4,5-d]pyrimidin-2-amine Following the same synthetic procedure of 20 (See Example 40), compound ID-1 was obtained (167 mg). ESI MS m/z: 506 [M+H]+. $^1$H NMR (500 Mz, DMSO-d$_6$): δ 8.78 (s, 1H), 8.43 (d, J=2.5 Hz, 1H), 7.88 (dd, J$_1$=9.0 Hz, J$_2$=3.0 Hz, 1H), 7.72 (s, 1H), 7.53 (d, J=9.0 Hz, 1H), 7.43 (d, J=9.0 Hz, 1H), 7.37 (dd, J=9.0 Hz, 3.0 Hz, 1H), 6.76 (d, J=9.0 Hz, 1H), 4.97 (s, 2H), 4.53 (s, 2H), 3.69 (t, J=4.5 Hz, 4H), 3.32 (t, J=4.5 Hz, 4H), 3.07 (s, 3H).

Example 52

Synthesis of ID-2

ID-2

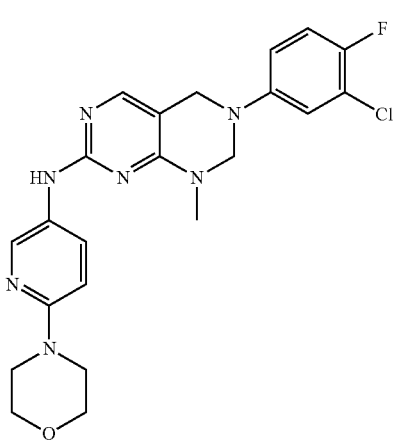 [SMILES: CN1CN(c2ccc(F)c(Cl)c2)Cc2cnc(Nc3ccc(N4CCOCC4)nc3)nc21]

6-(3-chloro-4-fluorophenyl)-8-methyl-N-(6-morpholinopyridin-3-yl)-5,6,7,8-tetrahydropyrimido[4,5-d]pyrimidin-2-amine Following the same synthetic procedure of 20 (See Example 40), compound ID-2 was obtained (80 mg). ESI MS m/z: 456 [M+H]⁺. ¹H NMR (500 Mz, DMSO-d₆): δ 8.76 (s, 1H), 8.43 (d, J=2.5 Hz, 1H), 7.90 (dd, J=9.0 Hz, 3.0 Hz, 1H), 7.69 (s, 1H), 7.24-7.28 (m, 2H), 7.05-7.07 (m, 1H), 6.76 (d, J=9.0 Hz, 1H), 4.89 (s, 2H), 4.44 (s, 2H), 3.69 (t, J=4.5 Hz, 4H), 3.30 (t, J=4.5 Hz, 4H), 3.05 (s, 3H).

Example 53

Synthesis of ID-3

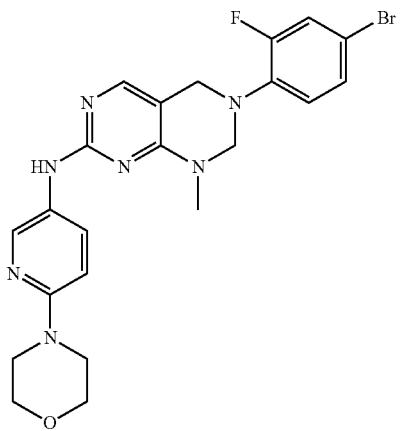 [SMILES: CN1CN(c2ccc(Br)cc2F)Cc2cnc(Nc3ccc(N4CCOCC4)nc3)nc21]

6-(4-bromo-2-fluorophenyl)-8-methyl-N-(6-morpholinopyridin-3-yl)-5,6,7,8-tetrahydropyrimido[4,5-d]pyrimidin-2-amine Following the same synthetic procedure of 20 (See Example 40), compound ID-3 was obtained (27 mg). ESI MS m/z: 501 [M+H]⁺. ¹H NMR (500 Mz, DMSO-d₆): δ 8.78 (s, 1H), 8.45 (d, J=2.5 Hz, 1H), 7.90 (dd, J=9.0 Hz, 3.0 Hz, 1H), 7.66 (s, 1H), 7.51 (dd, J=12.0 Hz, 2.5 Hz, 1H), 7.25 (dd, J=9.0 Hz, 3.0 Hz, 1H), 6.93 (t, J=9.0 Hz, 1H), 6.77 (d, J=9.5 Hz, 1H), 4.74 (s, 2H), 4.33 (s, 2H), 3.69 (t, J=4.5 Hz, 4H), 3.32 (t, J=4.5 Hz, 4H), 3.05 (s, 3H).

Example 54

Synthesis of ID-4

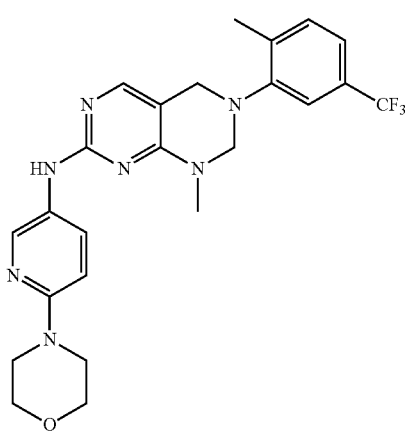 [SMILES: Cc1ccc(C(F)(F)F)cc1N1Cc2cnc(Nc3ccc(N4CCOCC4)nc3)nc2N(C)C1]

8-methyl-6-(2-methyl-5-(trifluoromethyl)phenyl)-N-(6-morpholinopyridin-3-yl)-5,6,7,8-tetrahydropyrimido[4,5-d]pyrimidin-2-amine Following the same synthetic procedure of 20 (See Example 40), compound ID-4 was obtained (40 mg). ESI MS m/z: 486 [M+H]⁺. ¹H NMR (500 Mz, DMSO-d₆): δ 8.81 (s, 1H), 8.47 (s, 1H), 7.92 (dd, J=9.0 Hz, 3.0 Hz, 1H), 7.64 (s, 1H), 7.43 (d, J=7.5 Hz, 1H), 7.32 (d, J=8.0 Hz, 1H), 7.17 (s, 1H), 6.79 (d, J=9.5 Hz, 1H), 4.64 (s, 2H), 4.22 (s, 2H), 3.69 (t, J=4.5 Hz, 4H), 3.32 (t, J=4.5 Hz, 4H), 3.07 (s, 3H), 2.40 (s, 3H).

Example 55

Synthesis ID-5

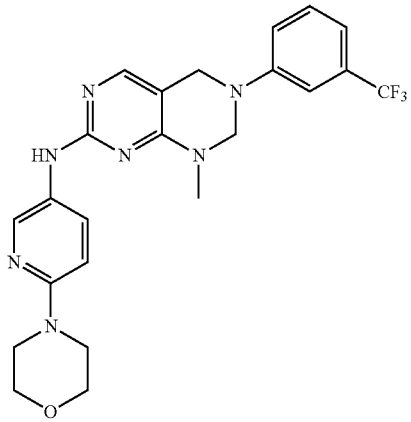 [SMILES: CN1CN(c2cccc(C(F)(F)F)c2)Cc2cnc(Nc3ccc(N4CCOCC4)nc3)nc21]

8-methyl-N-(6-morpholinopyridin-3-yl)-6-(3-(trifluoromethyl)phenyl)-5,6,7,8-tetrahydropyrimido[4,5-d]pyrimidin-2-amine Following the same synthetic procedure of 20 (See Example 40), compound ID-5 was obtained (140 mg). ESI MS m/z: 472 [M+H]⁺. ¹H NMR (500 Mz, DMSO-d₆): δ 8.76 (s, 1H), 8.43 (s, 1H), 7.88 (dd, J=9.0 Hz, 2.5 Hz, 1H), 7.72 (s, 1H), 7.43-7.45 (m, 1H), 7.35-7.38 (m, 2H), 7.14 (d, J=7.5 Hz, 1H), 6.76 (d, J=9.0 Hz, 1H), 4.98 (s, 2H), 4.53 (s, 2H), 3.69 (t, J=4.5 Hz, 4H), 3.32 (t, J=4.5 Hz, 4H), 3.08 (s, 3H).

Example 56

General Reaction Sequence for Compound ID-6

Compound ID-6 were synthesized according to Scheme 5. Exemplary methods are described further below.

Scheme 5. General reaction sequence for compounds of formula ID-6:

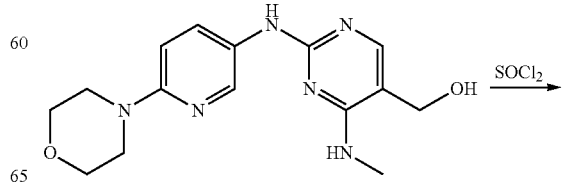

79

-continued

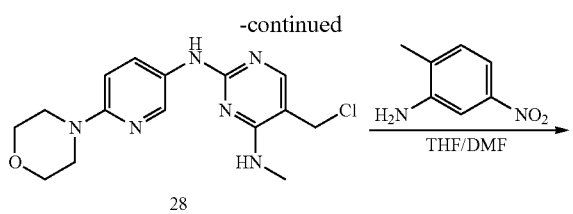

28

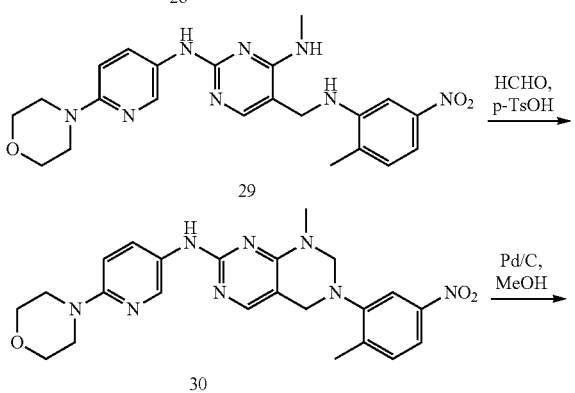

29

30

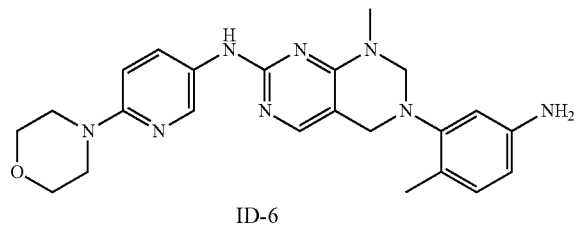

ID-6

Example 57

Synthesis of ID-6

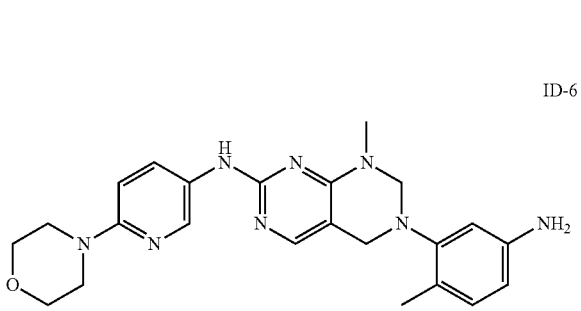

ID-6

6-(5-amino-2-methylphenyl)-8-methyl-N-(6-morpholinopyridin-3-yl)-5,6,7,8-tetrahydropyrimido[4,5-d]pyrimidin-2-amine Following the same synthetic procedure of IB (See Examples 27, 31, and 32), compound 30 was obtained. Reduction of 30 to give the desired product ID-6 (40 mg). ESI MS m/z: 463 [M+H]$^+$. $^1$H NMR (500 Mz, DMSO-d$_6$): δ 8.74 (s, 1H), 8.49 (s, 1H), 7.93 (dd, J=8.5 Hz, 2.5 Hz, 1H), 7.58 (s, 1H), 6.77-6.80 (m, 2H), 6.18-6.19 (m, 2H), 4.80 (s, 2H), 4.51 (s, 2H), 4.08 (s, 2H), 3.69 (t, J=4.5 Hz, 4H), 3.32 (t, J=4.5 Hz, 4H), 3.07 (s, 3H), 2.13 (s, 3H).

Example 58

KINOMEscan Data of Compound IA-9

KINOMEscan™ is based on a competition binding assay that quantitatively measures the ability of a compound to compete with an immobilized, active-site directed ligand (Fabian et al. (2005) Nat. Biotechnol. 23, 329; Karaman et al. (2008) Nat. Biotechnol. 26, 127). The compound was screened at 10 μM, and results for primary screen binding interactions are reported as '% Ctrl', where lower numbers indicate stronger hits. The results for kinases targets with a % Ctrl less than 30 can be seen in Table 2.

% Ctrl Calculation $$\left(\frac{\text{test compound signal} - \text{positive control signal}}{\text{negative control signal} - \text{positive control signal}}\right) \times 100$$

test compound = compound submitted negative control = DMSO (100% Ctrl)

positive control = control compound (0% Ctrl)

Example 59

Inhibition of Oncogenic Protein Kinase Dependent Cell Proliferation

Following up on the kinome data, the ability of compounds disclosed in the present invention to inhibit proliferation of cells that are dependent on selected protein kinases was tested. Compounds of the invention were assayed to measure their capacity to selectively inhibit cell proliferation of Ba/F3 cells [1] expressing BCR/ABL (Ba/F3-p210) or imatinib-resistant BCR/ABL-T315I mutant (Ba/F3-p210-T315I) compared with parental Ba/F3 cells. In addition, compounds were assayed to measure their capacity to inhibit TIE1, LYN, EML4-ALK, INSR and HCK kinases.

The murine cell line used is the BaF/3 cell line transformed with BCR/ABL cDNA (BaF/3-p210) or BCR/ABL-T315I mutant (Ba/F3-p210-T315I). These cells are maintained in RPMI/10% fetal calf serum (RPMI/FCS) supplemented with penicillin 50 μg/mL, streptomycin 50 μg/mL and L-glutamine 200 mM. Untransformed BaF/3 cells (Wt-BaF/3) are similarly maintained with the addition of 15% of WEHI conditioned medium as a source of IL3.

Cells were seeded at a density of 20,000 cells/well into 96-well plates.

Compounds were serially three-fold diluted with growth medium (Cmax=10 μM), and then added in triplicate into 96-well plates and incubated for 48 hours at 37° C. and 5% CO$_2$. The background control wells to which media with no cells added and the vehicle control wells were included on each plate in triplicate. Cell viability was determined using MTT (Sigma, St. Louis, Mo., USA) and MTS (Promega, Madison, Wis., USA), according to the manufacturer's instructions. Results were analyzed using GraphPad Prism 5.0 (GraphPad Software, San Diego, Calif.) and IC$_{50}$ values were calculated from cell viability dose-response curves and defined as the concentration of compound needed to reduce cell viability to 50% of a vehicle control (DMSO) (Table 3).

Cell proliferation assays of compounds of the invention against TIE1, LYN, EML4-ALK, INSR and Hck were conducted using identical methods as described above for BCR/ABL, except that BaF3-TEL-TIE1, BaF3-TEL-LYN, BaF3-EML4-ALK, BaF3-TEL-INSR, and BaF3-TEL-HCK are used instead of BaF3-BCR/ABL (Table 3 and 4).

Example 60

Inhibition of Oncogenic RAS Dependent Cell Proliferation

The BaF/3 cell line transformed with oncogenic NRAS or KRAS (BaF/3-NRASD12 or BaF/3-KRASD12) and the parental BaF/3 cells were used to measure the abilities of compounds of the invention to suppress RAS transformation (Table 5). Cells were seeded at a density of 5000 cells/well into 96-well plates. Compounds were serially three-fold diluted with growth medium (Cmax=10 µM), and then added in triplicate into 96-well plates and incubated for 48 hours at 37° C. and 5% $CO_2$. The background control wells to which media with no cells added and the vehicle control wells were included on each plate in triplicate. Cell viability was determined using CellTiter Glo Assay (Promega) according to manufacture's instruction with a minor modification of diluting 1 part CellTiter Glo reagent to 4 parts phosphate buffered saline (PBS) before use. The luminescence value was read out by an Envision (PerkinElmer).

Example 61

Inhibition of Human Leukemia Cell Proliferation

IA-9 is a strong kinase inhibitor among the compounds of the invention. The activity of IA-9 to inhibit human leukemia cell proliferation was tested using CellTiter Glo Assay (Promega). FIG. 1 shows that IA-9 has a stronger ability to inhibit proliferation of KU812 cells, a human chronic myelogenous leukemia (CML) blast phase cell line harboring the BCR/ABL fusion oncogene (American Type Culture Collection), compared to FDA approved drugs Imatinib and Ponatinib.

Example 62

Anti-Leukemia Activity of Compound IA-9

Figure 2:
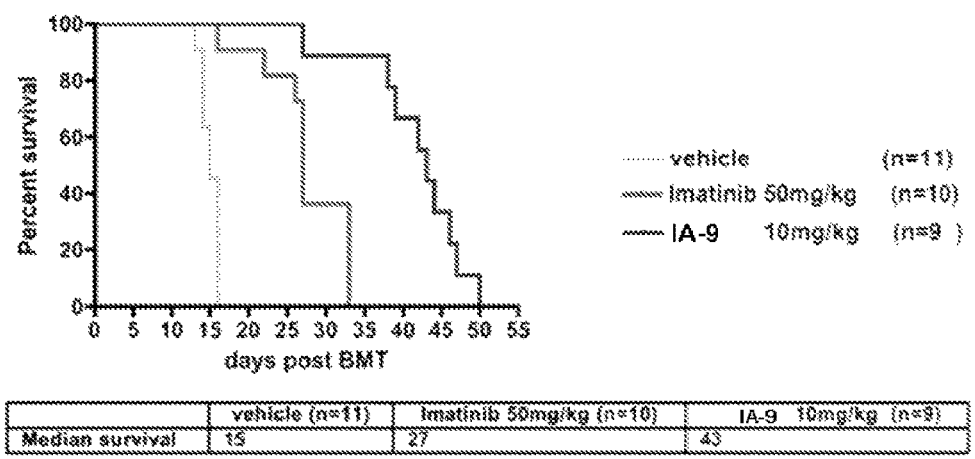
FIG. 2: shows the anti-leukemia activity of IA-9 using a Kaplan-Meier survival curve of CML mice treated with vehicle, Imatinib and IA-9. The number (n) of mice treated in each group was indicated.

The activity of IA-9 to treat leukemia was tested in a mouse CML model as described [4]. Bone marrow cells from 5-fluorouracil (5-FU)-treated male BALB/c donor mice 5 days before were infected at a concentration of $1 \times 10^6$ cells/mL for 24 hours in a cocktail consisting of DMEM, 15% FCS, 5% WEHI-conditioned medium, 50% viral supernatant, 3 µg/mL polybrene, 2 mmol/L L-glutamine, PSA, 7 ng/mL IL-3, 12 ng/mL IL-6 and 56 ng/mL stem cell factor (SCF; R&D System). The infection was repeated once with freshly made retrovirus-containing cocktail as described above. The infected bone marrow cells were then washed once with phosphate-buffered saline and were injected into lethally irradiated (2 doses of 450 rads each dose administered 4 hours apart) syngeneic mice (female BALB/c; 6 to 8 weeks old) through the tail vein at $4 \times 10^5$ cells per mouse. Starting at day post bone marrow transplantation, the recipient mice were treated with vehicle (10% 1-methyl-2-pyrrolidinone:90% PEG-300), 50 mg/kg imatinib or 10 mg/kg IA-9 by oral gavage twice a day. FIG. 2 shows that IA-9 has a significantly stronger anti-leukemia activity.

Example 63

Anti-Melanoma Activity of Compound IA-9

Figure 3:
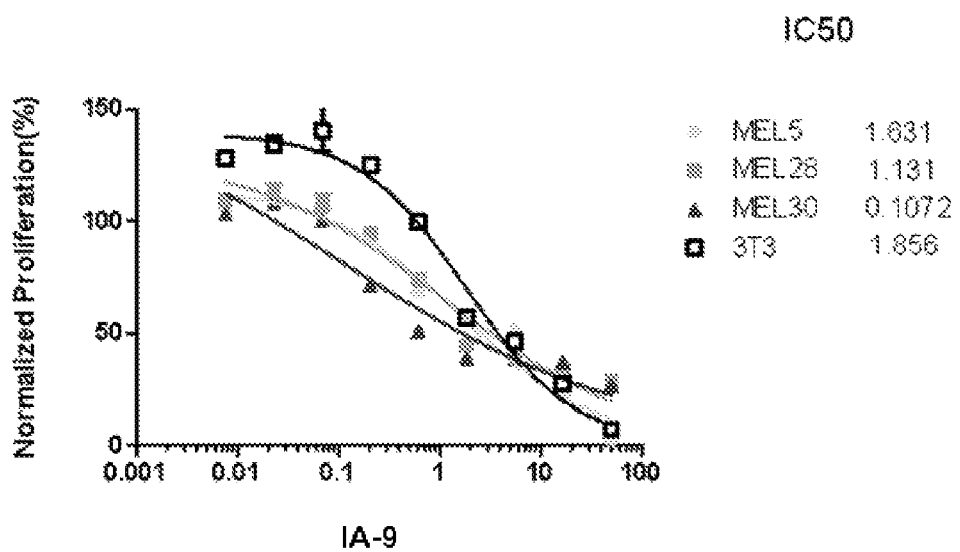
FIG. 3: shows the inhibitory effect of IA-9 on melanoma cell lines harboring NRAS and B-RAF mutations.

The ability of IA-9 to treat melanoma was tested using the SK-MEL-5, SK-MEL-28, and SK-MEL-30 cell lines. SK-MEL-5 and SK-MEL-28 express mutant B-Raf (V600E) and wildtype N-Ras. SK-MEL-30 expresses wildtype B-Raf and mutant N-Ras (Q61K). Cell proliferation was tested using methods described herein. FIG. 3 demonstrates the ability of IA-9 to reduce the proliferation of melanoma cells.

Example 64

Anti-Lung Cancer Activity of Compound IA-9

Figure 4:
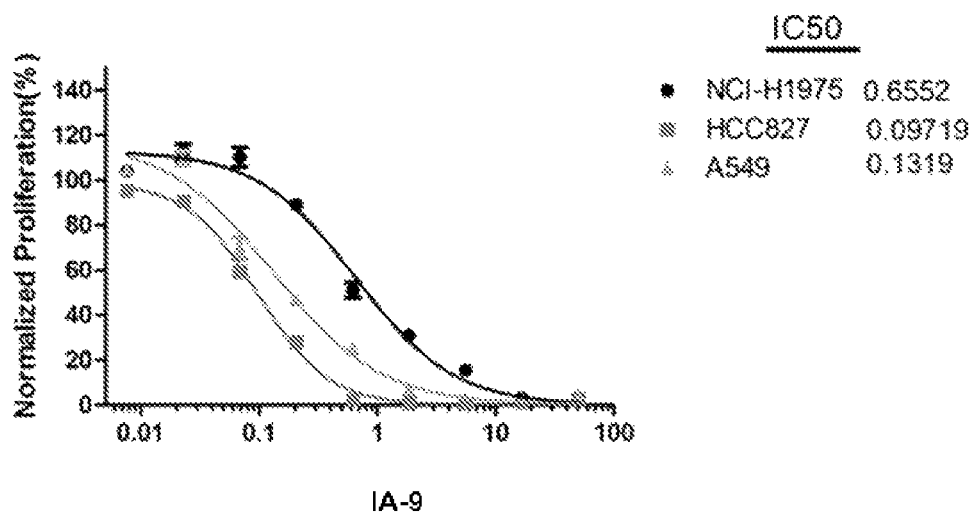
FIG. 4: shows the inhibitory effect of IA-9 on lung adenocarcinoma cell lines harboring EGFR and RAS mutations.

The ability of IA-9 to treat lung adenocarcinoma was tested using the NCI-H1975 and HCC827 cell lines. Both cell lines harbor at least EGFR and Ras mutations and are multi-drug resistant. Cell proliferation was tested using methods described herein. FIG. 4 demonstrates the ability of IA-9 to reduce the proliferation of lung adenocarcinoma cells.

Example 65

Inhibition of Oncogenic FLT3-Driven Leukemia

FLT3 is a receptor tyrosine kinase; its activating mutations are found in 30% human acute myeloid leukemia (AML)[5]. KINOMEscan data, for example as described herein, shows that certain compound(s) of formula I (e.g., IA-9 (IA-9)) bind(s) FLT3 kinase strongly.

Figure 5:
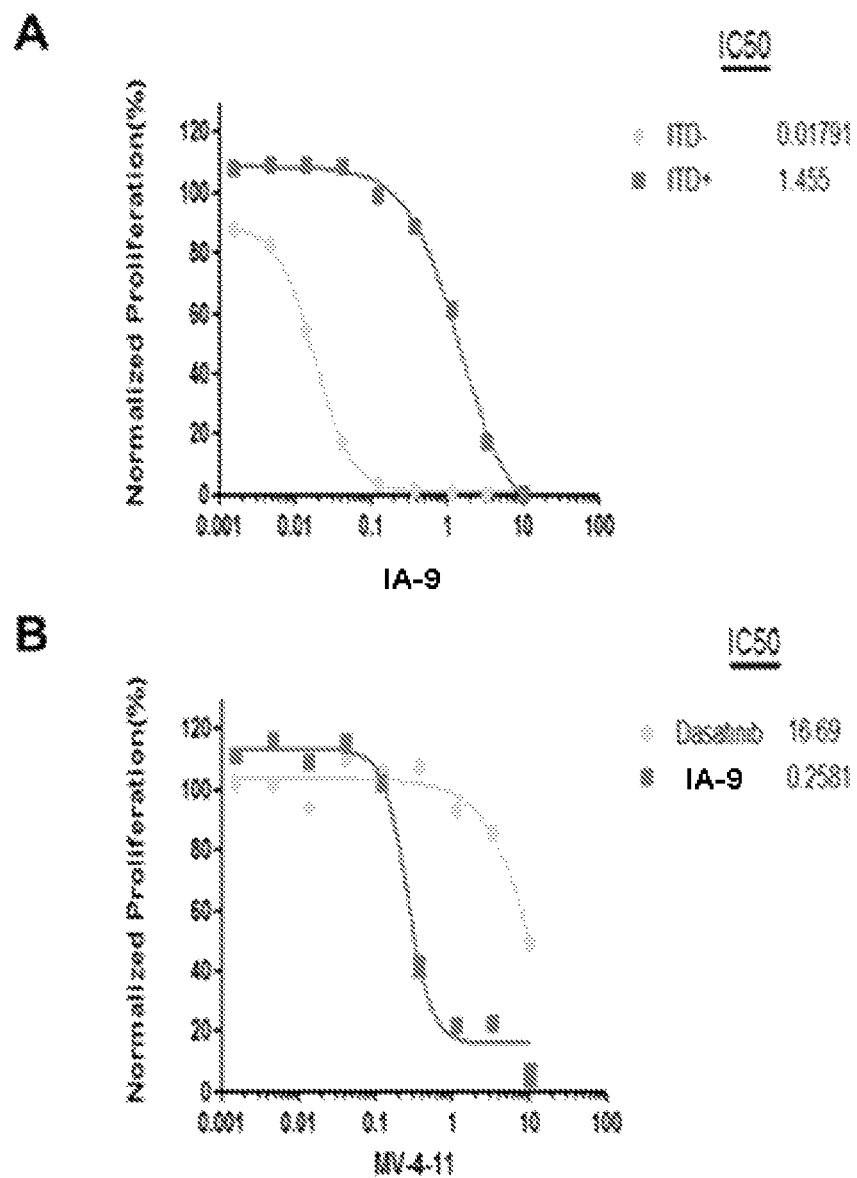
FIG. 5: shows effect(s) of IA-9 in inhibiting FLT3-ITD expressing Ba/F3 cells (ITD) and AML cells (MV-4-11). A. Dose response curve of IA-9 in treating ITD cells is presented. ITD cells in the presence (ITD+) or absence of IL-3 (ITD−) were treated with 10 µM and 3-fold dilution series of IA-9. B. Dose response curve of IA-9 in treating MV-4-11 cells is shown. IA-9.

Capacity of IA-9 to selectively inhibit cell proliferation of Ba/F3 cells expressing FLT3-ITD oncoprotein (ITD), a major oncogenic mutation of FLT3 in AML, was measured. FIG. 5A shows that IA-9 effectively inhibits the proliferation/viability of ITD cells in the absence of IL-3. Addition of IL-3 largely rescues the proliferation/survival of the ITD cells, suggesting that IA-9 specifically inhibits FLT3-ITD transformed cells with a potential therapeutic window of 80-fold dosage.

Furthermore, effect(s) of IA-9 in inhibiting proliferation of FLT3-ITD-driven human AML demonstrated that IA-9 can suppress growth of MV-4-11, a human AML cell line harboring FLT-ITD mutation, much more effectively than did Dasatinib, a FDA approved kinase inhibitor treating BCR/ABL positive leukemias (FIG. 5B).

REFERENCES

1. Palacios R, Steinmetz M. IL3-dependent mouse clones that express B-220 surface antigen, contain Ig genes in germ-line configuration, and generate B lymphocytes in vivo. *Cell.* 1985; 41:727-734.
2. Bos J L. ras oncogenes in human cancer: a review [published erratum appears in Cancer Res 1990 Feb. 15; 50(4):1352]. *Cancer Res.* 1989; 49(17):4682-4689.
3. Malumbres M, Barbacid M. RAS oncogenes: the first 30 years. *Nat Rev Cancer.* June 2003; 3(6):459-465.
4. Zhang X, Ren R. Bcr-Abl efficiently induces a myeloproliferative disease and production of excess interleukin-3 and granulocyte-macrophage colony-stimulating factor in mice: a novel model for chronic myelogenous leukemia. *Blood.* 1998; 92(10):3829-3840.
5. Genomic and epigenomic landscapes of adult de novo acute myeloid leukemia. *N Engl J Med.* May 30 2013; 368(22):2059-2074.

TABLE 2

KINOMEscan data of compound IA-9

| KINOMEscan Gene Symbol | Entrez Gene Symbol | Percent Control |
|---|---|---|
| ABL1(F317I)-nonphosphorylated | ABL1 | 0 |
| ABL1(F317L)-nonphosphorylated | ABL1 | 0 |
| ABL1(T315I)-nonphosphorylated | ABL1 | 0 |
| EGFR(G719C) | EGFR | 0 |
| EGFR(G719S) | EGFR | 0 |
| EGFR(L747-E749del, A750P) | EGFR | 0 |
| EGFR(L747-S752del, P753S) | EGFR | 0 |
| EGFR(L861Q) | EGFR | 0 |
| EGFR(S752-I759del) | EGFR | 0 |
| EPHA4 | EPHA4 | 0 |
| EPHA6 | EPHA6 | 0 |
| EPHB2 | EPHB2 | 0 |
| EPHB3 | EPHB3 | 0 |
| EPHB4 | EPHB4 | 0 |
| ERBB2 | ERBB2 | 0 |
| ERBB4 | ERBB4 | 0 |
| FGR | FGR | 0 |
| FLT4 | FLT4 | 0 |
| FRK | FRK | 0 |
| KIT(V559D) | KIT | 0 |
| LOK | STK10 | 0 |
| p38-beta | MAPK11 | 0 |
| PDGFRB | PDGFRB | 0 |
| RET | RET | 0 |
| RET(M918T) | RET | 0 |
| RET(V804L) | RET | 0 |
| RET(V804M) | RET | 0 |
| TXK | TXK | 0 |
| ABL1(H396P)-nonphosphorylated | ABL1 | 0.05 |
| EGFR | EGFR | 0.05 |
| EGFR(L858R) | EGFR | 0.05 |
| FYN | FYN | 0.05 |
| KIT | KIT | 0.05 |
| KIT(D816V) | KIT | 0.05 |
| YES | YES1 | 0.05 |
| ABL2 | ABL2 | 0.1 |
| BRAF(V600E) | BRAF | 0.1 |
| CIT | CIT | 0.1 |
| LYN | LYN | 0.1 |
| p38-alpha | MAPK14 | 0.1 |
| TAK1 | MAP3K7 | 0.1 |
| TNNI3K | TNNI3K | 0.1 |
| ABL1(H396P)-phosphorylated | ABL1 | 0.15 |
| ABL1(Y253F)-phosphorylated | ABL1 | 0.15 |
| BTK | BTK | 0.15 |
| CSF1R | CSF1R | 0.15 |
| EPHA8 | EPHA8 | 0.15 |
| EPHB1 | EPHB1 | 0.15 |
| LCK | LCK | 0.15 |
| SRC | SRC | 0.15 |
| ABL1(Q252H)-phosphorylated | ABL1 | 0.2 |
| EPHA2 | EPHA2 | 0.2 |
| FLT3 | FLT3 | 0.2 |
| ABL1-nonphosphorylated | ABL1 | 0.3 |
| ABL1-phosphorylated | ABL1 | 0.3 |
| BLK | BLK | 0.3 |
| EPHB6 | EPHB6 | 0.3 |
| KIT(V559D, T670I) | KIT | 0.3 |
| MEK5 | MAP2K5 | 0.3 |
| YSK4 | YSK4 | 0.3 |
| EPHA1 | EPHA1 | 0.35 |
| JAK2(JH1domain-catalytic) | JAK2 | 0.35 |
| KIT(V559D, V654A) | KIT | 0.35 |
| PFCDPK1(P. falciparum) | CDPK1 | 0.35 |
| SIK | SIK1 | 0.35 |
| EGFR(L747-T751del, Sins) | EGFR | 0.4 |
| TIE2 | TEK | 0.45 |
| BRAF | BRAF | 0.5 |
| EPHA7 | EPHA7 | 0.55 |
| FLT1 | FLT1 | 0.55 |
| FLT3(ITD) | FLT3 | 0.55 |
| FLT3(K663Q) | FLT3 | 0.55 |
| FLT3(N841I) | FLT3 | 0.55 |
| HCK | HCK | 0.55 |
| TEC | TEC | 0.55 |
| ZAK | ZAK | 0.55 |
| MAP4K4 | MAP4K4 | 0.6 |
| FES | FES | 0.7 |
| JNK2 | MAPK9 | 0.7 |
| ABL1(Q252H)-nonphosphorylated | ABL1 | 0.75 |
| BMX | BMX | 0.75 |
| BRK | PTK6 | 0.9 |
| CSK | CSK | 0.9 |
| EPHA5 | EPHA5 | 0.9 |
| SRMS | SRMS | 0.95 |
| IKK-alpha | CHUK | 1 |
| DDR1 | DDR1 | 1.1 |
| ABL1(E255K)-phosphorylated | ABL1 | 1.2 |
| ABL1(M351T)-phosphorylated | ABL1 | 1.2 |
| KIT(L576P) | KIT | 1.2 |
| FGFR1 | FGFR1 | 1.3 |
| GCN2(Kin.Dom.2, S808G) | EIF2AK4 | 1.3 |
| MAP3K3 | MAP3K3 | 1.3 |
| PDGFRA | PDGFRA | 1.6 |
| STK36 | STK36 | 1.6 |
| JAK1(JH1domain-catalytic) | JAK1 | 2 |
| MEK4 | MAP2K4 | 2 |
| VEGFR2 | KDR | 2 |
| EGFR(E746-A750del) | EGFR | 2.3 |
| TNK2 | TNK2 | 2.4 |
| MAP4K5 | MAP4K5 | 2.5 |
| RSK4(Kin.Dom.2-C-terminal) | RPS6KA6 | 2.6 |
| FGFR2 | FGFR2 | 2.7 |
| ABL1(F317L)-phosphorylated | ABL1 | 3.2 |
| FLT3(D835H) | FLT3 | 3.2 |
| CTK | MATK | 3.4 |
| FER | FER | 3.6 |
| KIT(A829P) | KIT | 3.6 |
| MINK | MINK1 | 3.6 |
| HPK1 | MAP4K1 | 3.8 |
| ABL1(F317I)-phosphorylated | ABL1 | 4.1 |
| ABL1(T315I)-phosphorylated | ABL1 | 4.1 |
| SYK | SYK | 4.4 |
| MAP4K2 | MAP4K2 | 4.6 |
| TNIK | TNIK | 4.8 |
| JAK3(JH1domain-catalytic) | JAK3 | 5 |
| MAP3K2 | MAP3K2 | 5 |
| KIT(D816H) | KIT | 5.4 |
| TIE1 | TIE1 | 5.6 |
| MLK1 | MAP3K9 | 5.7 |
| MLK3 | MAP3K11 | 5.8 |
| RIPK2 | RIPK2 | 6 |
| SLK | SLK | 6.1 |
| FAK | PTK2 | 6.6 |
| MUSK | MUSK | 6.8 |
| AURKC | AURKC | 6.9 |
| ASK2 | MAP3K6 | 7 |
| MERTK | MERTK | 7 |
| TRKC | NTRK3 | 7.2 |
| GAK | GAK | 7.4 |
| MAP3K15 | MAP3K15 | 8.4 |
| FLT3(D835Y) | FLT3 | 9 |
| DDR2 | DDR2 | 9.1 |
| TRKB | NTRK2 | 10 |
| EPHA3 | EPHA3 | 11 |
| RAF1 | RAF1 | 12 |
| TNK1 | TNK1 | 12 |
| EGFR(T790M) | EGFR | 13 |
| IKK-beta | IKBKB | 14 |
| AURKB | AURKB | 15 |
| CDC2L1 | CDK11B | 15 |
| TAOK2 | TAOK2 | 15 |
| DRAK2 | STK17B | 17 |
| ROS1 | ROS1 | 17 |
| WNK3 | WNK3 | 18 |
| PIP5K2C | PIP4K2C | 19 |
| FLT3(R834Q) | FLT3 | 20 |
| PIP5K1C | PIP5K1C | 21 |
| SIK2 | SIK2 | 21 |
| ALK | ALK | 22 |
| DRAK1 | STK17A | 22 |
| LTK | LTK | 22 |

TABLE 2-continued

KINOMEscan data of compound IA-9

| KINOMEscan Gene Symbol | Entrez Gene Symbol | Percent Control |
|---|---|---|
| EGFR(L858R, T790M) | EGFR | 24 |
| FGFR4 | FGFR4 | 25 |
| PRKCQ | PRKCQ | 25 |
| TRPM6 | TRPM6 | 26 |
| CDC2L2 | CDC2L2 | 28 |
| JNK1 | MAPK8 | 28 |
| RIPK1 | RIPK1 | 28 |
| MAP3K1 | MAP3K1 | 29 |
| TAOK3 | TAOK3 | 29 |
| NEK4 | NEK4 | 30 |

TABLE 3

Antiproliferative activities of compounds of the invention against BaF3-BCR/ABL, BaF3-BCR/ABL-T315I, BaF3-TEL-TIE1 and BaF3-TEL-LYN.

| Cmpd ID | BCR/ABL $IC_{50}$ (nM) | BCR/ABL T315I $IC_{50}$ (nM) | tel-TIE1 $IC_{50}$ (µM) | tel-LYN $IC_{50}$ (µM) |
|---|---|---|---|---|
| IA-1 | 4285 | 4150 | 1.745 | ~2.788 |
| IA-2 | >10000 | ND | 1.589 | 1.322 |
| IA-3 | 1036 | >10000 | 5.469 | 4.089 |
| IA-4 | 956 | 9721 | 4.967 | 1.322 |
| IA-5 | 1722 | 2916 | 3.244 | 2.14 |
| IA-6 | 2219 | 4447 | 3.702 | ~3.207 |
| IA-7 | 665.4 | >10000 | 4.216 | 4.477 |
| IA-8 | 1944 | >10000 | 3.649 | 2.504 |
| IA-9 | 5 | 651.4 | 0.519 | 0.2248 |
| IA-10 | 0.2508 | 2757 | 2.319 | 1.426 |
| IA-11 | 7.961 | 1756 | 0.7363 | 0.9272 |
| IA-12 | 205.1 | 4499 | 1.353 | 1.162 |
| IA-13 | 5.854 | 226.4 | 0.2892 | 0.1319 |
| IA-14 | | | | |
| IA-15 | 4.179 | 131.9 | 0.3554 | 0.2643 |
| IA-16 | 1707 | 4365 | 1.58 | 2 |
| IB-1 | 5.959 | 881.2 | 1.286 | 1.265 |
| IB-2 | 53.81 | 2895 | 1.094 | 1.198 |
| IB-3 | 302.6 | 9232 | 3.821 | 3.304 |
| IB-4 | 669 | ND | 3.683 | 4.11 |
| IC-1 | 6.935 | 196.1 | 0.09116 | 0.1885 |
| IC-2 | 6362 | >10000 | >10 | >10 |
| IC-3 | 216.8 | >10000 | >10 | >10 |
| IC-4 | 63.06 | >10000 | >10 | >10 |
| IC-5 | 940.4 | >10000 | 9.291 | >10 |
| IC-6 | 386.8 | 7999 | 5.177 | ~8.226 |
| IC-7 | 8996 | >10000 | 6.85 | 5.336 |
| ID-1 | ND | >10000 | >10 | >10 |
| ID-2 | >10000 | >10000 | 11.78 | 20.54 |
| ID-3 | >10000 | >10000 | 4.548 | 7.272 |
| ID-4 | 1635 | >10000 | 4.431 | 4.29 |
| ID-5 | ND | >10000 | 6.167 | 15 |
| ID-6 | 352.5 | >10000 | 0.809 | 2.31 |

TABLE 4

Antiproliferative activities of compounds of the invention against BaF3-EML4-ALK, BaF3-TEL-INSR, and BaF3-TEL-HCK.

| Cmpd ID | EML4-ALK $IC_{50}$ (µM) | Tel-INSR $IC_{50}$ (µM) | Tel-HCK $IC_{50}$ (µM) |
|---|---|---|---|
| IA-1 | 1.531 | ND | ND |
| IA-2 | ~2.785 | 1.333 | 2.564 |
| IA-3 | 6.338 | ND | ND |
| IA-4 | 6.794 | ND | ND |
| IA-5 | 4.055 | ND | ND |
| IA-6 | ~3.356 | ND | ND |
| IA-7 | 7.472 | ND | ND |
| IA-8 | 9.222 | ND | ND |
| IA-9 | 1.465 | 0.8693 | 0.6392 |
| IA-10 | 4.635 | ND | 1.772 |
| IA-11 | 2.217 | 2.284 | 1.393 |
| IA-12 | 3.19 | 0.9773 | 3.072 |
| IA-13 | 1.872 | 0.32 | 0.192 |
| IA-14 | | | |
| IA-15 | 1.156 | 0.9016 | 0.6804 |
| IA-16 | 1.535 | 3.956 | 2.883 |
| IB-1 | 2.645 | 3.227 | 0.327 |
| IB-2 | 3.13 | 2.161 | 2.094 |
| IB-3 | 5.879 | ND | 3.146 |
| IB-4 | >10 | ND | 4.608 |
| IC-1 | 1.65 | ND | ND |
| IC-2 | >10 | ND | ND |
| IC-3 | >10 | ND | ND |
| IC-4 | >10 | ND | ND |
| IC-5 | >10 | ND | ND |
| IC-6 | ~9.025 | ND | ND |
| IC-7 | 9.726 | ND | ND |
| ID-1 | >10 | ND | ND |
| ID-2 | >10 | ND | ND |
| ID-3 | 19.95 | ND | ND |
| ID-4 | 8.242 | ND | ND |
| ID-5 | >10 | ND | ND |
| ID-6 | >10 | ND | ND |

TABLE 5

Antiproliferative activities of compounds of the invention against BaF3-NRASD12, BaF3-KRASD12, and Wt-BaF3.

| Cmpd ID | NRas-BaF3 $IC_{50}$ (µM) | KRas-BaF3 $IC_{50}$ (µM) | Wt-BaF3 $IC_{50}$ (µM) |
|---|---|---|---|
| IA-1 | 5.224 | 10.13 | 8.834 |
| IA-2 | 3.384 | 3.978 | 4.544 |
| IA-3 | 11.51 | 6.468 | 12.45 |
| IA-4 | 9.558 | 8.326 | 11.29 |
| IA-5 | 3.292 | 3.439 | 6.297 |
| IA-6 | 5.502 | 5.533 | 5.137 |
| IA-7 | 8.275 | 8.101 | 24.35 |
| IA-8 | 5.213 | 7.566 | 17.94 |
| IA-9 | 0.38 | | 5.38 |
| IA-10 | 2.902 | 4.599 | 11.76 |
| IA-11 | 1.022 | 1.493 | 13.52 |
| IA-12 | 2.304 | 1.823 | 4.113 |
| IA-13 | 0.501 | 0.402 | 2.341 |
| IA-14 | 1.531 | 1.463 | 3.665 |
| IA-15 | 0.404 | 0.388 | 1.766 |
| IA-16 | 4.411 | 4.308 | 4.418 |
| IB-1 | 1.503 | 2.113 | 4.84 |
| IB-2 | 1.405 | 1.777 | 6.029 |
| IB-3 | 5.968 | 5.835 | 9.706 |
| IB-4 | 4.927 | 5.36 | 17.13 |
| IC-1 | 1.57 | 1.689 | 5.36 |
| IC-2 | >10 | >10 | >10 |
| IC-3 | >10 | >10 | >10 |
| IC-4 | >10 | >10 | >10 |
| IC-5 | >10 | >10 | 29.32 |
| IC-6 | 8.154 | 10.35 | 22.84 |

We claim:
1. A compound of formula IA:
IA
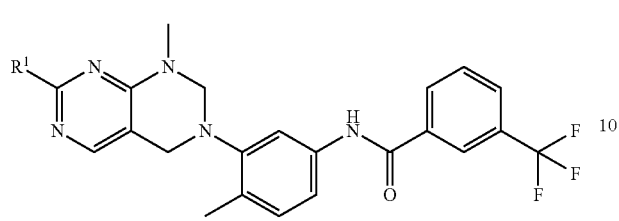
or a pharmaceutically acceptable salt thereof, wherein:
R¹ is selected from —N(R)₂; and
each R is independently selected from hydrogen; methyl; or a group selected from:
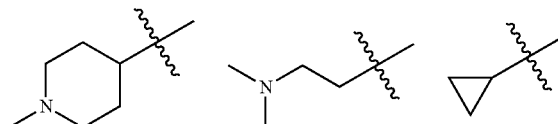
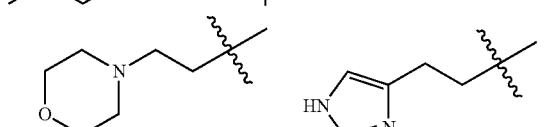
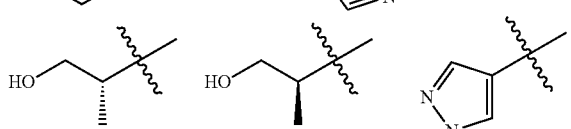
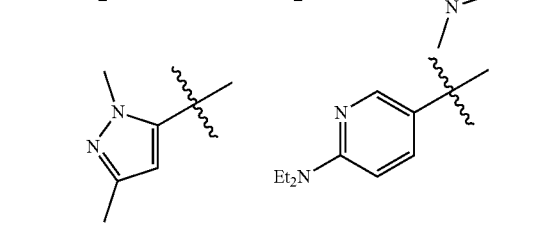
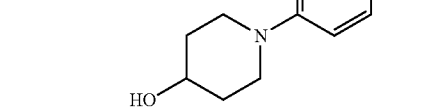
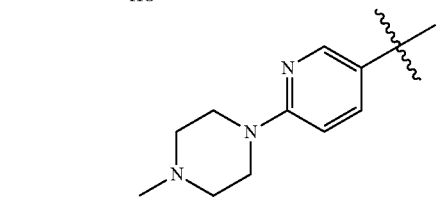
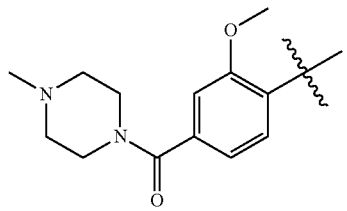
2. A compound selected from:
IA-1
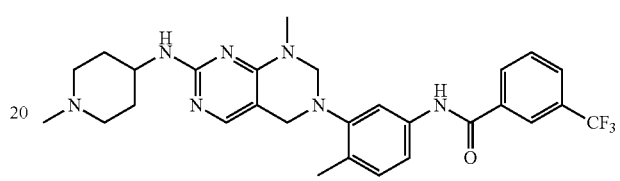
IA-2
IA-3
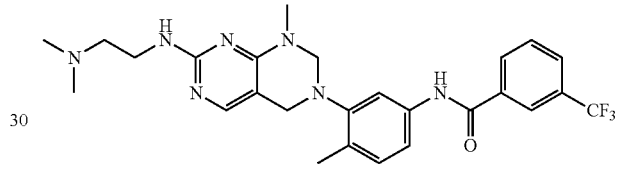
IA-4
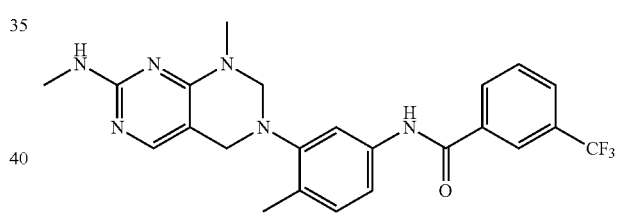
IA-5
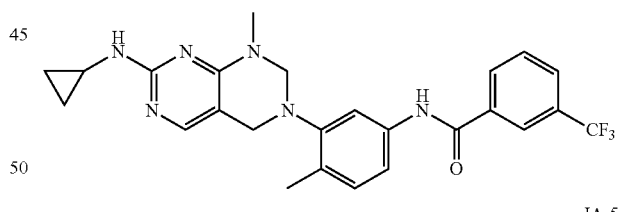
IA-6
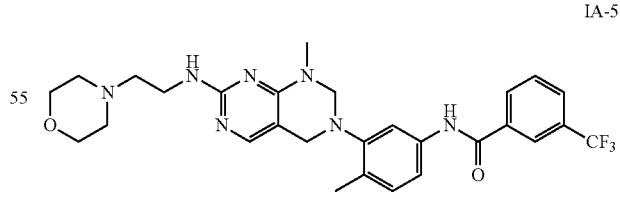
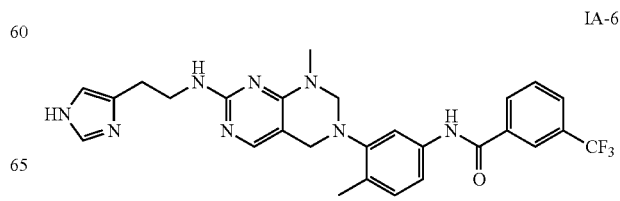

IA-7
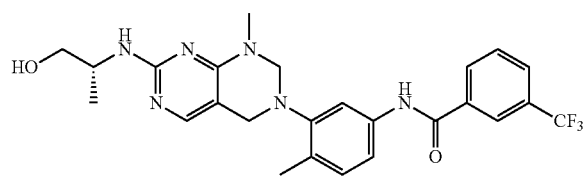
IA-8
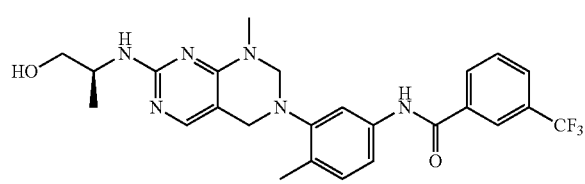
IA-10
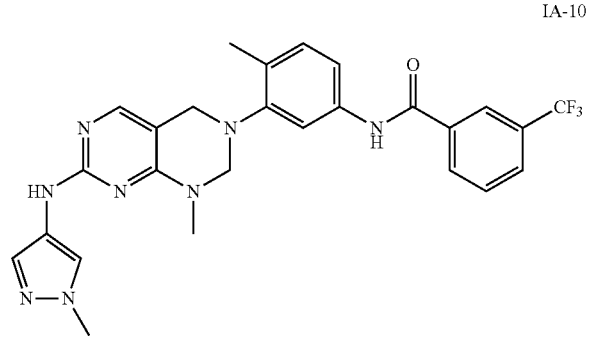
IA-11
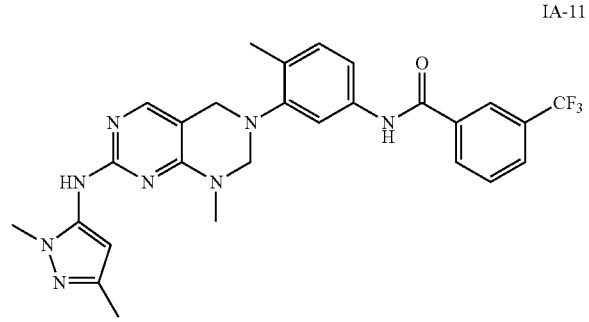 [SMILES: Cc1cc(Nc2ncc3c(n2)N(C)CN(c2cc(NC(=O)c4cccc(C(F)(F)F)c4)ccc2C)C3)n(C)n1]
IA-12
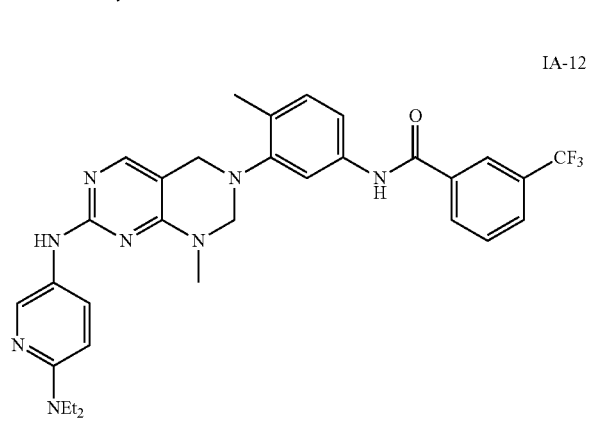
IA-13
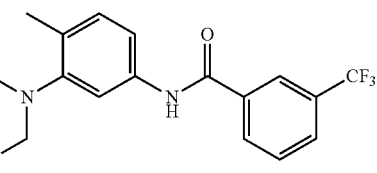
IA-14
IA-15
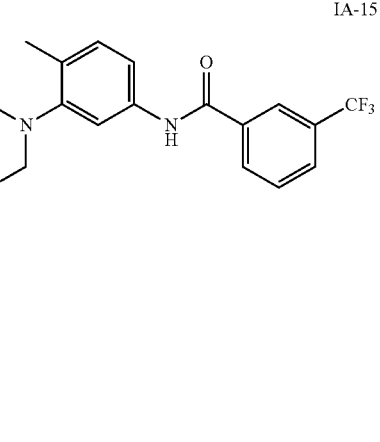

IA-16
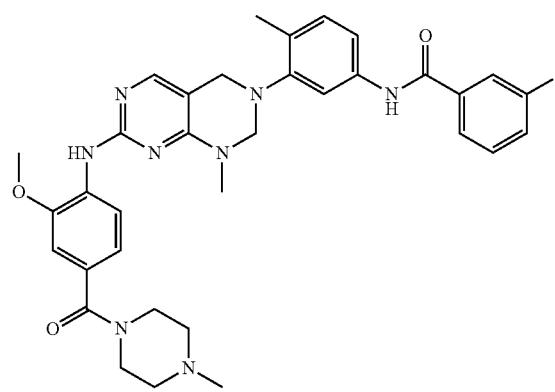
IB-1
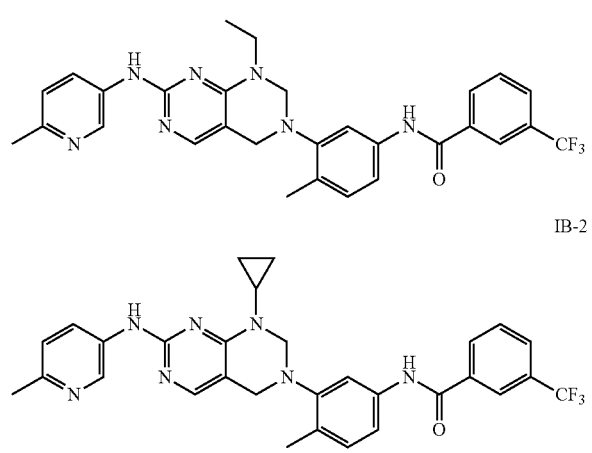
IB-2
IB-3
IB-4
IC-1
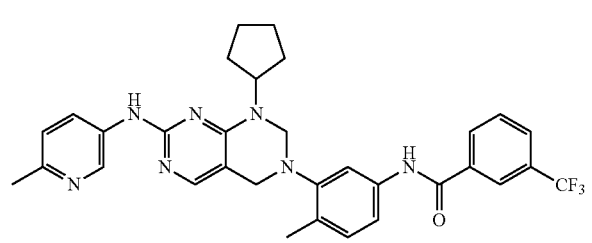
IC-2
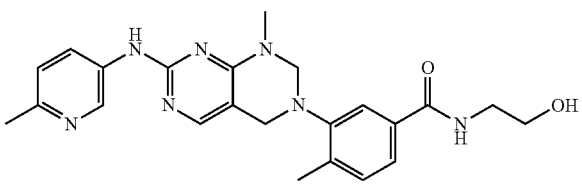
IC-3
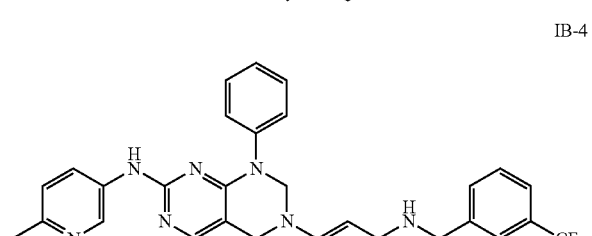
IC-4
IC-5
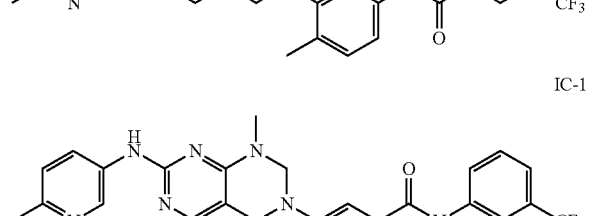
IC-6
IC-7
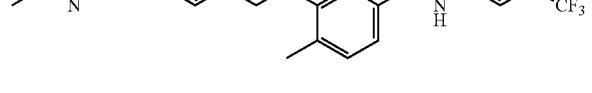

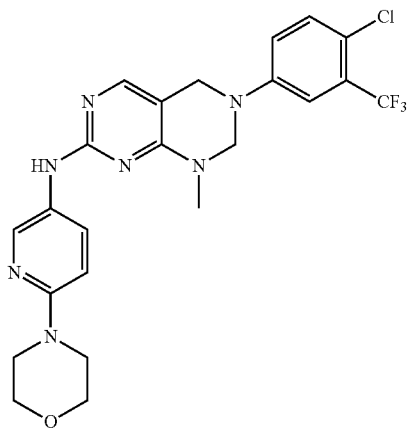

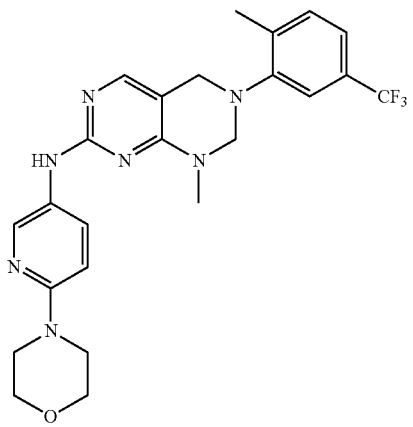

3. A pharmaceutical composition comprising a therapeutically effective amount of a compound of claim 1 or claim 2 provided with a pharmaceutically acceptable excipient.

4. A method of treating cancer in a subject, comprising: administering a therapeutically effective amount of a compound of claim 1 or claim 2, wherein the cancer is selected from the group consisting of lung cancer, breast cancer, melanoma, chronic myeloid leukemia (CML), acute lymophocytic leukemia (ALL), acute myeloid leukemia (AML), and colorectal cancer.

5. The method of claim 4, wherein the subject has received prior treatment for the cancer.

6. The method of claim 4, wherein the subject has developed resistance to a prior treatment regimen.

* * * * *